United States Patent
Iida et al.

(10) Patent No.: US 11,719,603 B2
(45) Date of Patent: Aug. 8, 2023

(54) COLLECTING APPARATUS FOR MICROSCOPIC OBJECTS, COLLECTING CONTAINER USED IN COLLECTING APPARATUS, AND METHOD OF COLLECTING MICROSCOPIC OBJECTS

(71) Applicant: University Public Corporation Osaka, Osaka (JP)

(72) Inventors: Takuya Iida, Sakai (JP); Shiho Tokonami, Sakai (JP); Yasuyuki Yamamoto, Sakai (JP)

(73) Assignee: University Public Corporation Osaka, Osaka (JP)

( * ) Notice: Subject to any disclaimer, the term of this patent is extended or adjusted under 35 U.S.C. 154(b) by 966 days.

(21) Appl. No.: 16/488,768

(22) PCT Filed: Feb. 28, 2018

(86) PCT No.: PCT/JP2018/007608
§ 371 (c)(1),
(2) Date: Aug. 26, 2019

(87) PCT Pub. No.: WO2018/159706
PCT Pub. Date: Sep. 7, 2018

(65) Prior Publication Data
US 2019/0383708 A1     Dec. 19, 2019

(30) Foreign Application Priority Data
Feb. 28, 2017 (JP) .................... 2017-037316

(51) Int. Cl.
*G01N 1/02* (2006.01)
*B01J 19/00* (2006.01)
(Continued)

(52) U.S. Cl.
CPC ............. *G01N 1/02* (2013.01); *B01J 19/00* (2013.01); *B01L 3/5088* (2013.01); *G01N 1/28* (2013.01);
(Continued)

(58) Field of Classification Search
None
See application file for complete search history.

(56) References Cited

U.S. PATENT DOCUMENTS

2017/0074760 A1* 3/2017 Iida .................. G01N 15/00

FOREIGN PATENT DOCUMENTS

| JP | 2007-225330 A | 9/2007 |
| JP | 2009281794 A | 12/2009 |

(Continued)

OTHER PUBLICATIONS

"Water Meniscus." Water Meniscus | U.S. Geological Survey, Jun. 28, 2019. https://www.usgs.gov/special-topics/water-science-school/science/water-meniscus. (Year: 2019).*
(Continued)

*Primary Examiner* — Elizabeth A Robinson
*Assistant Examiner* — Ryan J Dowty
(74) *Attorney, Agent, or Firm* — Marshall, Gerstein & Borun LLP

(57) ABSTRACT

A collecting apparatus for bacteria includes: a laser beam source configured to emit a laser beam; and a container configured to hold a dispersion liquid in which a plurality of bacteria are dispersed. The container has a bottom surface and an inner side surface. A thin film for converting the laser beam from the laser beam source into heat is formed on the bottom surface. At the inner side surface, immersion wetting occurs by the dispersion liquid when the inner side surface comes into contact with the dispersion liquid. The thin film is configured to produce a thermal convection in the disper-
(Continued)

sion liquid by heating the dispersion liquid. The inner side surface is configured to produce a Marangoni convection at a gas-liquid interface as an interface between the dispersion liquid and gas around the dispersion liquid.

1 Claim, 45 Drawing Sheets

(51) Int. Cl.
B01L 3/00 (2006.01)
G01N 1/28 (2006.01)
G02B 21/00 (2006.01)
G02B 21/30 (2006.01)
G02B 21/36 (2006.01)
G02B 21/34 (2006.01)

(52) U.S. Cl.
CPC ......... *G02B 21/0016* (2013.01); *G02B 21/30* (2013.01); *G02B 21/34* (2013.01); *G02B 21/362* (2013.01); *B01L 2300/047* (2013.01)

(56) References Cited

FOREIGN PATENT DOCUMENTS

| | | |
|---|---|---|
| JP | 2011-62607 A | 3/2011 |
| JP | 2013-254940 A | 12/2013 |
| WO | WO-2015/150758 A1 | 10/2015 |
| WO | WO-2015/170758 A1 | 11/2015 |

OTHER PUBLICATIONS

Soukupova, Jana, Libor Kvitek, Martina Kratochvilova, Ales Panacek, Robert Prucek, and Radek Zboril. "Silver voyage from macro-to nanoworld." Journal of chemical education 87, No. 10 (2010): 1094-1097 (Year: 2010).*
Collins, Florence. "Reducing Dead Volumes with Three Key Actions." News Medical Life Sciences. Tecan, Jul. 19, 2016. https://www.news-medical.net/whitepaper/20160719/Reducing-Dead-Volumes-with-Three-Key-Actions.aspx. (Year: 2016).*
Decision to Grant Patent communication issued in Japanese Patent Application No. 2019-503080 dated Dec. 21, 2021.
International Search Report issued in PCT Patent Application No. PCT/JP2018/007608 dated Jun. 5, 2018.

* cited by examiner

FIG.2
(A) <COMPARATIVE EXAMPLE>
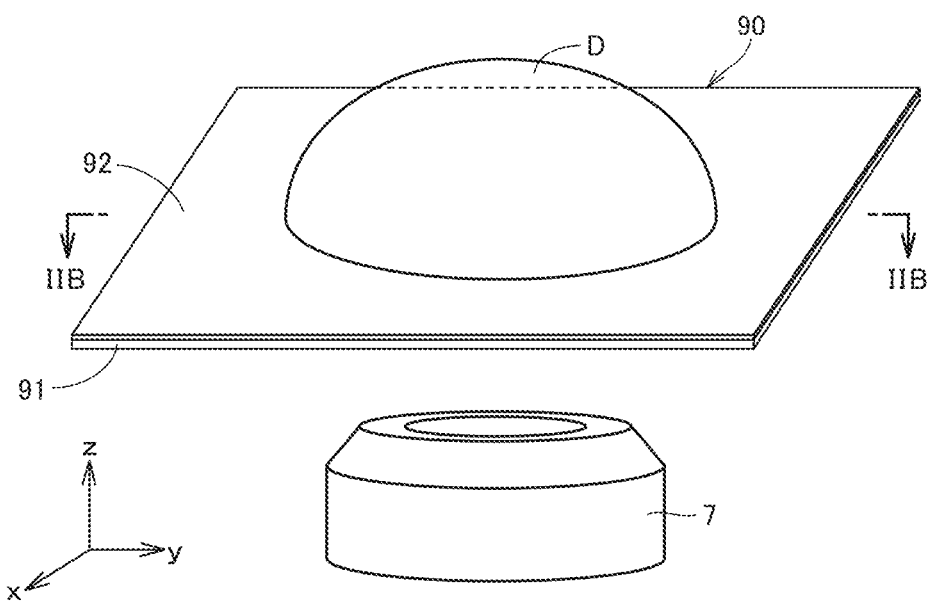
(B)
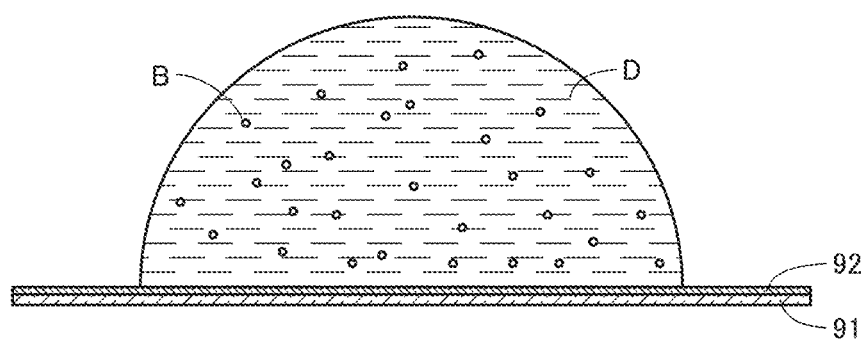

FIG.3 <FIRST EMBODIMENT>
(A)
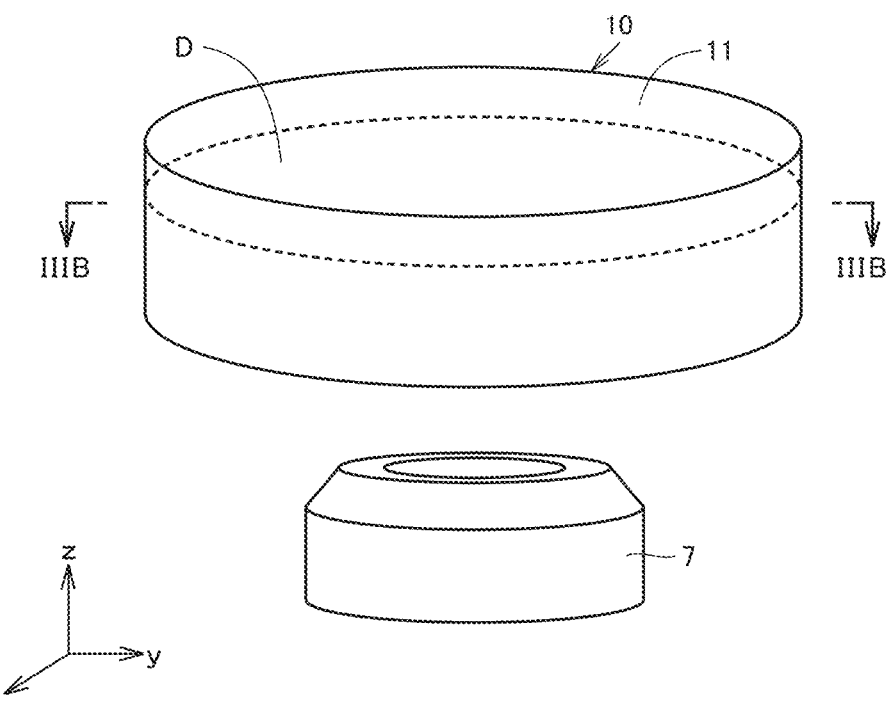
(B)
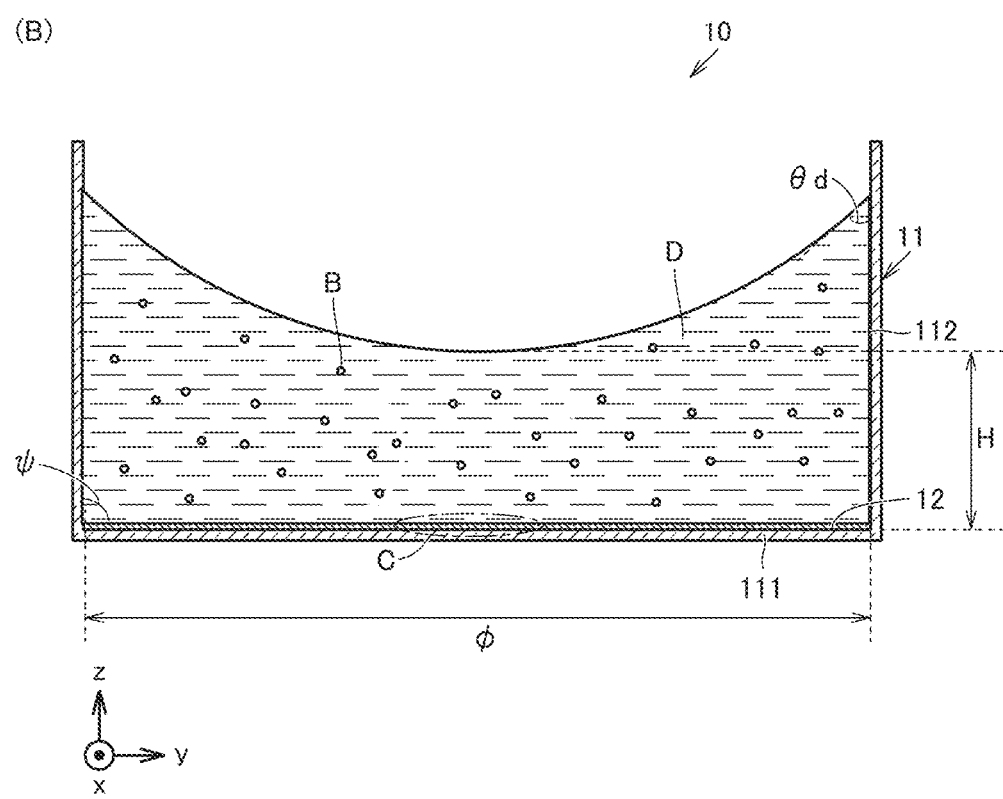

FIG.5      <COMPARATIVE EXAMPLE>
(A)
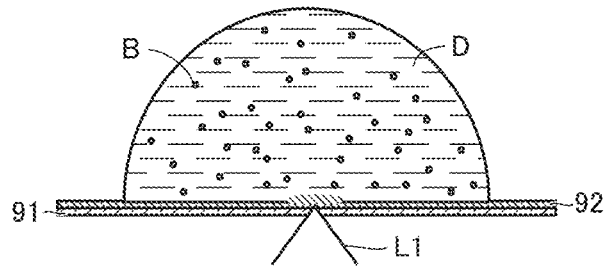
(B)
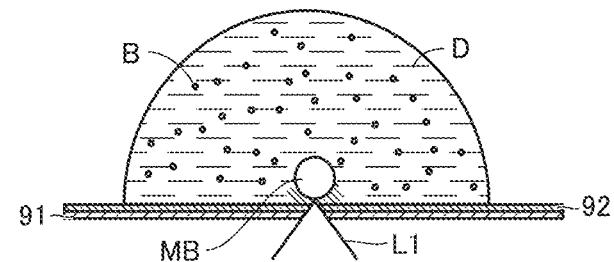
(C)
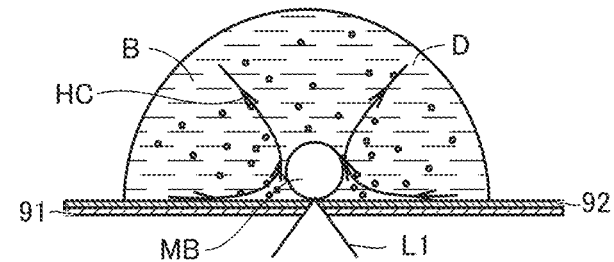
(D)
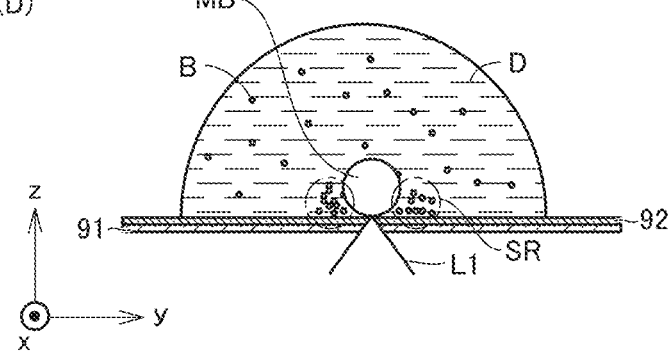

FIG. 7
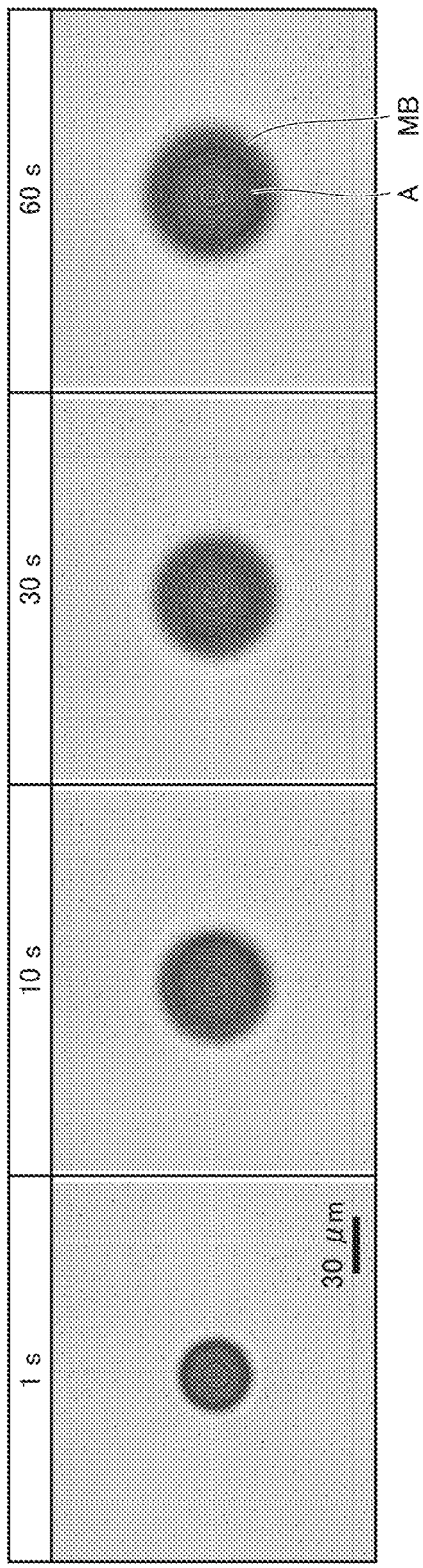
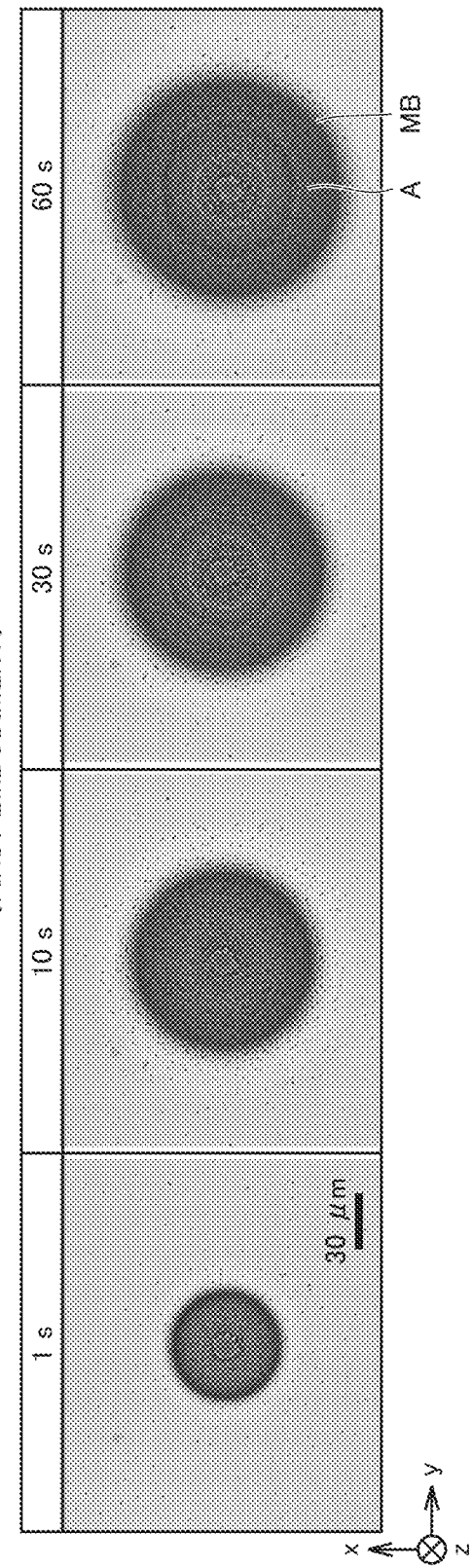

FIG.14  <ULTRASONIC TREATMENT PERFORMED>

FIG.15
(A) <ULTRASONIC TREATMENT NOT PERFORMED>
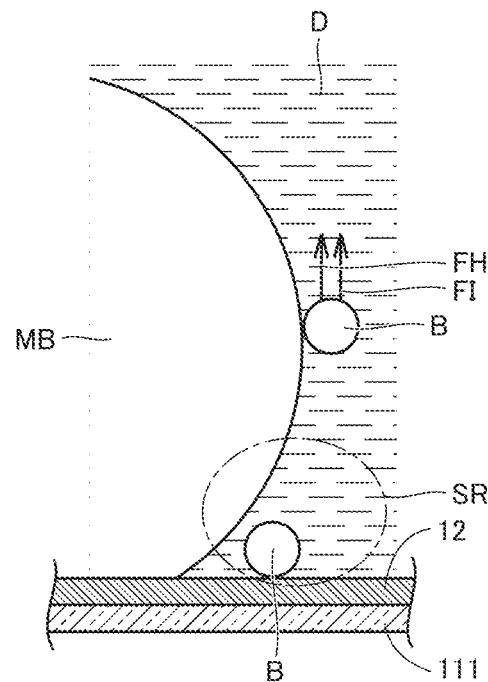
(B) <ULTRASONIC TREATMENT PERFORMED>
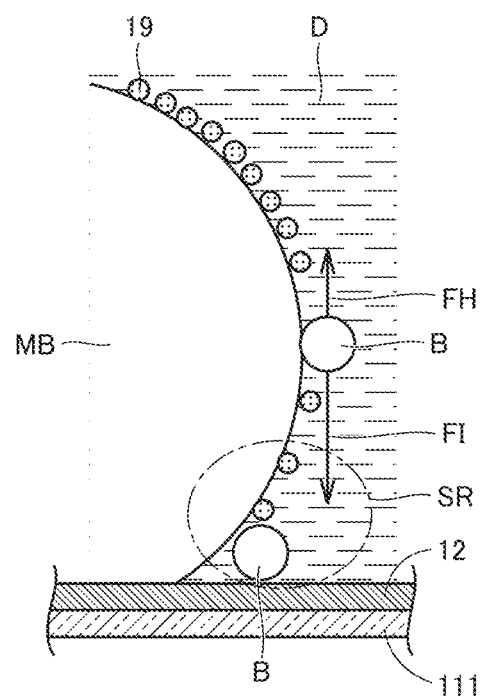

FIG.17 <SECOND EMBODIMENT>

FIG.18
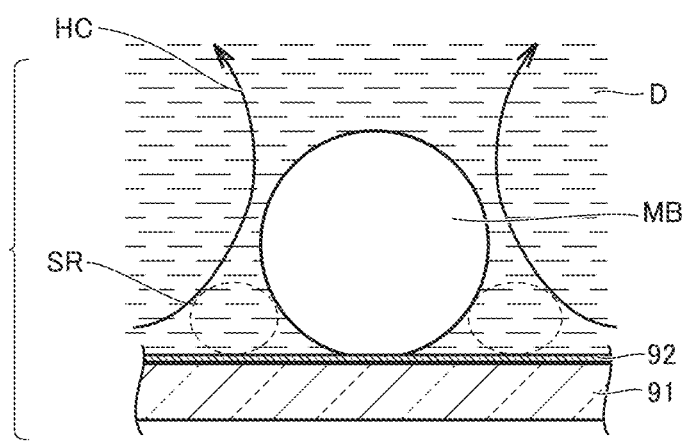
COMPARATIVE EXAMPLE (A)
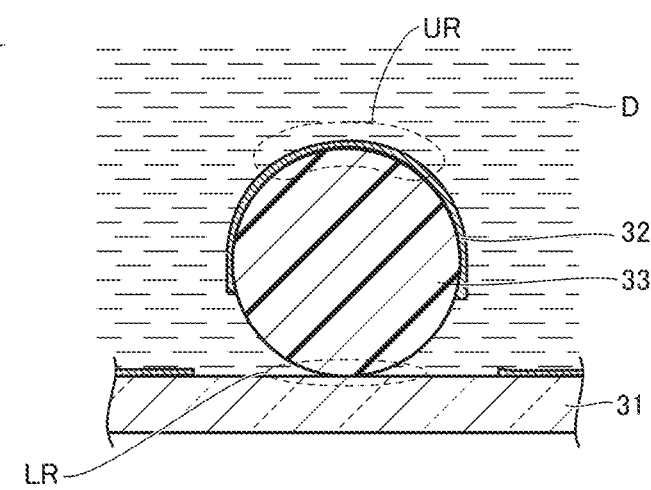
(B)
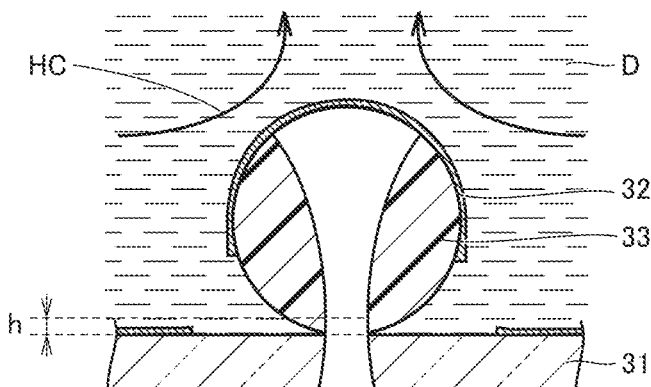
SECOND EMBODIMENT (C)

FIG.20 <BEAM WAIST HEIGHT h=0 μm>

FIG.24
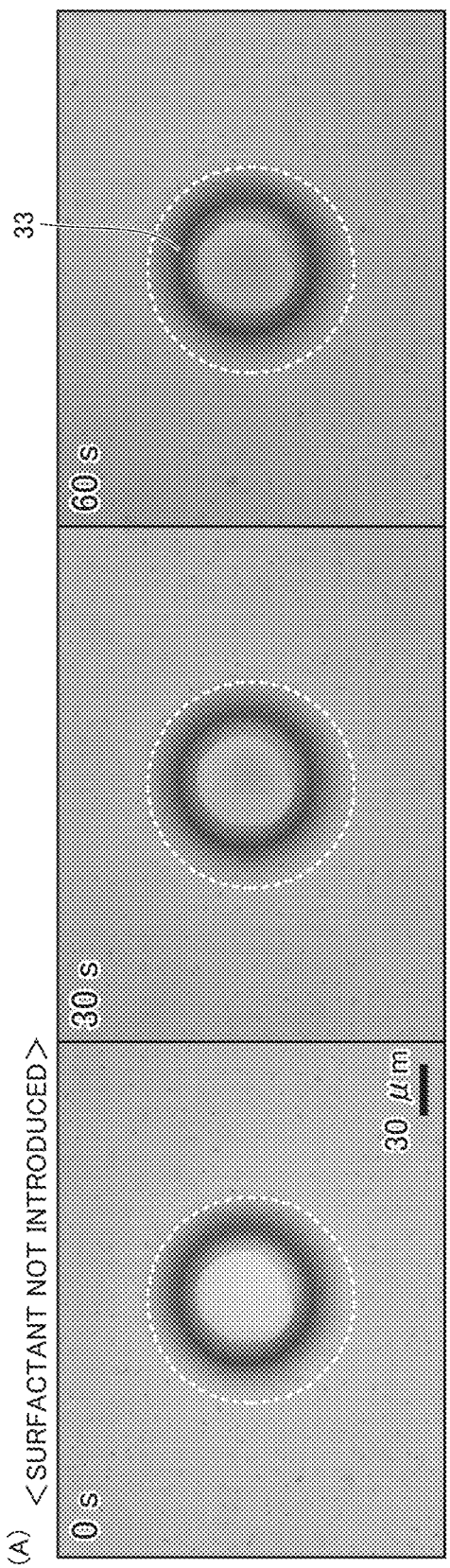
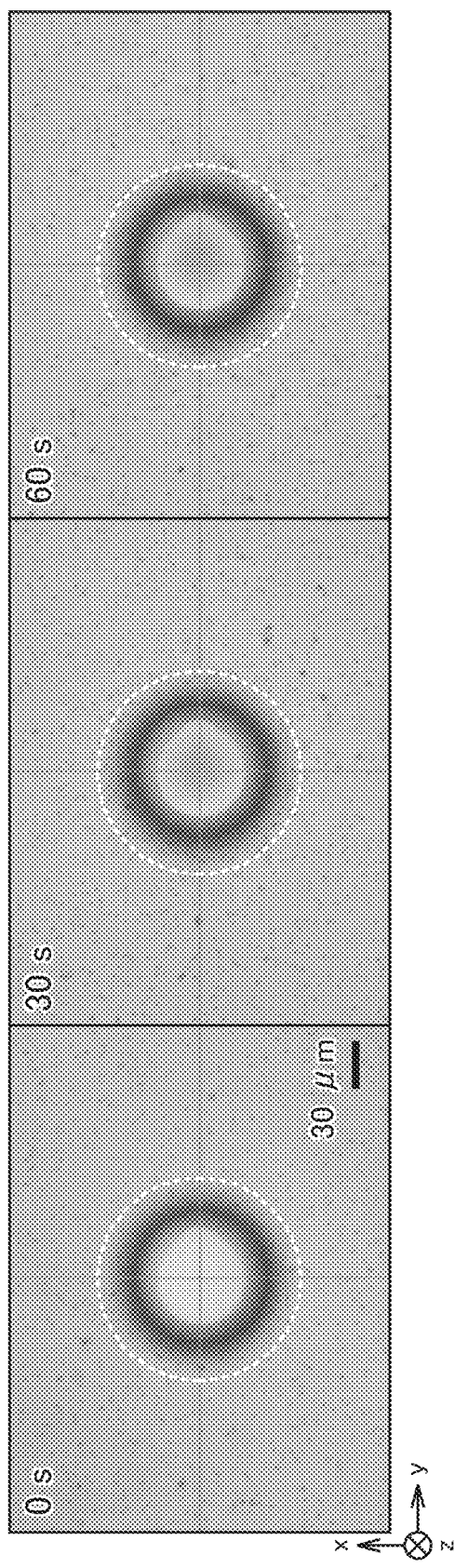

FIG.31  <FIRST MODIFICATION OF SECOND EMBODIMENT>

FIG.32 <SECOND MODIFICATION OF SECOND EMBODIMENT>

FIG.33
(A) <THIRD MODIFICATION OF SECOND EMBODIMENT>
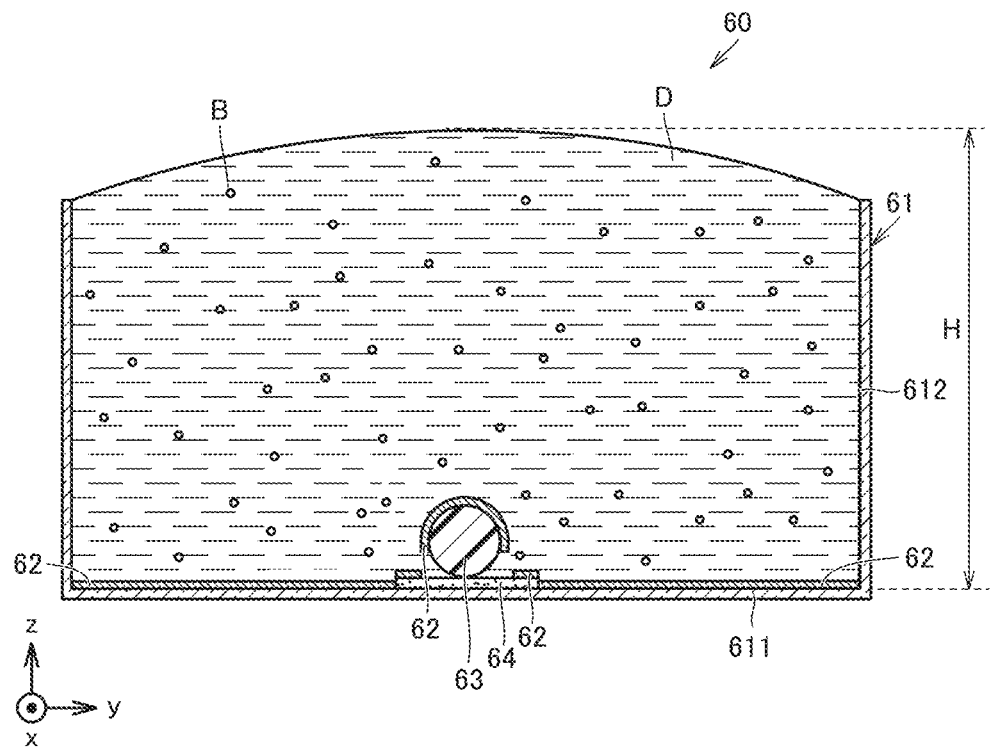
(B)
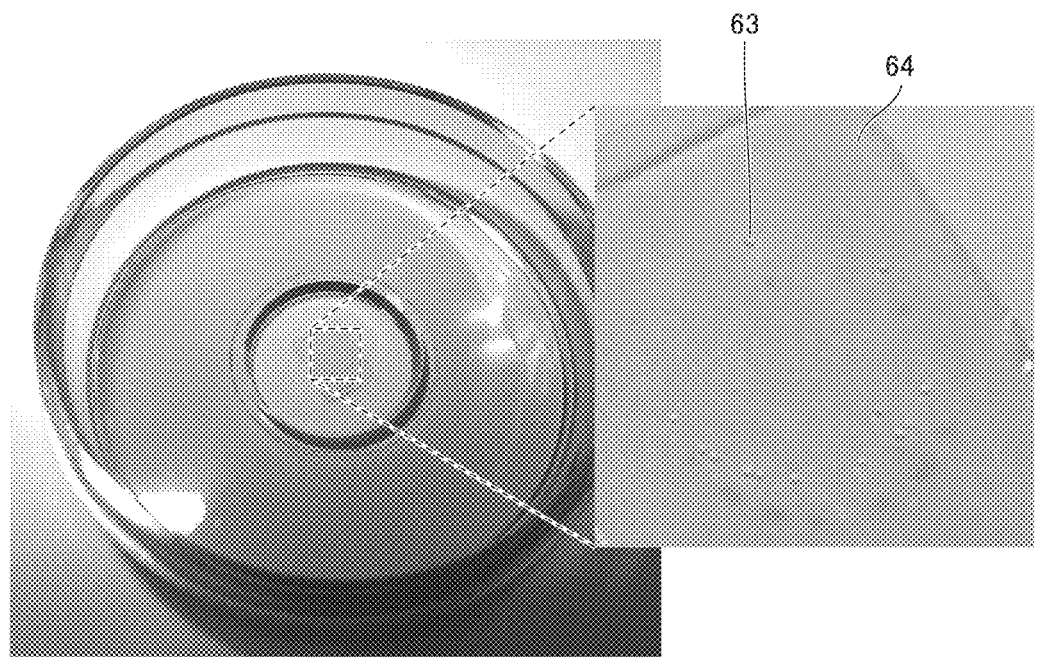

FIG.35 <THIRD EMBODIMENT>

FIG.36
(A)
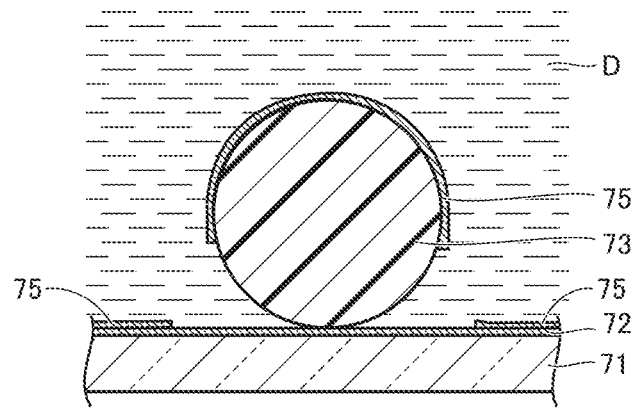
(B)
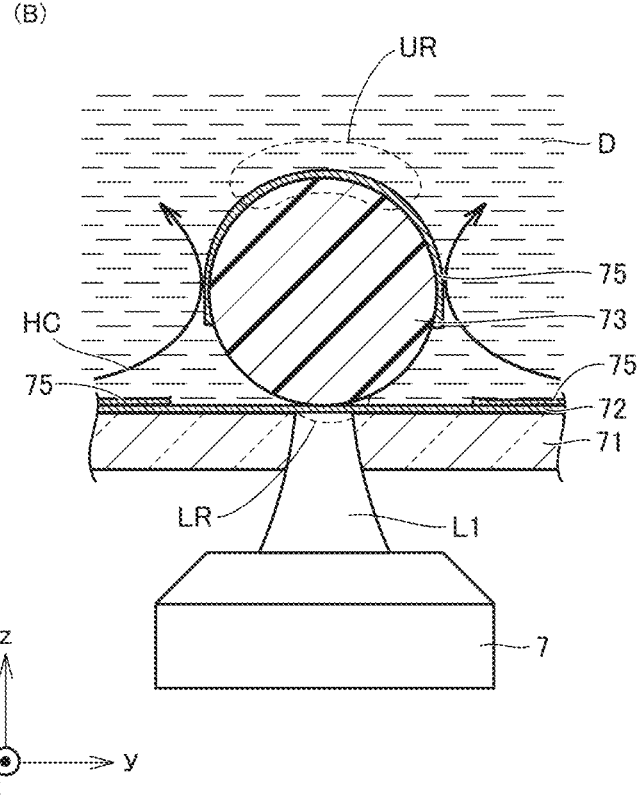

<MODIFICATION OF THIRD EMBODIMENT>

FIG.41
<TENTH SAMPLE>
(A)
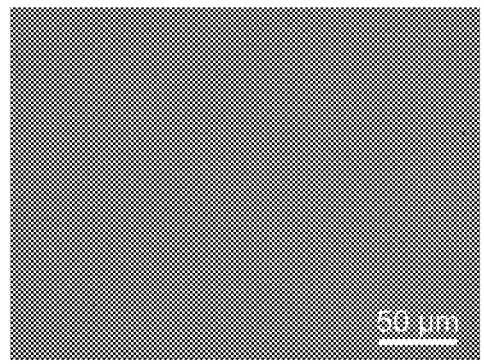
(B)
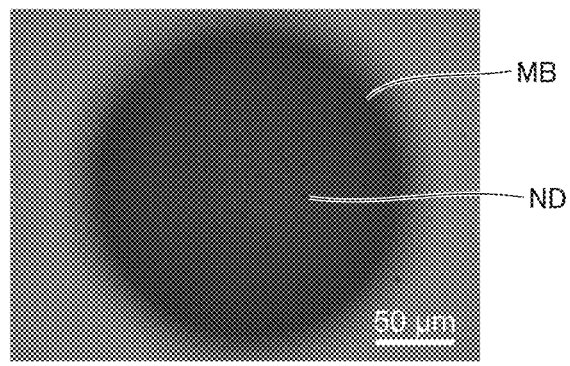
— MB
— ND
(C)
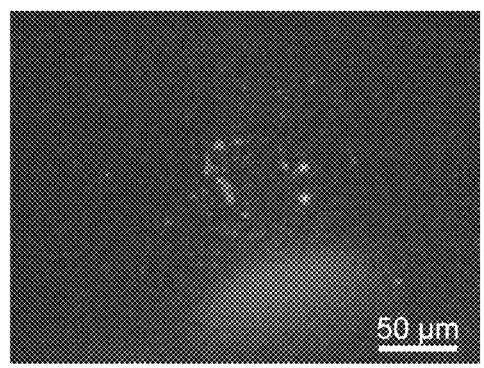

FIG.42
<ELEVENTH SAMPLE>
(A)
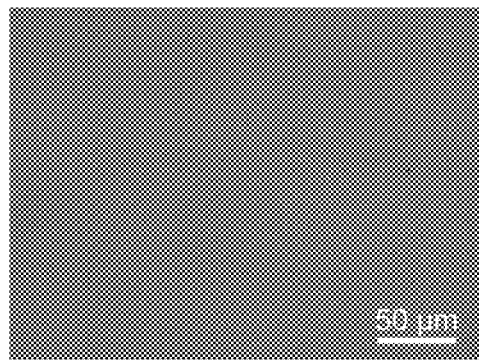
(B)
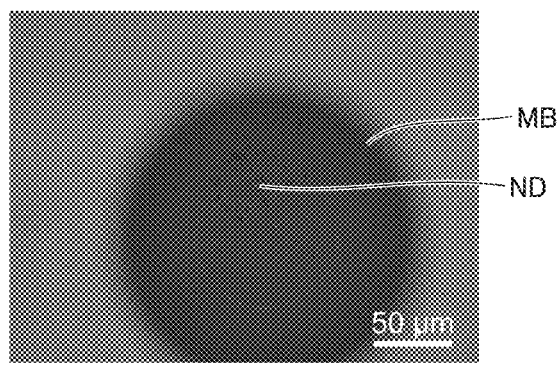
(C)
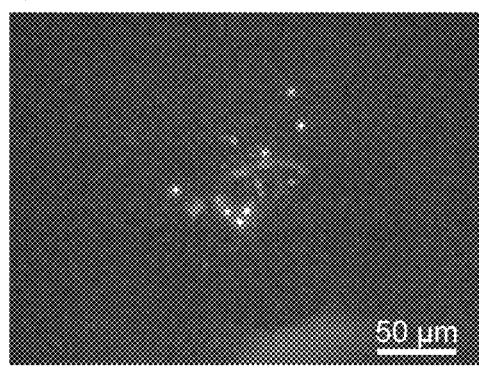

FIG.44 <THIRTEENTH SAMPLE>
(A)
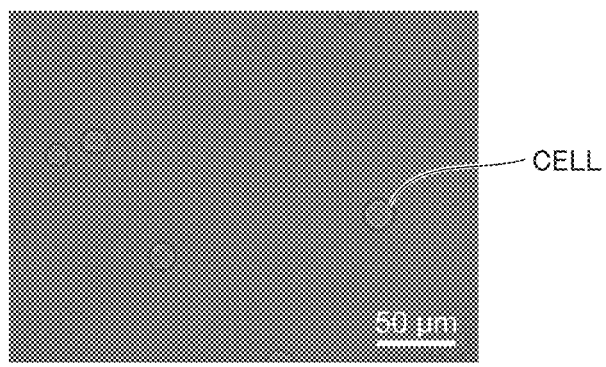
(B)
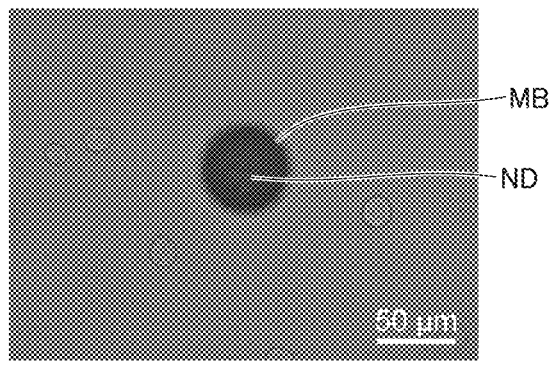
(C)
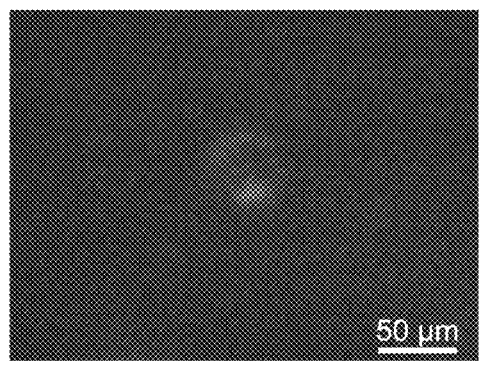
(D)
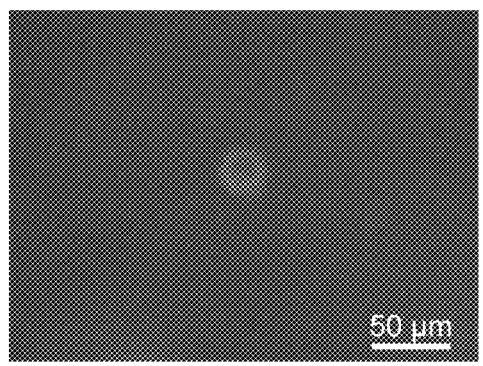

FIG.45  <THIRTEENTH SAMPLE>
(A)
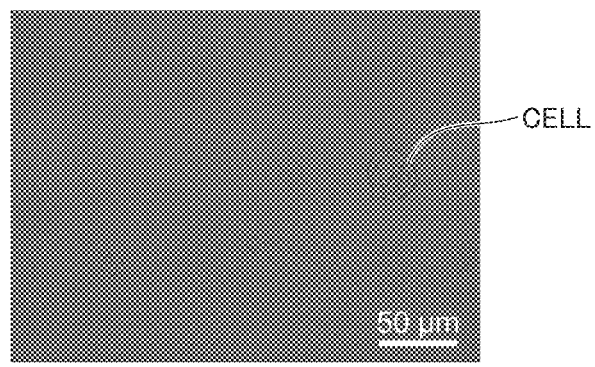
(B)
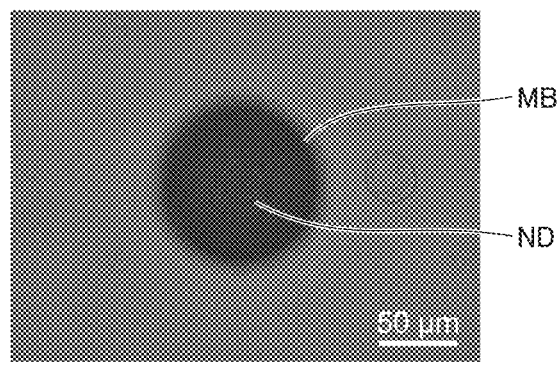
(C)
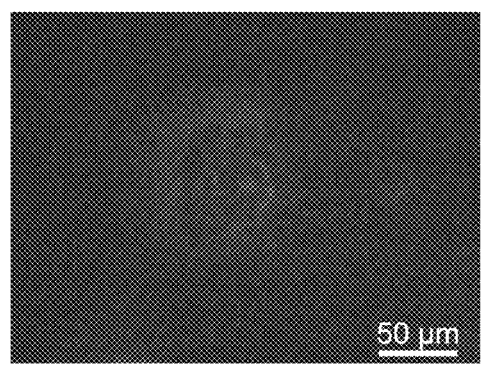
(D)
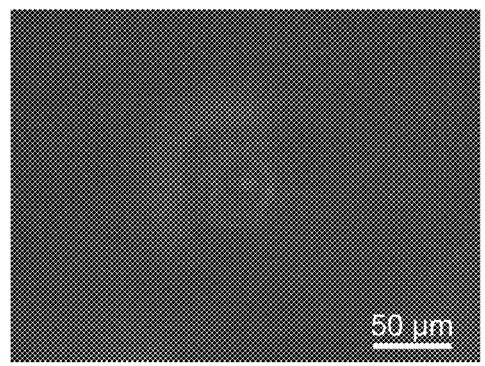

COLLECTING APPARATUS FOR MICROSCOPIC OBJECTS, COLLECTING CONTAINER USED IN COLLECTING APPARATUS, AND METHOD OF COLLECTING MICROSCOPIC OBJECTS

TECHNICAL FIELD

The present disclosure relates to a collecting apparatus for microscopic objects, a collecting container used in the collecting apparatus, and a method of collecting the microscopic objects, and more particularly to a technique for collecting a plurality of microscopic objects dispersed in a liquid.

BACKGROUND ART

There is a proposal about a technique for collecting microscopic objects such as particles or microorganisms in a targeted position by light irradiation. For example, WO2015/170758 (PTL 1) discloses a technique for collecting beads in a position irradiated with a laser beam (a laser spot) by irradiating a substrate with a laser beam. The substrate holds a liquid in which beads are dispersed.

More specifically, according to PTL 1, a gold thin film that converts light energy into thermal energy is formed on the substrate onto which a sample (a dispersion liquid in which a large number of beads are dispersed) is dropped. Thus, when the gold thin film is irradiated with a laser beam, light energy is converted into thermal energy to thereby heat the liquid, with the result that a temperature gradient occurs in the liquid. This produces a thermal convection in the liquid. By using such a thermal convection, beads can be collected in the vicinity of the laser spot (for example, see FIGS. 1 to 6 in PTL 1).

For the technique of collecting a plurality of microscopic objects dispersed in a liquid, it is desired to collect microscopic objects in a shorter time period, or to collect a larger number of microscopic objects, that is, to more highly efficiently collect microscopic objects.

The present disclosure has been made to solve the above-described problems. An object of the present disclosure is to provide a technique by which microscopic objects dispersed in a liquid can be highly efficiently collected.

SUMMARY OF INVENTION (1) A collecting apparatus for microscopic objects according to an aspect of the present disclosure is configured to collect microscopic objects having sizes ranging from a nanometer order to a micrometer order. The collecting apparatus for microscopic objects includes: a light source configured to emit light; and a container configured to hold a dispersion liquid in which the microscopic objects are dispersed. The container has a bottom surface and an inner side surface. A photothermal conversion member for converting the light from the light source into heat is formed on the bottom surface. Immersion wetting occurs at the inner side surface by the dispersion liquid when the inner side surface comes into contact with the dispersion liquid. The photothermal conversion member is configured to produce a thermal convection in the dispersion liquid by heating the dispersion liquid. The inner side surface is configured to produce a Marangoni convection at a gas-liquid interface as an interface between the dispersion liquid and gas around the dispersion liquid.

(2) Preferably, the dispersion liquid is an aqueous liquid. The inner side surface exhibits hydrophilicity. The container is configured to hold the dispersion liquid such that a meniscus is formed to be concave with respect to the gas-liquid interface.

(3) More preferably, the collecting apparatus for microscopic objects further includes a liquid-amount adjustment mechanism and a controller. The liquid-amount adjustment mechanism is configured to adjust an amount of the dispersion liquid held in the container. The controller is configured to control the liquid-amount adjustment mechanism such that a meniscus is formed to be concave with respect to the gas-liquid interface.

(4) Preferably, the bottom surface has an approximately circular shape. The photothermal conversion member is formed in a central region of the bottom surface.

(5) More preferably, the container is a glass bottom dish having an approximately cylindrical space defined by the inner side surface.

(6) Preferably, the container further includes a heat insulating spacer that is fixed onto the bottom surface and that is lower in thermal conductivity than the photothermal conversion member. The photothermal conversion member is formed on the heat insulating spacer. The light source is configured to irradiate the photothermal conversion member with the light that is within an absorption wavelength range of the photothermal conversion member and that is out of an absorption wavelength range of the heat insulating spacer.

(7) Preferably, the photothermal conversion member includes a first photothermal conversion layer and a second photothermal conversion layer. The first photothermal conversion layer is formed on the bottom surface. The container further includes a heat insulating spacer fixed onto the first photothermal conversion layer. The second photothermal conversion layer is formed on the heat insulating spacer. The heat insulating spacer is lower in thermal conductivity than the first photothermal conversion layer and the second photothermal conversion layer. The light source is configured to irradiate the first photothermal conversion layer and the second photothermal conversion layer with the light that is within an absorption wavelength range of each of the first photothermal conversion layer and the second photothermal conversion layer, and that is out of an absorption wavelength range of the heat insulating spacer.

(8) Preferably, the container further includes an adhesion member for fixing the heat insulating spacer.

(9) Preferably, the collecting apparatus for microscopic objects further includes an objective lens for condensing the light from the light source. The heat insulating spacer is larger in size than a diameter of a focal point of the light condensed by the objective lens.

(10) More preferably, the collecting apparatus for microscopic objects further includes a position adjustment mechanism. The position adjustment mechanism is configured to adjust a relative positional relation between the photothermal conversion member and the objective lens such that the focal point of the light condensed by the objective lens is located in a vicinity of a position at which the heat insulating spacer is fixed on the photothermal conversion member.

(11) A collecting container for microscopic objects according to another aspect of the present disclosure is used in a collecting apparatus for collecting microscopic objects having sizes ranging from a nanometer order to a micrometer order. The collecting container has a bottom surface on which a photothermal conversion member for converting light into heat is formed, and an inner side surface at which immersion wetting occurs by a dispersion liquid when the inner side surface comes into contact with the dispersion liquid, the microscopic objects being dispersed in the dispersion liquid. The photothermal conversion member is configured to produce a thermal convection in the dispersion liquid by heating the dispersion liquid when the photothermal conversion member is irradiated with the light within an absorption wavelength range of the photothermal conversion member in a state where the dispersion liquid is held inside the collecting container. The inner side surface is configured to produce a Marangoni convection at a gas-liquid interface as an interface between the dispersion liquid and gas around the dispersion liquid.

(12) Preferably, the dispersion liquid is an aqueous liquid. The inner side surface exhibits hydrophilicity. The collecting container is configured to hold the dispersion liquid such that a meniscus is formed to be concave with respect to the gas-liquid interface.

(13) Preferably, the bottom surface and the inner side surface form an angle that is equal to or greater than 45° and equal to or less than 135°.

(14) Preferably, the bottom surface has an approximately circular shape. The photothermal conversion member is formed in a central region of the bottom surface.

(15) Preferably, the collecting container is a glass bottom dish having an approximately cylindrical space defined by the inner side surface.

(16) Preferably, the collecting container further includes a heat insulating spacer that is fixed onto the bottom surface and that is lower in thermal conductivity than the photothermal conversion member. The photothermal conversion member is formed on the heat insulating spacer. The photothermal conversion member is irradiated with the light that is within the absorption wavelength range of the photothermal conversion member and that is out of an absorption wavelength range of the heat insulating spacer.

(17) Preferably, the photothermal conversion member includes a first photothermal conversion layer and a second photothermal conversion layer. The first photothermal conversion layer is formed on the bottom surface. The collecting container further includes a heat insulating spacer fixed onto the first photothermal conversion layer. The second photothermal conversion layer is formed on the heat insulating spacer. The heat insulating spacer is lower in thermal conductivity than the first photothermal conversion layer and the second photothermal conversion layer. The photothermal conversion member is irradiated with the light that is within the absorption wavelength range of each of the first photothermal conversion layer and the second photothermal conversion layer and that is out of an absorption wavelength range of the heat insulating spacer.

(18) More preferably, the collecting container for microscopic objects further includes an adhesion member for fixing the heat insulating spacer.

(19) A method of collecting microscopic objects according to a still another aspect of the present disclosure is to collect microscopic objects having sizes ranging from a nanometer order to a micrometer order. The method of collecting microscopic objects includes the first step to the third step. The first step is for holding, by a container, a dispersion liquid. The container has an inner side surface at which immersion wetting occurs by the dispersion liquid when the inner side surface comes into contact with the dispersion liquid. The second step is for, after the first step, irradiating a photothermal conversion member formed on a bottom surface of the container with light within an absorption wavelength range of the photothermal conversion member, to heat the dispersion liquid. The third step is for, by heating the dispersion liquid, producing a thermal convection in the dispersion liquid and producing a Marangoni convection at a gas-liquid interface as an interface between the dispersion liquid and gas around the dispersion liquid.

(20) Preferably, the method of collecting microscopic objects further includes the fourth step of, before the second step, dispersing amphiphilic substances into the dispersion liquid.

(21) Preferably, the method of collecting microscopic objects further includes, before the second step, introducing a surfactant into the dispersion liquid, the surfactant being for suppressing evaporation of the dispersion liquid from the gas-liquid interface.

(22) Preferably, the introducing includes introducing the surfactant into the dispersion liquid such that a concentration of the surfactant is within a prescribed range including a critical micelle concentration of the surfactant.

(23) Preferably, the method of collecting microscopic objects further includes the fifth step and the sixth step. The fifth step is for producing a microbubble on the bottom surface of the container by heating the dispersion liquid. The sixth step is for estimating a concentration of the microscopic objects in the dispersion liquid based on a total volume of the microscopic objects collected between the microbubble and the bottom surface of the container, a volume of each of the microscopic objects, and a heating time period during which the dispersion liquid is heated.

(24) Preferably, each of the microscopic objects is a nanodiamond.

According to the present disclosure, the collecting apparatus and the collecting method for collecting microscopic objects dispersed in a liquid allow highly efficient collection of microscopic objects.

BRIEF DESCRIPTION OF DRAWINGS

FIG. 2 is a diagram schematically showing the configuration of a collecting kit in a comparative example.

FIG. 3 is a diagram schematically showing the configuration of a collecting kit in the first embodiment.

FIG. 5 is a diagram for illustrating a collecting mechanism for bacteria in a comparative example.

FIG. 7 shows sequential images illustrating an example of a result of collecting bacteria (more specifically, *Staphylococcus aureus*).

FIG. 15 is a diagram for illustrating a collection facilitating mechanism by the ultrasonic treatment.

FIG. 18 is a diagram for more specifically illustrating the configuration around a heat insulating spacer shown in FIG. 17.

FIG. 24 is a diagram for illustrating an influence of a surfactant in the second embodiment.

FIG. 33 is a diagram schematically showing the configuration of a collecting kit in the third modification of the second embodiment.

FIG. 36 is a diagram for more specifically illustrating the configuration around a heat insulating spacer shown in FIG. 35.

FIG. 41 is a diagram for illustrating a result of collecting nanodiamonds in the tenth sample.

FIG. 42 is a diagram for illustrating a result of collecting nanodiamonds in the eleventh sample.

FIG. 44 is a diagram for illustrating a result of collecting nanodiamonds in the case of light irradiation at one position in the thirteenth sample.

FIG. 45 is a diagram for illustrating a result of collecting nanodiamonds in the case of light irradiation at another position in the thirteenth sample.

DESCRIPTION OF EMBODIMENTS

Figure 1:
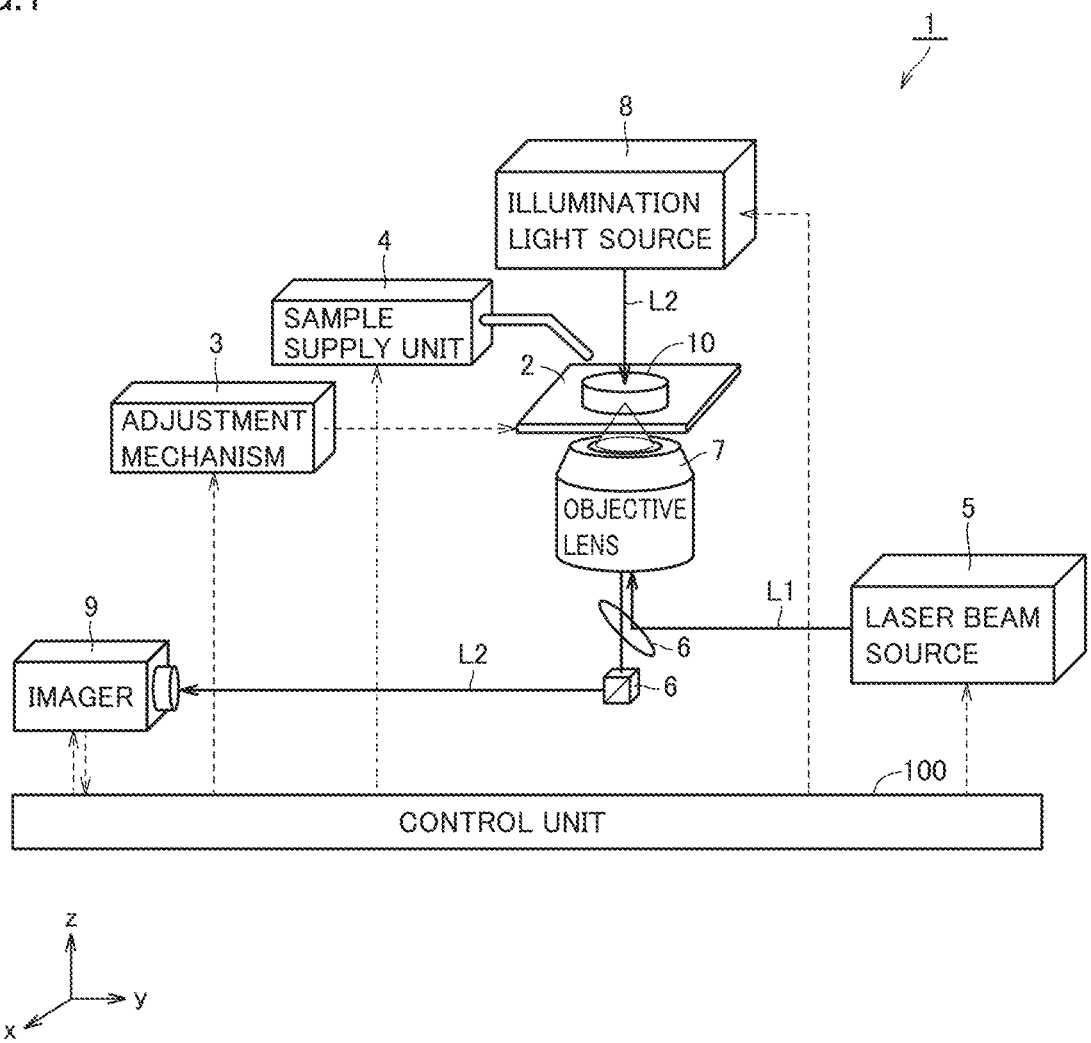
FIG. 1 is a diagram schematically showing the configuration of a collecting apparatus for bacteria according to the first embodiment.

The embodiments of the present disclosure will be hereinafter described in detail with reference to the accompanying drawings, in which the same or corresponding components are designated by the same reference characters, and the description thereof will not be repeated.

In the present disclosure, the term of a "microscopic object" means a substance having a size ranging from a nanometer order to a micrometer order. The shape of the microscopic object is not particularly limited, and may be a spherical shape, an elliptical sphere shape, a rod shape, and the like, for example. When the microscopic object has an elliptical sphere shape, at least one of the length in the minor axis direction and the length in the major axis direction of the elliptical sphere may be within the range from a nanometer order to a micrometer order. When the microscopic object has a rod shape, at least one of the rod width and the rod length may be within the range from a nanometer order to a micrometer order.

Examples of the microscopic object may be a metallic nanoparticle, a metallic nanoparticle assembly, a metallic nanoparticle assembly structure, a semiconductor nanoparticle, an organic nanoparticle, a resin bead, a particulate matter (PM), a nanodiamond, and the like. The "metallic nanoparticle" is a metallic particle having a size in the nanometer order. The "metallic nanoparticle assembly" is an assembly formed by aggregation of a plurality of metallic nanoparticles. The "metallic nanoparticle assembly structure" is a structure, for example, in which a plurality of metallic nanoparticles are fixed to the surface of a bead via an interacting site and spaced apart from each other at a distance equal to or less than the diameter of a metallic nanoparticle. The "semiconductor nanoparticle" is a semiconductor particle having a size in the nanometer order. The "organic nanoparticle" is a particle made of an organic compound having a size in the nanometer order. The "resin bead" is a particle made of a resin having a size ranging from the nanometer order to the micrometer order. The "PM" is a particulate matter having a size in the micrometer order. Examples of PM may be PM2.5 and a suspended particulate matter (SPM). The "nanodiamond" is a particle in the nanometer order, which has a crystal structure of a diamond.

Furthermore, the microscopic object may be a biologically originated substance (biological substance). More specifically, the microscopic object may include a cell, a microorganism (a bacterium, a fungus, and the like), a biopolymer (a protein, a nucleic acid, lipid, polysaccharides, and the like), an antigen (an allergen and the like), and a virus.

In the present disclosure, the "nanometer order" includes a range from 1 nm to 1000 nm (=1 μm). The "micrometer order" includes a range from 1 μm to 1000 μm (=1 mm). Thus, the expression of "from a nanometer order to a micrometer order" indicates the range from 1 nm to 1000 μm, but may typically indicate the range from several tens of nm to several hundreds of μm, preferably indicate the range from 100 nm to 100 μm, and more preferably indicate the range from 1 μm to several tens of μm.

In the present disclosure, "immersion wetting" means the state where, when a liquid and a solid (more specifically, a solid surface in the horizontal direction) come into contact with each other, a contact angle θ formed in the state where the liquid and the solid are stationary (the angle inside the liquid) is greater than 0° and less than 90°, that is, the state where spreading of liquid is stabilized at any contact angle θ of 0°<θ<90°. Immersion wetting may occur when a liquid is an aqueous liquid and the solid surface has hydrophilicity. Furthermore, immersion wetting may occur also when a liquid is an organic solvent and the solid surface has solvophilicity.

In the present disclosure, the "amphiphilic substance" means a substance having both a hydrophilic group and a hydrophobic group (or a lipophilic group and a lyophobic group). The amphiphilic substance includes a surfactant, an emulsifier, and a biopolymer (phospholipid, a membrane protein, and the like).

In the present disclosure, the "surfactant" means a substance that dissolves in at least one phase of a family and adsorbs to the interface with another phase in a certain orientation to form a monomolecular film.

In the present disclosure, the "light that is within an absorption wavelength range" means light that is within a wavelength range in which the photothermal conversion efficiency is equal to or greater than a prescribed value when a target object (for example, a photothermal conversion member that will be described later) is irradiated with the light. In addition, the "light that is out of an absorption wavelength range" means light that is within a wavelength range in which the photothermal conversion efficiency is less than a prescribed value (for example, approximately 0%) when a target object is irradiated with the light.

In the present disclosure, a "microbubble" is an air bubble having a size in the micrometer order.

First Embodiment

The first embodiment will be hereinafter described with regard to an example of the configuration for mainly collecting *Staphylococcus aureus* (simply referred to as "bacteria") as an example of the "microscopic object" according to the present disclosure.

In the following description, the x-direction and the y-direction represent a horizontal direction. The x-direction and the y-direction are orthogonal to each other. The z-direction represents a vertical direction. The direction of gravity extends downward in the z-direction. Upward in the z-direction is abbreviated as "upward" while downward in the z-direction is abbreviated as "downward".

<Entire Configuration of Collecting Apparatus>

FIG. 1 is a diagram schematically showing the configuration of a collecting apparatus 1 for bacteria according to the first embodiment. Collecting apparatus 1 includes a collecting kit 10, an XYZ-axis stage 2, an adjustment mechanism 3, a sample supply unit 4, a laser beam source 5, an optical component 6, an objective lens 7, an illumination light source 8, an imager 9, and a control unit 100.

Collecting kit 10 holds a sample. In the present embodiment, the sample is a liquid (a dispersion liquid) in which bacteria are dispersed. The detailed configuration of collecting kit 10 will be described with reference to FIG. 3. Collecting kit 10 is placed on XYZ-axis stage 2. Collecting kit 10 corresponds to a "collecting container" according to the present disclosure.

Adjustment mechanism 3 adjusts the relative positional relation between XYZ-axis stage 2 and objective lens 7 in response to a command from control unit 100. In the present embodiment, the position of objective lens 7 is fixed. Thus, the relative positional relation between XYZ-axis stage 2 and objective lens 7 is adjusted by adjusting the position of XYZ-axis stage 2 in the x-direction, the y-direction and the z-direction. As adjustment mechanism 3, for example, a drive mechanism (not shown) such as a servo motor and a focusing handle attached to a microscope can be used, but a specific configuration of adjustment mechanism 3 is not particularly limited. Adjustment mechanism 3 may be configured to allow adjustment of the position of objective lens 7. Adjustment mechanism 3 corresponds to the "position adjustment mechanism" according to the present disclosure.

Sample supply unit 4 supplies a dispersion liquid onto collecting kit 10 in response to the command from control unit 100. As sample supply unit 4, a dispenser can be used, for example. Sample supply unit 4 corresponds to the "liquid-amount adjustment mechanism" according to the present disclosure.

Laser beam source 5 emits, for example, a near-infrared laser beam L1 (for example, a wavelength of 1064 nm) in response to the command from control unit 100. The wavelength of laser beam L1 is not limited to the above as long as the wavelength is included in the absorption wavelength range of the material of thin film 12 (see FIG. 3), which will be described later. Laser beam source 5 corresponds to the "light source" according to the present disclosure.

Optical component 6 includes a mirror, a dichroic mirror, or a prism, for example. The optical system of collecting apparatus 1 is adjusted such that laser beam L1 from laser beam source 5 is guided to objective lens 7 by optical component 6.

Objective lens 7 condenses laser beam L1 from laser beam source 5. Collecting kit 10 is irradiated with the light beam condensed by objective lens 7. The term of "irradiate" used herein includes the case where laser beam L1 passes through collecting kit 10, that is, is not limited to the case where the beam waist of the light condensed by objective lens 7 is located inside collecting kit 10. In addition, optical component 6 and objective lens 7 can be incorporated in a main body of an inverted microscope or a main body of an upright microscope (each of which is not shown), for example.

In response to the command from control unit 100, illumination light source 8 emits white light L2 for illuminating the dispersion liquid inside collecting kit 10. As one example, a halogen lamp can be used as illumination light source 8. Objective lens 7 is used also for capturing white light L2 applied to collecting kit 10. White light L2 captured by objective lens 7 is guided to imager 9 by optical component 6.

In response to the command from control unit 100, imager 9 takes images of the dispersion liquid inside collecting kit 10 irradiated with white light L2, and then, outputs the taken images (a moving image or a still image) to control unit 100. Imager 9 may be a video camera including a charge coupled device (CCD) image sensor or a complementary metal oxide semiconductor (CMOS) image sensor.

Control unit (controller) 100 is a microcomputer that includes a central processing unit (CPU), a memory and an input/output port, each of which is not shown. Control unit 100 controls each of devices (sample supply unit 4, adjustment mechanism 3, laser beam source 5, illumination light source 8, and imager 9) inside collecting apparatus 1. Furthermore, control unit 100 can also subject the images taken by imager 9 to prescribed image processing.

In addition, the optical system of collecting apparatus 1 is not limited to the configuration shown in FIG. 1 as long as collecting kit 10 can be irradiated with laser beam L1 from laser beam source 5 and also white light L2 with which collecting kit 10 is irradiated can be captured into imager 9. For example, the optical system of collecting apparatus 1 may include an optical fiber and the like. Furthermore, adjustment mechanism 3, sample supply unit 4, illumination light source 8, and imager 9 are not indispensable components in collecting apparatus 1.

<Configuration of Collecting Kit>

Collecting apparatus 1 for bacteria according to the first embodiment is characterized by the configuration of collecting kit 10. In order to allow easy understanding of such characteristics, the configuration of collecting kit 10 will be described below as compared with the configuration of a collecting kit 90 in a comparative example. The configurations other than that of collecting kit 90 of the collecting apparatus according to the comparative example are basically the same as the corresponding configurations of collecting apparatus 1 according to the first embodiment, and therefore, the detailed description thereof will not be repeated.

FIG. 2 is a diagram schematically showing the configuration of collecting kit 90 in the comparative example. FIG. 2(A) shows a perspective view of collecting kit 90. FIG. 2(B) shows a cross-sectional view of collecting kit 90 taken along a line IIB-IIB in FIG. 2(A). FIG. 3 is a diagram schematically showing the configuration of a collecting kit 10 in the first embodiment. FIG. 3(A) shows a perspective view of collecting kit 10. FIG. 3(B) shows a cross-sectional view of collecting kit 10 taken along a line IIIB-IIIB in FIG. 3(A). It is to be noted that FIGS. 2 and 3 do not show XYZ-axis stage 2.

Referring to FIGS. 2(A) and 2(B), collecting kit 90 includes a substrate 91 and a thin film 92. Substrate 91 is formed of a material that does not influence photothermal conversion (described later) of laser beam L1 by thin film 92 and that is transparent to white light L2. Examples of such a material may be quartz, silicon, and the like. In the comparative example, a glass substrate (a cover glass) is used as substrate 91.

Referring to FIGS. 3(A) and 3(B), collecting kit 10 includes a container 11 and a thin film 12. Container 11 has a bottom surface 111 and an inner side surface 112. Bottom surface 111 of container 11 is made of a material that does not influence photothermal conversion of laser beam L1 by thin film 12 and that is transparent to white light L2, as in the case of substrate 91. Inner side surface 112 of container 11 is formed using a material exhibiting hydrophilicity.

In the first embodiment, container 11 is a glass bottom dish having a cylindrical-shaped internal space (a well) in which a dispersion liquid D is held. In this case, glass as a material of bottom surface 111 and inner side surface 112 of container 11 usually exhibits hydrophilicity. However, formation of thin film 12 on bottom surface 111 causes bottom surface 111 to exhibit hydrophobicity. In other words, inner side surface 112 of container 11 exhibits high hydrophilicity as compared with bottom surface 111.

Although glass is a material usually exhibiting hydrophilicity, it may be less hydrophilic (or may be hydrophobic) depending on the situation where the glass is placed (the storage state and the like). Thus, it is desirable to subject inner side surface 112 of container 11 to a hydrophilic treatment. Specifically, inner side surface 112 of container 11 can be washed with acetone or the inner surface of container 11 can be plasma-etched.

On the other hand, the material of the outer side surface of container 11 is not particularly limited, but may exhibit any of hydrophilicity and repellency. Furthermore, the outer side surface of container 11 may absorb laser beam L1 or may not allow white light L2 to pass therethrough.

Since thin film 12 and thin film 92 are basically the same, thin film 12 will be representatively described below. Thin film 12 absorbs laser beam L1 from laser beam source 5 and converts light energy into thermal energy. It is preferable that thin film 12 is made of a material achieving a high photothermal conversion efficiency in the wavelength range of laser beam L1 (in the near-infrared range in the present embodiment). In the first embodiment, a gold thin film having a thickness (film thickness) in the nanometer order is formed as thin film 12. A gold thin film can be formed using known methods such as sputtering or electroless plating.

When thin film 12 is a gold thin film, the free electrons on the surface of the gold thin film form surface plasmon and are oscillated by laser beam L1. Thereby, polarization occurs. The energy of this polarization is converted into energy of lattice vibrations by the Coulomb interaction between the free electrons and the atomic nuclei. As a result, the gold thin film generates heat. In the following, this effect will also be referred to as a "photothermal effect".

In the first embodiment, the photothermal effect is achieved using a near-infrared light with a wavelength of 1064 nm, but light with a wavelength close to the surface plasmon resonance wavelength of the gold thin film (the wavelength existing in the wavelength range of visible light of 400 nm to 800 nm in air or in water) may be used. Thereby, more heat can be generated even by laser beam L1 of the same intensity (laser beam intensity will be hereinafter also referred to as a "laser output").

Furthermore, the material of thin film 12 is not limited to gold, but may be a metal element other than gold that may produce a photothermal effect (for example, silver), a metallic nanoparticle assembly structure (for example, a structure made of gold nanoparticles or silver nanoparticles), or the like. Alternatively, thin film 12 may be made of a material other than metal exhibiting a high light absorption rate in the wavelength range of laser beam L1. Such a material may be a material close to a black body (for example, a carbon nanotube black body). The thickness of thin film 12 is determined in terms of design or experimentally in consideration of the laser output, and of the absorption wavelength range and the photothermal conversion efficiency of the material of thin film 12. Thin film 12 corresponds to the "photothermal conversion member" according to the present disclosure.

The liquid held inside container 11 in the first embodiment and the liquid dropped onto substrate 91 in the comparative example each are dispersion liquid D in which bacteria B are dispersed in an aqueous dispersion medium (for example, ultrapure water). In this case, dispersion liquid D dropped onto substrate 91 has a semielliptical sphere shape, as shown in FIGS. 2(A) and 2(B). In contrast, inner side surface 112 of container 11 is hydrophilic to the dispersion liquid held inside container 11. Accordingly, immersion wetting occurs at inner side surface 112 by dispersion liquid D. Then, at inner side surface 112, a meniscus is formed to be concave with respect to the gas-liquid interface between dispersion liquid D and the gas therearound, as shown in FIG. 3(B). When inner side surface 112 extends in the vertical direction, a dynamic contact angle θd formed between dispersion liquid D and inner side surface 112 is greater than 0° and less than 90° in the example shown in FIG. 3(B). However, it is noted for confirmation that the "contact angle" in the present disclosure means a value measured in the state where a liquid and a solid remain stationary when the liquid comes into contact with the horizontal solid surface as described above, but the "contact angle" is not necessarily the same as dynamic contact angle θd.

Objective lens 7 is disposed, for example, below bottom surface 111 of container 11 and condenses laser beam L1 from below. Dispersion liquid D above objective lens 7 is irradiated with the condensed light. It is preferable that the position irradiated with laser beam L1 (a laser spot) is, for example, in a central region C of circular bottom surface 111 of dispersion liquid D. Furthermore, it is preferable that the position of the focal point of laser beam L1 in the vertical direction (the beam waist) is in the vicinity of the solid-liquid interface between dispersion liquid D and bottom surface 111 of container 11. In the measurement result described later, images of the laser spot are taken by imager 9 from above. Although container 11 in the first embodiment has been described above, the same is applied as well to substrate 91 in the comparative example.

In the following description, the height of the gas-liquid interface in central region C of bottom surface 111 of container 11 (that is, the position of the laser spot) will be defined as H, and the diameter (the inner diameter) of container 11 will be defined as φ. FIG. 3(B) shows an example in which thin film 12 is formed on the entire bottom surface 111, but thin film 12 may be partially formed on central region C of bottom surface 111.

Furthermore, in the example shown in FIG. 3(B), inner side surface 112 extends at a right angle to bottom surface 111, but an angle Ψ formed between bottom surface 111 and inner side surface 112 (that is, angle Ψ formed between central region C of bottom surface 111 and inner side surface 112) may be an acute angle or an obtuse angle. Angle Ψ can be selected in accordance with the shape of the meniscus formed at inner side surface 112. However, when angle Ψ is excessively large, a concave meniscus is less likely to be formed at inner side surface 112. This can be understood from the fact that, as angle Ψ is increased, container 11 ultimately becomes a flat plane (that is, becomes substrate 91 as in the comparative example). Angle Ψ is typically in the range of 30° to 150° and preferably in the range of 45° to 135°.

<Collecting Flow>

Figure 4:
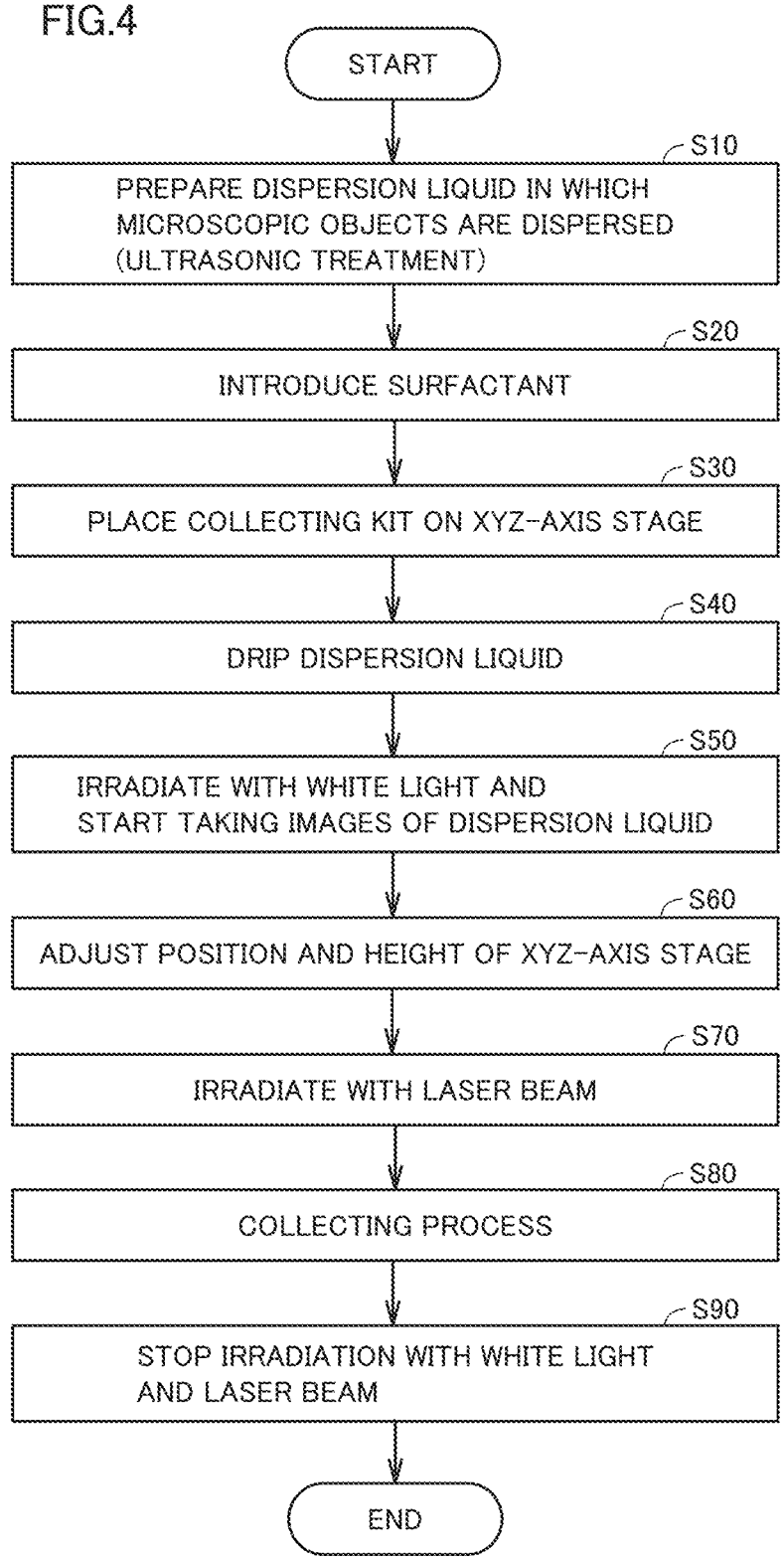
FIG. 4 is a flowchart illustrating a method of collecting bacteria in the first embodiment.

FIG. 4 is a flowchart illustrating a method of collecting bacteria B in the first embodiment. Each of the steps included in this flowchart is implemented basically through software processing by control unit 100, but may be partially or entirely implemented by hardware (an electric circuit) fabricated inside control unit 100. According to the collecting method for bacteria B in the comparative example, the processes other than a collecting process (a process in step S80) described later are the same as those in the collecting method for bacteria B shown in FIG. 4.

Referring to FIGS. 1 and 4, in step S10, dispersion liquid D in which bacteria B are dispersed is prepared. It is preferable that dispersion liquid D is subjected to an ultrasonic treatment for further dispersing the amphiphilic substances, which will be described later in detail.

In step S20, a surfactant is introduced into dispersion liquid D prepared in step S10. It is to be noted that this process is not indispensable, but is performed in the second modification of the second embodiment in the measurement example disclosed in the present specification (see FIGS. 24 and 25). The details of this process will also be described later. Dispersion liquid D prepared in steps S10 and S20 is stored in sample supply unit 4.

In step S30, control unit 100 causes collecting kit 10 (container 11) to be placed on XYZ-axis stage 2. This process can be implemented, for example, by a feed mechanism (not shown) of container 11.

In step S40, control unit 100 controls sample supply unit 4 to cause dispersion liquid D to be dropped such that an appropriate amount of dispersion liquid D is held inside container 11. An extremely small amount of dispersion liquid D, for example, of about several tens of μL to several hundreds of μL may be dropped or a larger amount of dispersion liquid D may be dropped. However, in the first embodiment, the amount of dispersion liquid D to be dropped is determined such that a concave meniscus is formed as shown in FIG. 3(B). Adjustment of the amount of dispersion liquid D to be dropped from sample supply unit 4 corresponds to adjustment of a height H of the gas-liquid interface and the shape of the gas-liquid interface (the shape of meniscus), and the technical meaning thereof will be described later.

In step S50, control unit 100 controls illumination light source 8 to emit white light L2 to be applied to dispersion liquid D inside container 11, and also controls imager 9 to start taking images of dispersion liquid D.

In step S60, control unit 100 controls adjustment mechanism 3 such that an appropriate position of container 11 is irradiated with laser beam L1 from laser beam source 5, thereby adjusting the position of XYZ-axis stage 2 in the horizontal direction. This position adjustment can be implemented, for example, by extracting the outer shape pattern of container 11 from the images taken by imager 9, using the image processing technique for pattern recognition. Furthermore, the position of the beam waist in the up-down direction (a height h, which will be described later) is known from the wavelength of laser beam L1 and the specifications (magnification and the like) of objective lens 7. Therefore, by adjusting the position of XYZ-axis stage 2 in the up-down direction, the beam waist can be positioned at the targeted height inside container 11.

In step S70, control unit 100 controls laser beam source 5 to start irradiation with laser beam L1 (which will be hereinafter also abbreviated as "light irradiation"). Laser beam L1 from laser beam source 5 is condensed by objective lens 7, and the condensed light is applied to thin film 12 formed at least on central region C of bottom surface 111 of container 11.

In step S80, a "collecting process" for collecting bacteria B is implemented. The details of this process will be described later.

In step S90, control unit 100 controls laser beam source 5 to stop irradiation of container 11 with light. Thereby, a series of processes ends.

It is to be noted that the process in step S50 is performed for observing dispersion liquid D, but is not indispensable for collecting bacteria B. Thus, bacteria B can be collected even when the flowchart not including the process in step S50 is performed.

<Collecting Mechanism>

Then, the collecting mechanism for bacteria B in the collecting process in step S80 will be described in the order of the comparative example and the first embodiment.

FIG. 5 is a diagram for illustrating a collecting mechanism for bacteria B in the comparative example. As shown in FIG. 5(A), when light irradiation is started, the portion in the vicinity of the laser spot is locally heated by the photothermal effect of thin film 92 at the laser spot. As a result, dispersion liquid D in the vicinity of the laser spot is boiled to thereby produce a microbubble MB at the laser spot (see FIG. 5(B)). Microbubble MB grows over time.

The temperature of dispersion liquid D is higher at the position closer to the laser spot. In other words, a temperature gradient occurs in dispersion liquid D by light irradiation. Due to this temperature gradient, a regular thermal convection (buoyancy convection) steadily occurs in dispersion liquid D (see FIG. 5(C)). The thermal convection is once directed toward microbubble MB and thereafter directed away from microbubble MB, as indicated by HC.

The reason why a thermal convection occurs in this way can be explained as below. Specifically, dispersion liquid D located above the region including microbubble MB is relatively diluted by heating, and thereby rises by buoyancy. Accordingly, a relatively low-temperature liquid existing in the horizontal direction of microbubble MB flows toward microbubble MB.

Bacteria B are carried through the thermal convection toward microbubble MB, so that bacteria B are collected in the vicinity of the laser spot. More specifically, a region in which the flow rate of the thermal convection is approximately zero (which will be hereinafter referred to as a "stagnation region") SR is produced between microbubble MB and the upper surface of thin film 92. Bacteria B carried through the thermal convection are stagnated in stagnation region SR and collected therein (see FIG. 5(D)). Then, when light irradiation is stopped, the thermal convection becomes weaker and finally stops.

Figure 6:
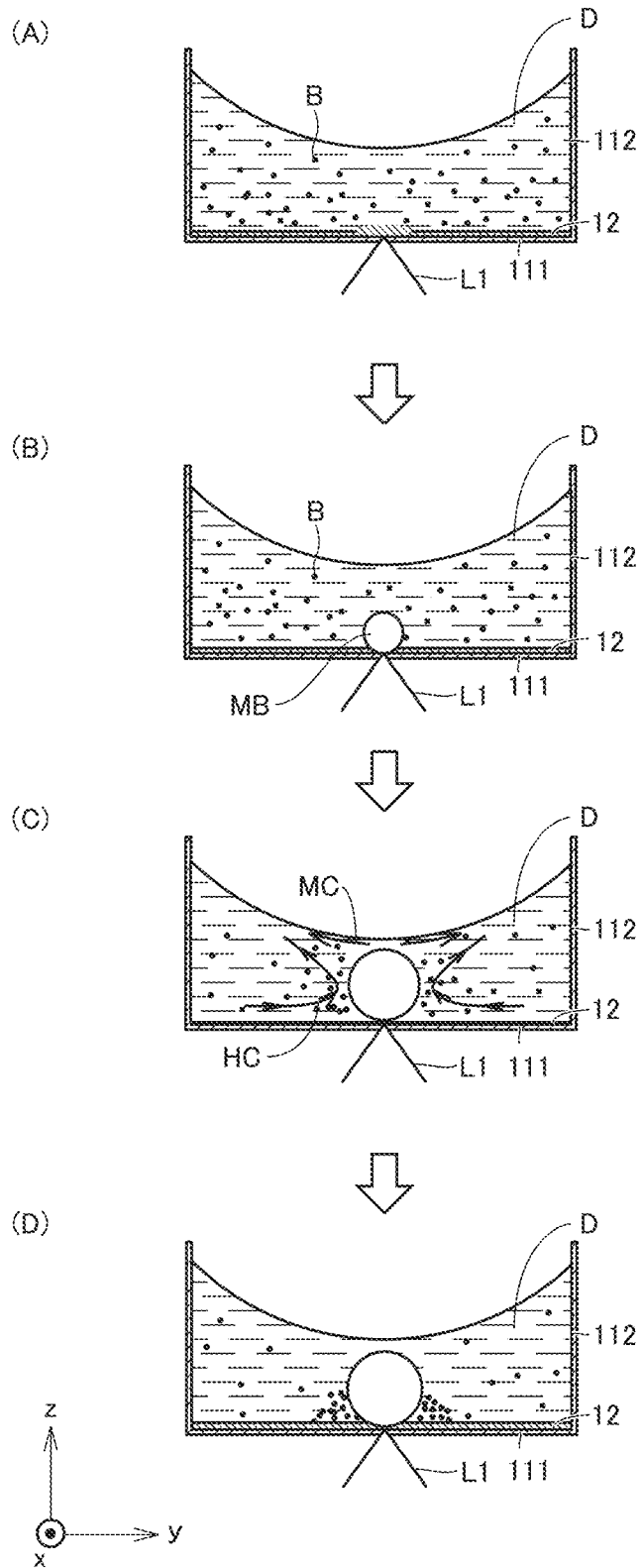
FIG. 6 is a diagram for illustrating a collecting mechanism for bacteria in the first embodiment.

FIG. 6 is a diagram for illustrating a collecting mechanism for bacteria B in the first embodiment. When light irradiation is started, the area in the vicinity of the laser spot is locally heated by the photothermal effect of thin film 12 at the laser spot (see FIG. 6(A)), as in the comparative example. In accordance with heating, dispersion liquid D in the vicinity of the laser spot is boiled, and then, microbubble MB occurs at the laser spot and grows over time (see FIG. 6(B)).

Due to the temperature gradient in dispersion liquid D caused by light irradiation, a thermal convection (indicated by HC) occurs in dispersion liquid D (see FIG. 6(C)).

Also in the first embodiment, a concave gas-liquid interface is formed. Thus, the distance between the laser spot and the gas-liquid interface located thereabove is relatively narrow. Accordingly, the temperature of the gas-liquid interface above the laser spot is more likely to be higher than the temperatures in other regions of the gas-liquid interface. Therefore, the amount of the dispersion medium evaporated from the gas-liquid interface is relatively increased above the laser spot. The flow of dispersion liquid D (not shown) for compensating for this evaporated dispersion medium mainly occurs from microbubble MB toward the gas-liquid interface (that is, upward). This flow accelerates the above-mentioned thermal convection.

Furthermore, in the first embodiment, a Marangoni convection (indicated by MC) occurs at the gas-liquid interface due to the gradient of the interfacial tension at the gas-liquid interface. More specifically, a concave meniscus is formed at inner side surface 112 in the first embodiment. In such a case, according to the Laplace's law (Young-Laplace equation), the interfacial tension at the gas-liquid interface in the vicinity of inner side surface 112 is greater than the interfacial tension at the gas-liquid interface above central region C of bottom surface 111. Thus, dispersion liquid D above central region C having a relatively small interfacial tension is pulled closer to the vicinity of inner side surface 112 having a relatively large interfacial tension. Thereby, a Marangoni convection occurs.

As described above, the thermal convection occurring at the gas-liquid interface flows in the direction away from microbubble MB. Thus, at the gas-liquid interface, the thermal convection and the Marangoni convection flow in the same direction from above central region C toward inner side surface 112 of container 11. Accordingly, the thermal convection and the Marangoni convection strengthen against each other at the gas-liquid interface, so that the flow rate of dispersion liquid D rises as compared with the comparative example. Since dispersion liquid D circulates through container 11, the flow rate in dispersion liquid D (the flow rate of the flow toward microbubble MB) also rises as the flow rate of dispersion liquid D at the gas-liquid interface rises. Accordingly, the moving speed of bacteria B is accelerated, so that bacteria B can be collected in a shorter time period. Alternatively, the amount of bacteria B collected (the collected number) in a fixed time period can be increased. In other words, bacteria B can be highly efficiently collected (see FIG. 6(D)).

Although not shown, a Marangoni convection resulting from the temperature gradient caused by light irradiation may occur also in the vicinity of microbubble MB. More specifically, in general, the interfacial tension is smaller as the interface temperature is higher. Thus, in a region of the surface (the gas-liquid interface) of microbubble MB that is in the vicinity of the laser spot, the interfacial tension is smaller than that in the region located at some distance from the laser spot. Therefore, in the vicinity of the surface of microbubble MB, a Marangoni convection may occur in the direction away from the laser spot. This Marangoni convection may occur also in the configuration of the comparative example.

Furthermore, as height H of the gas-liquid interface (see FIG. 3(B)) is lower (that is, the liquid depth is shallower), the influence of the thermal convection is smaller while the influence of the Marangoni convection is larger. In contrast, as height H of the gas-liquid interface is higher, the influence of the Marangoni convection is smaller while the influence of the thermal convection is larger. Also, an excessively large diameter $\phi$ of container 11 leads to a gentle gradient of the interfacial tension by a meniscus, and also leads to a smaller influence of the Marangoni convection. Accordingly, height H of the gas-liquid interface and diameter $\phi$ of container 11 are set as appropriate by experiments or simulations in accordance with: the property of the microscopic object as a target to be collected (size, shape, mass, density, and the like); the property of the dispersion medium (surface tension, density, viscosity, and the like); and wettability of inner side surface 112 of container 11 to the dispersion medium (the degree of hydrophilicity/hydrophobicity, and the like).

Furthermore, it is preferable that the space inside container 11 in which dispersion liquid D is held, that is, the space defined by inner side surface 112, has a cylindrical shape. When the space defined by inner side surface 112 has a cylindrical shape, a thermal convection and a Marangoni convection at the gas-liquid interface occur in axial symmetry with respect to the central axis of the cylindrical shape. Thereby, the regularity of each of the thermal convection and the Marangoni convection is enhanced, with the result that the efficiency of collecting bacteria B is improved. The same is applied as well to the case where the shape of the space defined by inner side surface 112 is a conical shape, a truncated cone shape, a hemispherical shape, or a spindle shape. The shape of the space defined by inner side surface 112 is not limited to the axially-symmetrical shape, but for example may be a prism shape, a pyramid shape, a truncated pyramid shape, or the like. In addition, the external shape of container 11 may be any shape as long as no influence is exerted upon the internal shape of container 11 (the shape of the space defined by inner side surface 112).

<Result of Collecting Bacteria>

First, the detailed conditions for collecting bacteria B will be described below. In the first embodiment, diameter $\phi$ of bottom surface 111 of container 11 was 12 mm. The height of inner side surface 112 of container 11 was 1.5 mm (=1500 μm). This container 11 was subjected to gold sputtering to thereby form thin film 12 having a thickness of 10 nm. Then, container 11 was kept inside a storage apparatus (not shown) for 24 hours so as to prevent contamination of the inside of container 11.

Also, a dispersion liquid having bacteria B (specifically, *Staphylococcus aureus*) dispersed therein was prepared. The concentration of bacteria B in the dispersion liquid was $2.0 \times 10^8$ (cells/mL). This dispersion liquid was subjected to an ultrasonic treatment at 23 kHz for 10 minutes (the effect of the ultrasonic treatment will be described later). Then, 100 μL of dispersion liquid was dropped onto bottom surface 111 of container 11. Upon a correction in consideration of the refractive index (1.33) of water as a dispersion medium of dispersion liquid D, height H of the gas-liquid interface in the center of container 11 was 560 μm (at a scale of 420 in the up-down direction (the z-direction) of the XYZ-axis stage provided in a microscope used for measurement). In contrast, at inner side surface 112, a correction in consideration of the refractive index of water was not required, and the height of the gas-liquid interface at inner side surface 112 was within a range of 600 μm to 800 μm (at a scale of 600 on the above-mentioned scale). When the refractive index of water is not taken into consideration, the relation of 1 scale=1 μm is generally established.

The optical system of collecting apparatus 1 was set as follows. Objective lens 7 of 40-times magnification was used. The diameter of the laser spot was about 2.5 μm. The laser output having passed through objective lens 7 was about 35% of the laser output immediately after emission from laser beam source 5. The laser output having passed through bottom surface 111 of container 11 and thin film 12 was about 100 mW.

Thin film 92 on substrate 91 in the comparative example is the same as thin film 12 on bottom surface 111 of container 11. The dispersion liquid having bacteria B dispersed therein and the optical system of the collecting apparatus in the comparative example are the same as those in the first embodiment.

FIG. 7 shows sequential images illustrating an example of a result of collecting bacteria B. FIG. 7(A) shows the state where bacteria B are collected in the comparative example. FIG. 7(B) shows the state where bacteria B are collected in the first embodiment. FIGS. 7(A) and 7(B) each show images taken after 1 second, 10 seconds, 30 seconds, and 60 seconds having elapsed since the start of light irradiation. The focal point (focus position) of each image was set on the upper surface of bottom surface 111 of container 11 or on the upper surface of substrate 91.

In each of FIGS. 7(A) and 7(B), the position of the diameter of microbubble MB (the diameter at the position of an "equator") is indicated by MB. The diameter of microbubble MB in the first embodiment was greater than the diameter of microbubble MB in the comparative example. Specifically, the diameter of microbubble MB in the comparative example (having an average value of a plurality of measurement results, and the same is applied as well to the following numerical values) was 66.0 μm, whereas the diameter of microbubble MB in the first embodiment was 109 μm. In other words, according to the first embodiment, the diameter of microbubble MB was increased by 1.7 times.

Furthermore, the area of the region in which bacteria B were collected (which will be hereinafter also referred to as an "assembly area") A was $1.75 \times 10^3$ μm$^2$ in the comparative example and $3.74 \times 10^3$ μm$^2$ in the first embodiment. In other words, according to the first embodiment, assembly area A was increased by 2.1 times.

Furthermore, when specific bacteria B were tracked from among the sequential images, and the moving speed thereof (the moving speed at the position at a distance of about 200 μm from the laser spot) was calculated, the moving speed of bacteria B was 5.58 μm/s in the comparative example and 175 μm/s in the first embodiment. In other words, according to the first embodiment, it was confirmed that the moving speed of bacteria B was increased by 31 times.

<Determination as to Whether Bacteria are Alive or Dead>

When the temperature of dispersion liquid D excessively rises by light irradiation, the collected bacteria B may be damaged by heat and may become extinct. The following is an explanation about the result of determining by fluorescent staining whether collected bacteria B are alive or dead.

Figure 8:
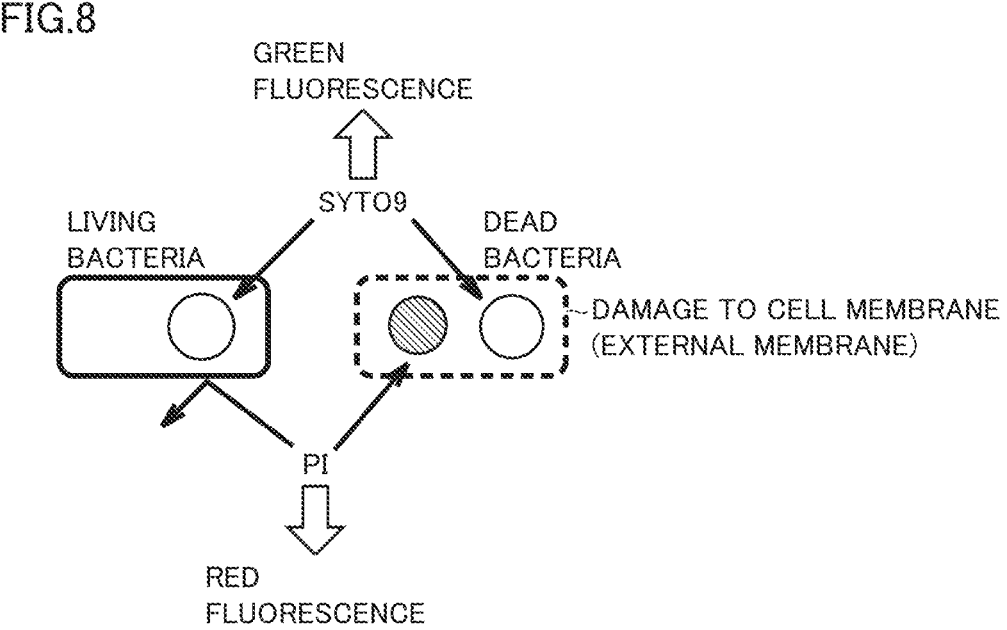
FIG. 8 is a diagram for illustrating a fluorescent staining method for bacteria.

FIG. 8 is a diagram for illustrating a fluorescent staining method for bacteria B. Generally, SYTO9 (registered trademark) and Propidium Iodide (PI) are known as a fluorescent dye for staining bacteria. SYTO9 is a DNA staining reagent having membrane permeability and serves to stain DNA irrespective of whether a bacterial cell membrane has been damaged or not. In other words, both the survived bacteria (living bacteria) and the extinct bacteria (dead bacteria) are stained by SYTO9. When the bacteria containing SYTO9 are irradiated with light having an excitation wavelength of SYTO9, the bacteria emit green fluorescence. In contrast, PI does not have membrane permeability. Accordingly, only the bacteria having a damaged cell membrane (that is, dead bacteria) are stained by PI. When PI is excited from outside, red fluorescence is emitted.

Figure 9:
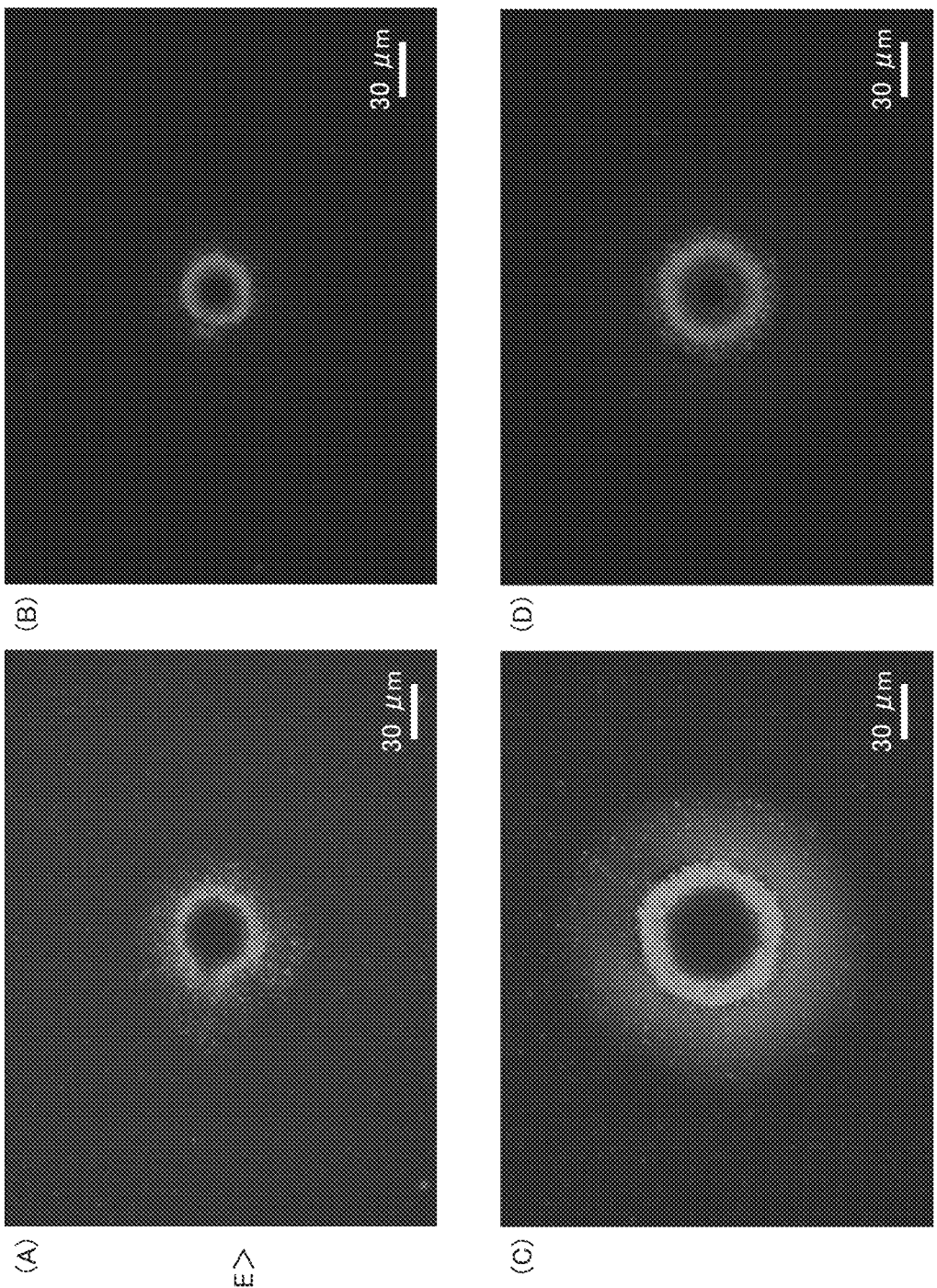
FIG. 9 shows fluorescence observation images of collected bacteria (more specifically, *Staphylococcus aureus*).

FIG. 9 shows fluorescence observation images of collected bacteria B. FIGS. 9(A) and 9(B) show a fluorescence observation image by an excitation wavelength of SYTO9 (also referred to as an "SYTO9 image") and a fluorescence observation image by an excitation wavelength of PI (also referred to as a "PI image"), respectively, in the comparative example. FIGS. 9(C) and 9(D) show an SYTO9 image and a PI image, respectively, in the first embodiment.

When comparing the SYTO9 images in FIGS. 9(A) and 9(C), it turns out that bacteria B were collected more in the first embodiment than in the comparative example. Also as shown in the PI images in FIGS. 9(B) and 9(D), dead bacteria are observed in the vicinity of the laser spot both in the comparative example and the first embodiment. When comparing the SYTO9 image and the PI image, the difference therebetween corresponds to the amount of living bacteria. It turns out that bacteria B could be collected alive in each of the comparative example and the first embodiment.

<Result of Collecting Beads>

Then, an example of the result of collecting beads will be described. Beads to be collected were polystyrene beads (produced by Micromod) each having a diameter of 1.0 μm. Also in this measurement, objective lens 7 of 40-times magnification was used. The laser output having passed through objective lens 7 was about 100 mW.

Figure 10:
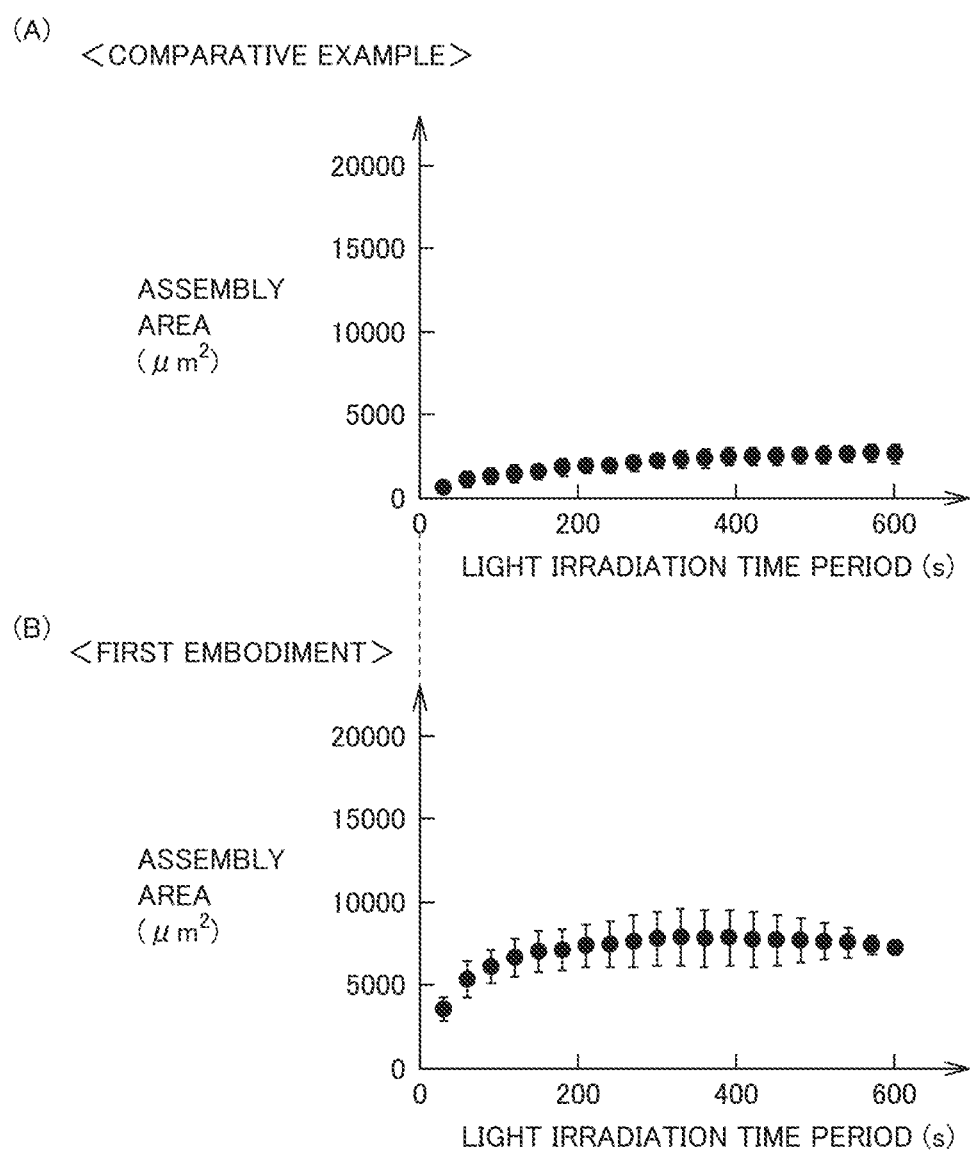
FIG. 10 is a diagram showing an example of a temporal change of an assembly area of beads.

FIG. 10 is a diagram showing an example of a temporal change of assembly area A of beads. FIG. 10(A) shows the state where beads are collected in the comparative example. FIG. 10(B) shows the state where beads are collected in the first embodiment. The horizontal axis shows an elapsed time since the start of light irradiation while the vertical axis shows assembly area A of beads. An error bar is obtained from the results of five times of measurements. FIG. 10(A) and FIG. 10(B) show that assembly area A of beads in the first embodiment is several times as large as assembly area A of beads in the comparative example.

<Influence of Particle Size>

The following is an explanation about the influence exerted by the particle size of each bead upon collection of beads. In the example described below, five types of polystyrene beads having different particle sizes (diameters) were prepared. The particle sizes of the beads were 50 nm, 100 nm, 200 nm, 500 nm, and 1 μm sequentially in increasing order of size. The beads with particle size of 1 μm were produced by Polysciences, Inc. while remaining beads were produced by Micromod. The concentration of beads in dispersion liquid D was set at $8.1 \times 10^{11}$ (particles/mL) for each bead having a particle size of 50 nm, set at $1.0 \times 10^{11}$ (particles/mL) for each bead having a particle size of 100 nm, set at $1.3 \times 10^{10}$ (particles/mL) for each bead having a particle size of 200 nm, set at $8.1 \times 10^{8}$ (particles/mL) for each bead having a particle size of 500 nm, and set at $1.0 \times 10^{11}$ (particles/mL) for each bead having a particle size of 1 μm. Also, Tween20 (registered trademark) as a surfactant was introduced into dispersion liquid D containing ultrapure water as a solvent. The concentration (volume percent concentration) of the surfactant was $10^{-3}$ (vol %).

Figure 11:
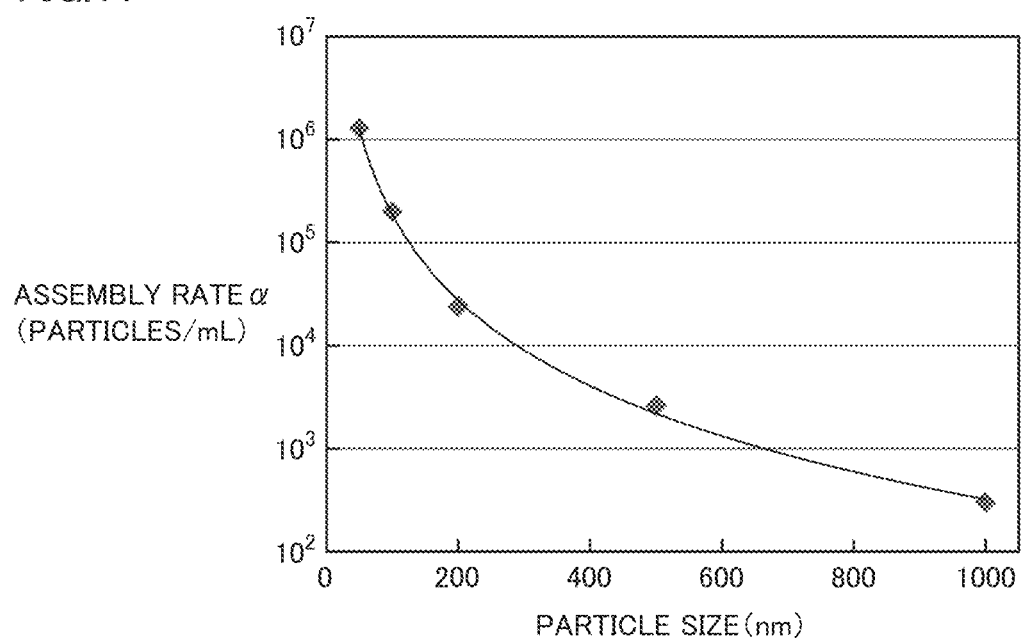
FIG. 11 is a diagram for illustrating an influence of the particle size of a bead.

FIG. 11 is a diagram for illustrating an influence of the particle size of each bead. The light irradiation time period was fixed at 300 seconds in any particle size. In FIG. 11, the horizontal axis shows the particle size of each bead. The vertical axis shows the "assembly rate" α (particles/s) showing the number of beads collected per unit time on the logarithmic scale.

Assembly rate α of beads can be calculated according to the following equation (1). In the equation (1), the total volume of beads collected in a region shown by assembly area A (for example, see FIGS. 7(A) and 7(B)) is denoted by V(A), the volume of each bead is denoted by vp, and the light irradiation time period (the heating time period) is denoted by t.

$$V(A) - vp \times \alpha \times t = 0 \quad (1)$$

Total volume V(A) of beads can be calculated as a volume of the space sandwiched between thin film 12 and microbubble MB, which can be approximated to a sphere, in the region in which beads are collected (the region corresponding to assembly area A of beads). Also, volume vp of each bead is known from the particle size of each bead, and light irradiation time period t is also known by measuring the time period. Therefore, by substituting these parameters into the equation (1), assembly rate α of beads can be calculated.

As shown in FIG. 11, it was confirmed that assembly rate α becomes lower as the particle size of each bead becomes larger, but the beads having particle sizes in a wide range from 50 nm to 1 μm can be collected.

<Accuracy of Estimating Concentration of Microscopic Objects>

Estimation of the concentration of microscopic objects dispersed in dispersion liquid D (which may be rephrased as the number of microscopic objects in dispersion liquid D if the volume of dispersion liquid D is known or can be measured) may be required. The following is an explanation about the result of verifying the concentration estimation accuracy achieved when such an estimation of the concentration of microscopic objects was performed utilizing a collecting mechanism by light irradiation. In this verification, *Staphylococcus aureus* (which will be hereinafter also referred to as bacteria B) having a diameter of 1 μm was used as a microscopic object. The light irradiation time period was set at 300 seconds.

Figure 12:
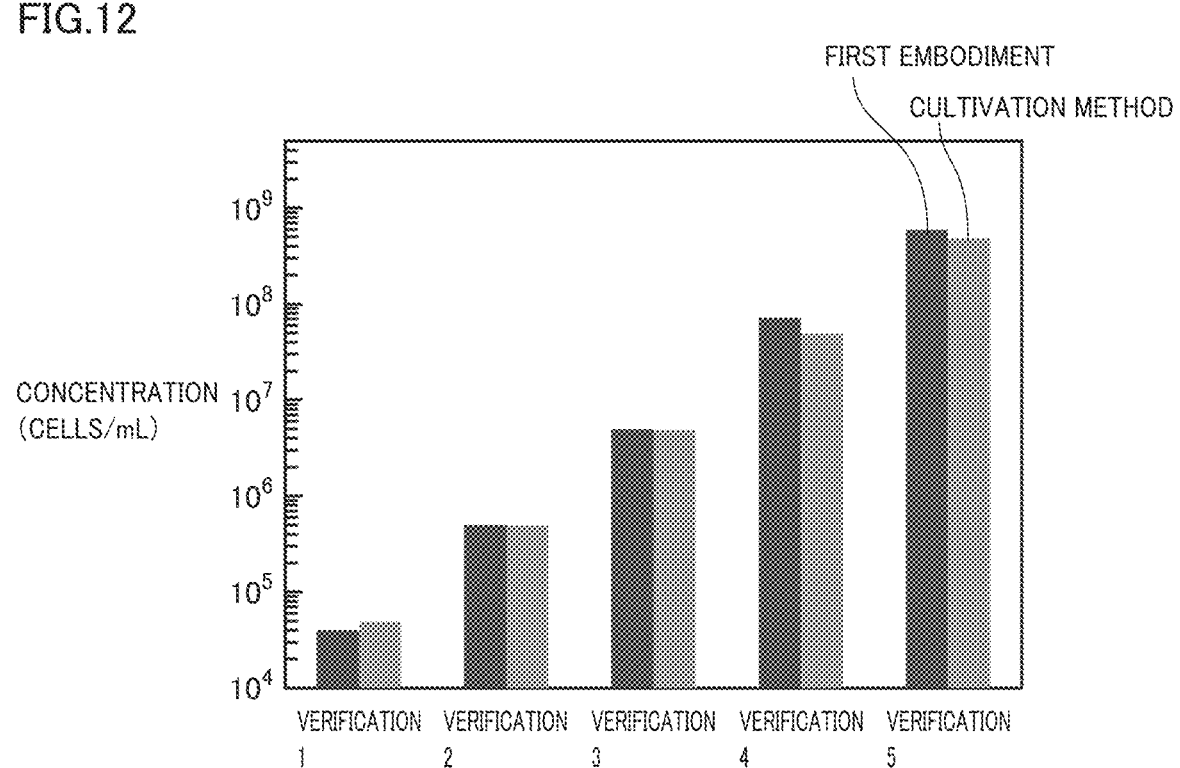
FIG. 12 is a diagram for illustrating a result of verifying the accuracy of estimating the concentration of bacteria.

FIG. 12 is a diagram for illustrating a result of verifying the accuracy of estimating the concentration of bacteria B. The vertical axis in FIG. 12 shows the concentration of bacteria B. FIG. 12 shows the results of five times of verifications using samples having different concentrations. The accuracy of estimating the concentration of bacteria B collected by collecting apparatus 1 in the first embodiment is shown by a dark-colored bar graph (a graph on the left side of two adjoining bar graphs).

A correlation exists between concentration C of bacteria B in dispersion liquid D and assembly rate α of bacteria B. More specifically, with regard to beads each having a diameter of 1 μm, the correlation represented as $\alpha = \beta C^k$ using a coefficient β and an index k exists between assembly rate α and concentration C, as shown later in FIG. 30. Coefficient β and index k are fixed as long as the microscopic objects are approximately equal in size even when the types of microscopic objects are different between the beads and the bacteria (in this example, $\beta = 6.3 \times 10^{-8}$, $k = 1.18$ in the case where laser irradiation time period is 300 seconds). Based on the knowledge as described above, a plurality of dispersion liquids D each having beads dispersed therein are prepared. The concentration C of beads is known. Then, assembly rate α of beads is calculated for each dispersion liquid D according to the above-mentioned equation (1). Thereby, the correlation between concentration C and assembly rate α of beads ($\alpha = \beta C^k$) can be calculated. Then, by referring to this correlation, concentration C for bacteria B can also be estimated from assembly rate α.

In FIG. 12, for comparison, a light-colored bar graph (a graph on the right side) shows the result of estimating the concentration achieved by the method of cultivating bacteria B, which has conventionally been used widely. In each of the results of five times of verifications, it was confirmed that the concentration of bacteria B estimated in the first embodiment was significantly identical to the concentration of bacteria B estimated by the cultivation method.

<Influence of Ultrasonic Treatment>

The following is a detailed explanation about the effect of an ultrasonic treatment based on comparison between the collection results achieved upon execution of an ultrasonic treatment and the collection results achieved upon non-execution of an ultrasonic treatment. In this measurement, beads were used as targets to be collected. However, in the following description, beads can be rephrased appropriately as bacteria B (or other microscopic objects).

In the ultrasonic treatment, for example, the dispersion liquid having beads dispersed therein is transferred to another container for ultrasonic treatment (a microtube and the like (not shown)), and irradiated with ultrasonic waves of a prescribed frequency (for example, 23 kHz) for a prescribed time period (for example, 10 minutes). A small amount of amphiphilic substances 19 (see FIG. 15(B)) can be attached in advance to the inner surface of this microtube. When the dispersion liquid having beads dispersed therein is added to such a microtube, which is then subjected to an ultrasonic treatment, the amphiphilic substances peel off from the inner surface of the microtube and disperse into dispersion liquid D. As a result, when the dispersion liquid having beads dispersed therein is transferred from the microtube into container 11, amphiphilic substances 19 are also transferred to container 11.

Figure 13:
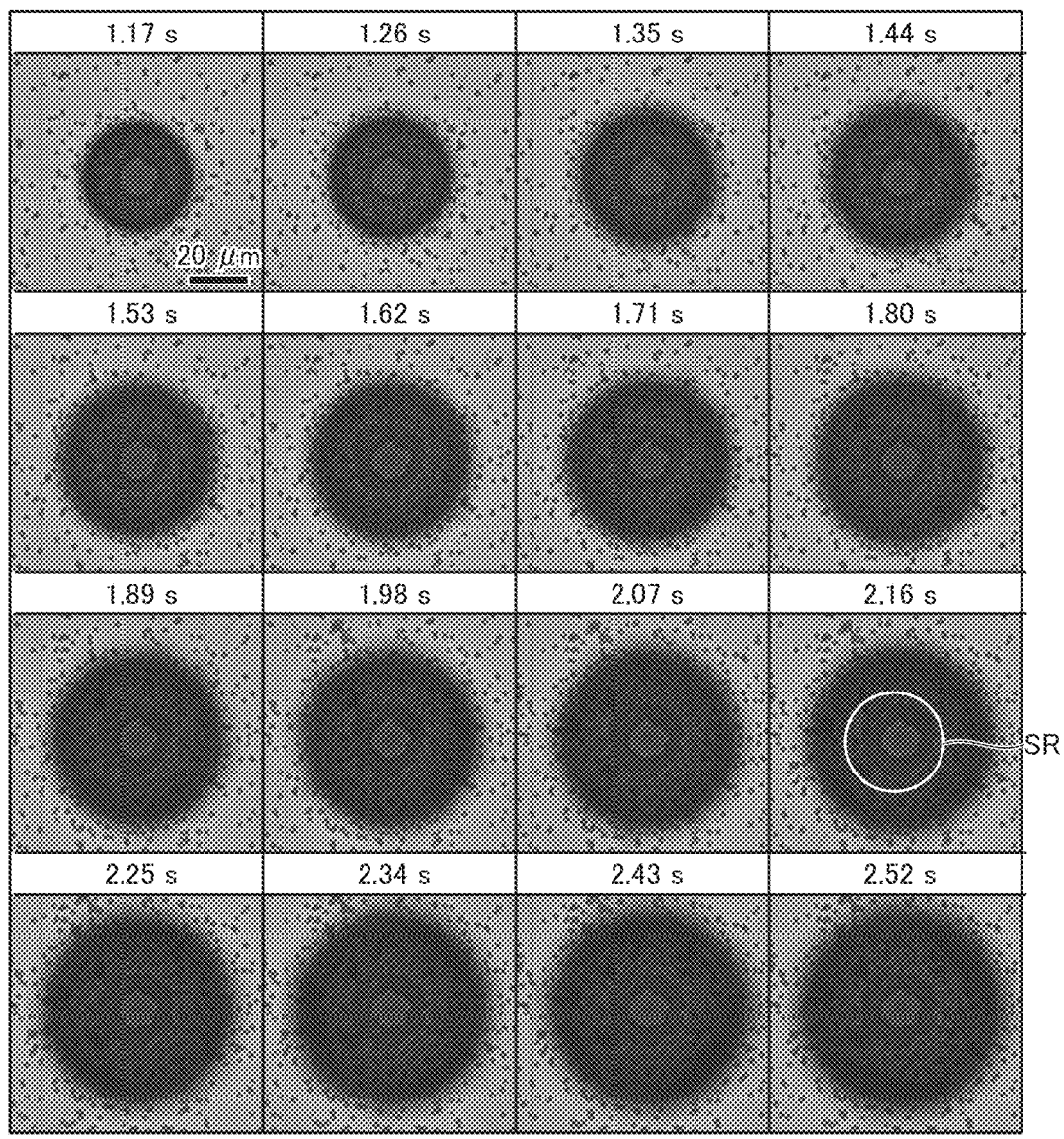
FIG. 13 shows sequential images illustrating the state where beads are collected when an ultrasonic treatment is not performed.
Figure 14:
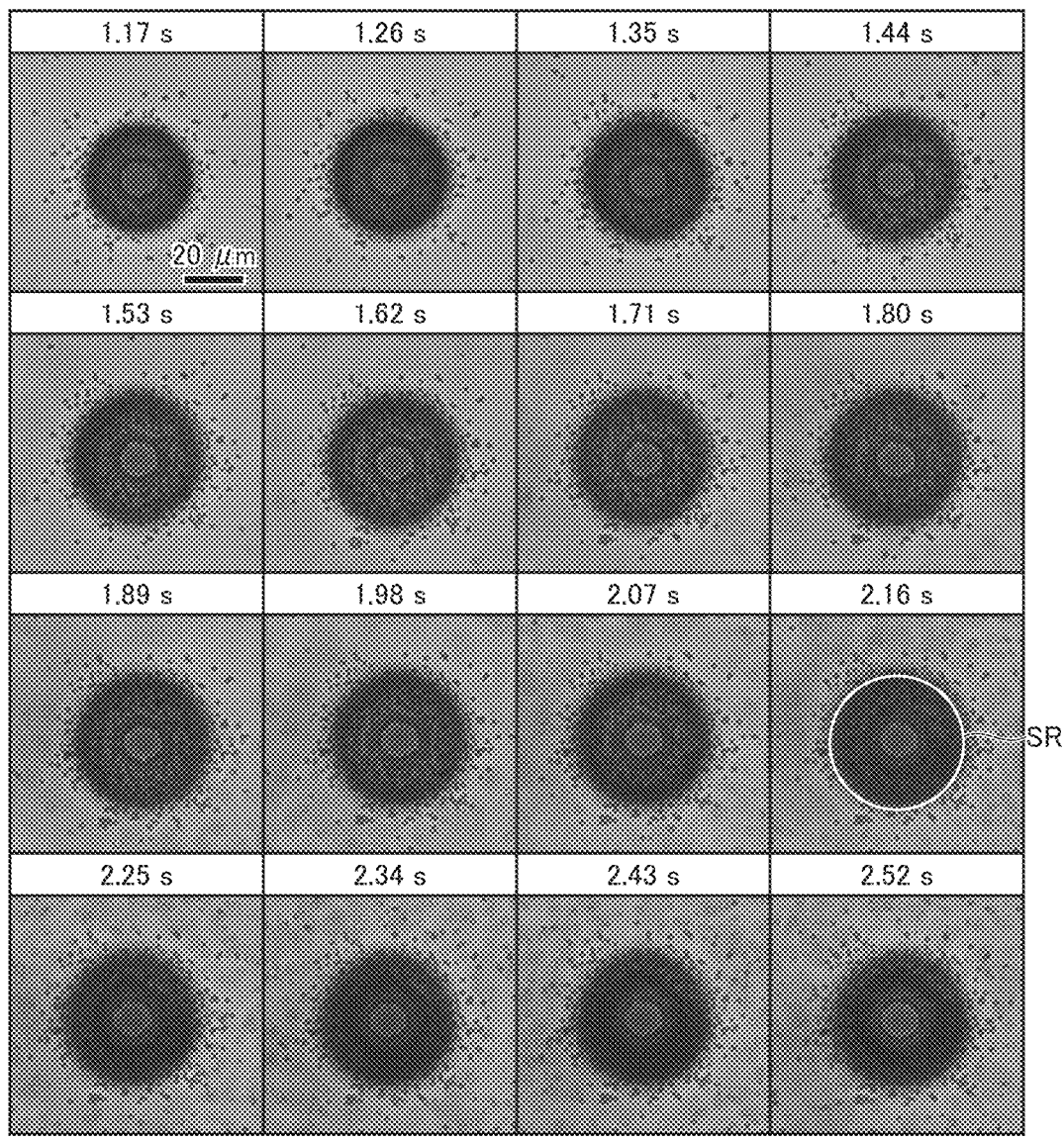
FIG. 14 shows sequential images illustrating the state where beads are collected when the ultrasonic treatment is performed.

FIG. 13 shows sequential images illustrating the state where beads are collected when an ultrasonic treatment is not performed. FIG. 14 shows sequential images illustrating the state where beads are collected when an ultrasonic treatment is performed. Each of the sequential images shows the result obtained using a microtube having an inner surface to which amphiphilic substances are attached. The numerical values in the figure each show the time period having elapsed since the start of light irradiation.

When comparing the images obtained after a lapse of 2.16 seconds since the start of light irradiation between the sequential images shown in FIGS. 13 and 14, beads are collected at a high density in stagnation region SR when an ultrasonic treatment is performed, whereas the beads are collected at a relatively low density in stagnation region SR when an ultrasonic treatment is not performed. These results show that collection of beads can be facilitated by an ultrasonic treatment.

FIG. 15 is a diagram for illustrating a collection facilitating mechanism by the ultrasonic treatment. As shown in FIG. 15(A), for example, when bacteria B reach near the side surface of microbubble MB by a thermal convection, external force FH and external force FI act on bacteria B.

External force FH results from a thermal convection. Since the portion below microbubble MB is heated by light irradiation, the lower portion of microbubble MB is higher in temperature than the upper portion of microbubble MB. Thus, a thermal convection occurs to flow from below to above. Therefore, external force FH resulting from the thermal convection acts on bacteria B from below to above.

Also on the surface of microbubble MB, a Marangoni convection occurs along the surface of microbubble MB due to the gradient of the interfacial tension resulting from the temperature difference in the direction along the surface of microbubble MB (in the up-down direction). External force FI is an interfacial tension between dispersion liquid D and microbubble MB. As the temperature is higher, the interfacial tension becomes smaller. Thus, the interfacial tension of the lower portion of microbubble MB is smaller than the interfacial tension of the upper portion of microbubble MB. In addition, the direction in which the interfacial tension between dispersion liquid D and microbubble MB acts is set in accordance with the characteristics of dispersion liquid D (more specifically, the substance contained in dispersion liquid D, the concentration distribution thereof, and the temperature distribution of dispersion liquid D).

In terms of energy, amphiphilic substances 19 are stabilized more in the case where hydrophobic groups are directed toward microbubble MB and adsorbed to the surface of microbubble MB (a type of gas-liquid interface) than in the case where the floating (dispersed) state in dispersion liquid D is maintained. Thus, amphiphilic substances 19 are more likely to adsorb to the surface of microbubble MB.

When microbubble MB grows by heating resulting from light irradiation, the probability of contact (probability of collision) with amphiphilic substances 19 in dispersion liquid D is higher in the upper region of microbubble MB than in the lower region of microbubble MB. Accordingly, the concentration of amphiphilic substances 19 adsorbing to the upper surface of microbubble MB is more likely to be higher than the concentration of amphiphilic substances 19 adsorbing to the lower portion of microbubble MB. In a liquid, as the concentration of amphiphilic substances is higher, the interfacial tension (interface free energy) becomes lower. Thus, when an ultrasonic treatment is performed, external force FI may act from above to below depending on the concentration difference of amphiphilic substances 19 in the up-down direction.

As shown in FIG. 15(B), when external force FI acts from above to below, bacteria B are less likely to rise above microbubble MB, so that bacteria B are more likely to stagnate in stagnation region SR. In other words, bacteria B are more likely to be collected in stagnation region SR. When an ultrasonic treatment for dispersing surfactants in dispersion liquid D is performed, the efficiency of collecting bacteria B can be further enhanced by the mechanism as described above. The collection results shown in FIGS. 7 and 9 each are obtained by performing the ultrasonic treatment.

In the example as described above, amphiphilic substances 19 are attached to the inner surface of a microtube. However, amphiphilic substances 19 may be attached to the inner surface of container 11 and container 11 may be subjected to an ultrasonic treatment. Also, amphiphilic substances 19 may be directly added into dispersion liquid D.

As described above, according to the first embodiment, dispersion liquid D is held in container 11 such that a meniscus is formed to be concave with respect to the gas-liquid interface. Thereby, a temperature gradient can be produced in dispersion liquid D by the photothermal effect caused by irradiation of light with thin film 12, so that a thermal convection can be produced in dispersion liquid D while a Marangoni convection can be produced at the gas-liquid interface. Since the thermal convection and the Marangoni convection flow in the same direction and strengthen against each other, the moving speed of bacteria B is increased. As a result, the amount of bacteria B collected in stagnation region SR can be increased. In this way, according to the first embodiment, bacteria B dispersed in dispersion liquid D can be collected at a high density and with high efficiency.

Modification of First Embodiment

Figure 16:
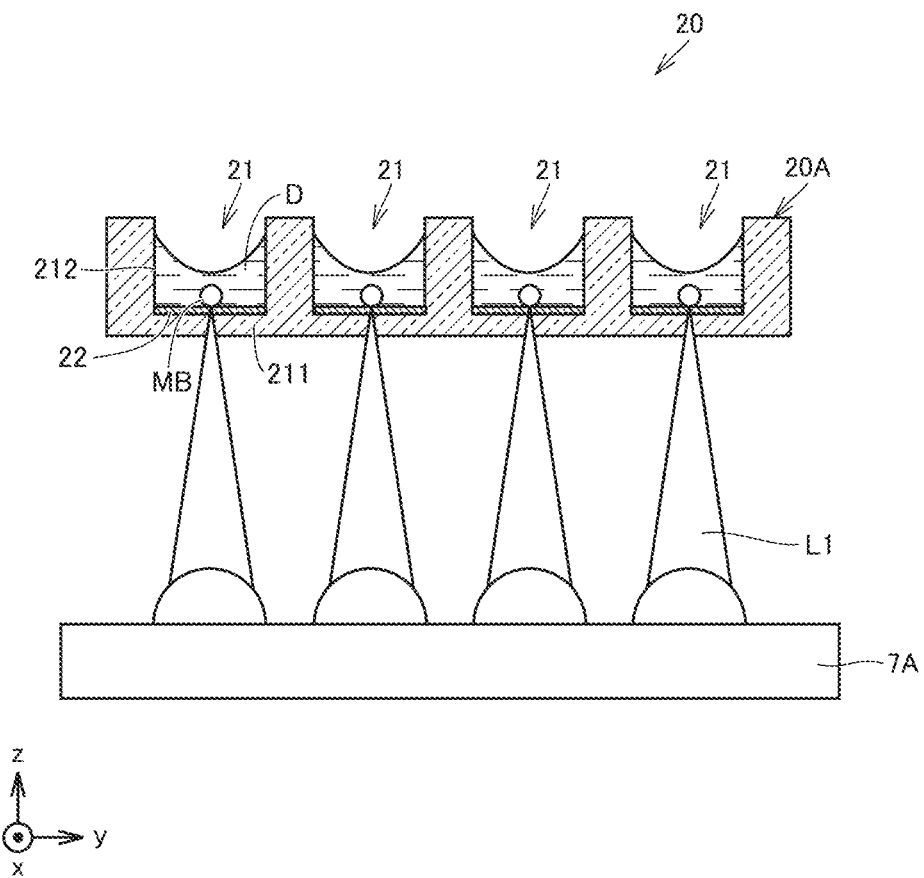
FIG. 16 is a diagram schematically showing the configuration of and around a collecting kit in a modification of the first embodiment.

FIG. 16 is a diagram schematically showing the configuration of and around a collecting kit 20 in a modification of the first embodiment. As shown in FIG. 16, collecting kit 20 is provided with a microwell array 20A. Microwell array 20A includes a plurality of microwells 21 arranged in an array shape.

The internal configuration of each microwell 21 is basically the same as the internal configuration of container 11 (see FIG. 3) having been described in the first embodiment, and therefore, the detailed explanation thereof will not be repeated. In addition, FIG. 16 shows an example in which four microwells 21 are formed in order to prevent complicated illustrations. However, the number of microwells 21 is not particularly limited as long as a plurality of microwells 21 are provided, and about several hundreds to several thousands of microwells 21 may be provided, for example.

Furthermore, the collecting apparatus according to the modification of the first embodiment includes a microlens array 7A in place of objective lens 7. In microlens array 7A, lenses are arranged so as to correspond, in the one-to-one relation, to microwells 21 formed in collecting kit 20. Microlens array 7A causes laser beam L1 from laser beam source 5 to branch off, and then, condenses laser beam L1 so as to be applied to each of the plurality of microwells 21. The configurations other than the above-described configuration of the collecting apparatus according to the modification of the first embodiment are the same as the corresponding configurations of collecting apparatus 1 according to the first embodiment (see FIG. 1).

As described above, according to the modification of the first embodiment, microwell array 20A and microlens array 7A are provided. Thereby, laser beam L1 from one laser beam source 5 can simultaneously achieve a large number of collection effects. Furthermore, when dispersion liquid D containing a different type of microscopic object is dropped for each microwell 21, a plurality of types of microscopic objects can be collected in one collecting process.

Second Embodiment

According to the description in the first embodiment, bacteria B can be collected in the vicinity of the laser spot at a high density and with high efficiency. However, depending on the setting of collecting conditions (the thickness of thin film 12, a laser output or the like), the temperature in the vicinity of the laser spot may excessively rise to thereby thermal damage bacteria. The second embodiment will be described with regard to the technique by which microscopic objects such as bacteria can be collected while suppressing damage caused by heat.

The second embodiment will also be described with regard to an example of the configuration in which bacteria (more specifically, *Escherichia coli* and *Staphylococcus aureus*) are collected. The microscopic object as a target to be collected is not particularly limited as long as it is desirable to suppress damage caused by heat. Thus, the microscopic object may be other biological substances, for example. The entire configuration of the collecting apparatus according to the second embodiment is the same as the configuration of collecting apparatus 1 in the first embodiment (see FIG. 1), and therefore, the description thereof will not be repeated.

<Configuration of Collecting Kit>

Figure 17:
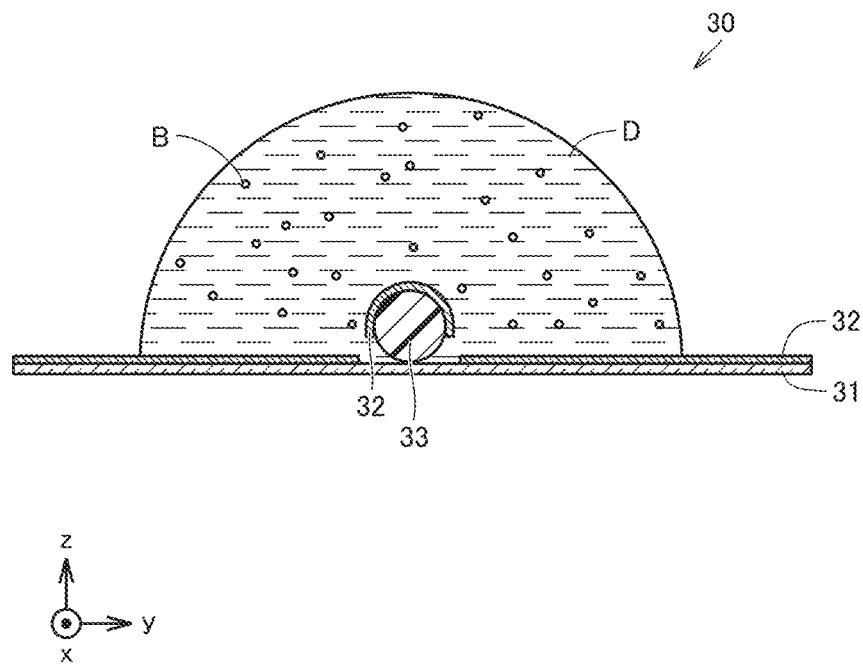
FIG. 17 is a diagram schematically showing the configuration of a collecting kit in the second embodiment.

FIG. 17 is a diagram schematically showing the configuration of a collecting kit 30 in the second embodiment. FIG. 17 shows a cross-sectional view of collecting kit 30. Collecting kit 30 includes a substrate 31, a thin film 32, and a heat insulating spacer (which will be abbreviated as a "spacer") 33.

Substrate 31 is formed of a material that does not influence the photothermal effect by thin film 32, and may be a glass substrate, for example, as in the comparative example (see FIG. 2).

Spacer 33 is formed on substrate 31 for the purpose of ensuring the space for suppressing heat conduction. Thus, spacer 33 is made of a material that does not absorb laser beam L1 from laser beam source 5 and that has relatively low thermal conductivity. Spacer 33 is a resin bead having a size in the micrometer order, for example. In the second embodiment, a polystyrene bead having a diameter of 100 µm is used as spacer 33.

Spacer 33 on substrate 31 is prepared as follows. First, a prescribed amount (for example several µL) of the dispersion liquid of spacer 33 is dropped onto substrate 31. Then, substrate 31 is naturally dried or vacuum-dried, thereby evaporating the dispersion medium. In this way, spacer 33 can be fixed onto substrate 31.

The shape of spacer 33 is not particularly limited, but may be a rectangular parallelepiped shape, a cylindrical shape, or a more complicated shape, for example. Furthermore, the material of spacer 33 is also not limited to polystyrene, but may be other resins such as acrylic, polyolefin, polyethylene, and polypropylene, or may be silica, for example. Furthermore, substrate 31 and spacer 33 may be integrally formed of the same material.

In collecting kit 30, a thin film 32 is further formed on spacer 33 fixed onto substrate 31. Thin film 32 is a metal thin film having a thickness in the nanometer order, for example, as in the comparative example and the first embodiment. In the second embodiment, a gold thin film having a thickness of 10 nm was formed by sputtering. The method of forming thin film 32 is not particularly limited, but may be electroless plating.

FIG. 18 is a diagram for more specifically illustrating the configuration around spacer 33 shown in FIG. 17. FIG. 18(A) shows the state around the laser spot in the comparative example for comparison. Furthermore, FIG. 18 and FIG. 31 (described later) do not show microscopic objects such as bacteria in dispersion liquid D.

In the comparative example, the photothermal effect by thin film 92 occurs at the position of the laser spot, as shown in FIG. 18(A). Then, as having been described with reference to FIG. 5, microbubble MB grows while a thermal convection occurs, so that bacteria B are collected in stagnation region SR.

A relatively large area of microbubble MB is in contact with dispersion liquid D in stagnation region SR. Microbubble MB is produced as a result of vaporization of the dispersion medium (water in this example) locally boiled by the photothermal effect of thin film 92. Thus, the temperature of microbubble MB is high. This can be recognized as the situation in which the so-called "heat source" is provided in the vicinity of stagnation region SR. Accordingly, in the configuration shown in FIG. 18(A), stagnation region SR is brought into contact with the heat source, so that the temperature of stagnation region SR is more likely to rise. As a result, bacteria B collected in stagnation region SR may be damaged by heat.

In contrast, in the second embodiment, spacer 33 is provided on substrate 31 (see FIG. 18(B)). This can prevent an excessive rise in temperature in the collecting region of bacteria B mainly for three reasons, which will be described below.

The first reason will be hereinafter described. Sputtering for forming thin film 32 is performed after spacer 33 is fixed onto substrate 31. Thus, a lower region LR on which no thin film 32 is formed (that is, to which sputtered gold nanoparticles are not attached) between substrate 31 and spacer 33. Accordingly, upon irradiation with laser beam L1, no photothermal effect occurs in lower region LR, but heat is generated by the photothermal effect of thin film 32 formed on upper region UR of spacer 33. Therefore, the distance between the collecting region of bacteria B and the heating region (upper region UR) can be ensured as compared with the comparative example (see FIG. 18(A)).

The second reason will be hereinafter described. Spacer 33 is significantly lower in thermal conductivity than thin film 32. More specifically, the thermal conductivity of gold is generally within a range of 80 to 320 (W/m·K) though depending on the shape of gold (for example, the film thickness of the gold thin film). In contrast, the thermal conductivity of polystyrene as a material of spacer 33 is 0.1 (W/m·K). In other words, the thermal conductivity of spacer 33 is smaller by triple digits in order than the thermal conductivity of gold. The thermal conductivity of water is 0.6 (W/m·K), and the thermal conductivity of glass is 1 (W/m·K). Since the thermal conductivity of spacer 33 is relatively low in this way, the heat generated in thin film 32 is less likely to be conducted to the inside of spacer 33. Thus, the temperature of spacer 33 is less likely to rise unlike microbubble MB that inevitably rises in temperature.

The third reason will be hereinafter described. The heat generated in thin film 32 (more specifically, upper region UR) is conducted through thin film 32 formed on the surface of spacer 33. The heat capacity of thin film 32 is relatively small. On the other hand, the surface area of thin film 32, that is, the contact area of thin film 32 with the surrounding dispersion liquid D is relatively large. Thus, thin film 32 is more likely to be cooled by heat exchange with dispersion liquid D that convects.

Mainly for the above-described three reasons, according to the second embodiment, providing spacer 33 can prevent an excessive rise in temperature in the collecting region of bacteria B. As a result, damage to collected bacteria B by heat can be suppressed.

In the second embodiment, dispersion liquid D is heated by the heat generated in upper region UR of spacer 33. Thus, a thermal convection mainly occurs above spacer 33 while the flow in the region corresponding to stagnation region SR in the comparative example (see FIG. 18(A)) is relatively weak.

<Result of Collecting Beads>

In the following description, the height of the beam waist of laser beam L1 with respect to the upper surface of substrate 31 (the distance between the upper surface of substrate 31 and the beam waist) will be denoted as h (see FIG. 18(C)). First, the influence that may be exerted by height h of the beam waist upon collection of microscopic objects has been examined. In this case, a dispersion liquid having polystyrene beads (which will be hereinafter abbreviated as "beads") of 1 µm in diameter dispersed therein was used in place of the dispersion liquid having bacteria B dispersed therein.

Figure 19:
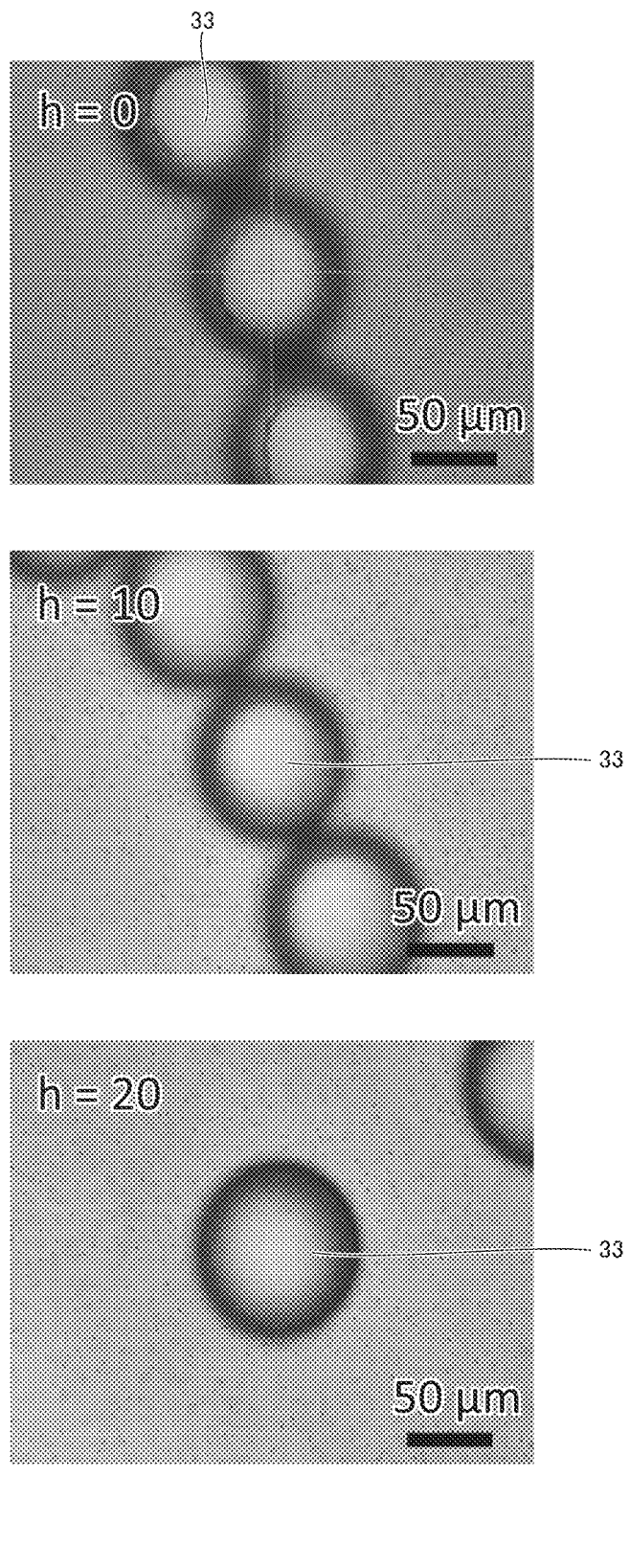
FIG. 19 is a diagram for illustrating the height dependency of a beam waist.

FIG. 19 is a diagram for illustrating the height dependency of the beam waist. Height h of the beam waist is 0 µm, 10 µm, and 20 µm sequentially from the top. A large number of microscopically small black points shown in the figure are beads.

When height h of the beam waist was 0 µm or 10 µm, the beads were collected in the vicinity of spacer 33 by light irradiation. On the other hand, when height h of the beam waist was 20 µm, it was observed that the beads could not be appropriately collected and were moved in the direction away from spacer 33. Thus, in the following, more specific measurements were done for the beam waist having height h of 0 µm or 10 µm.

Figure 20:
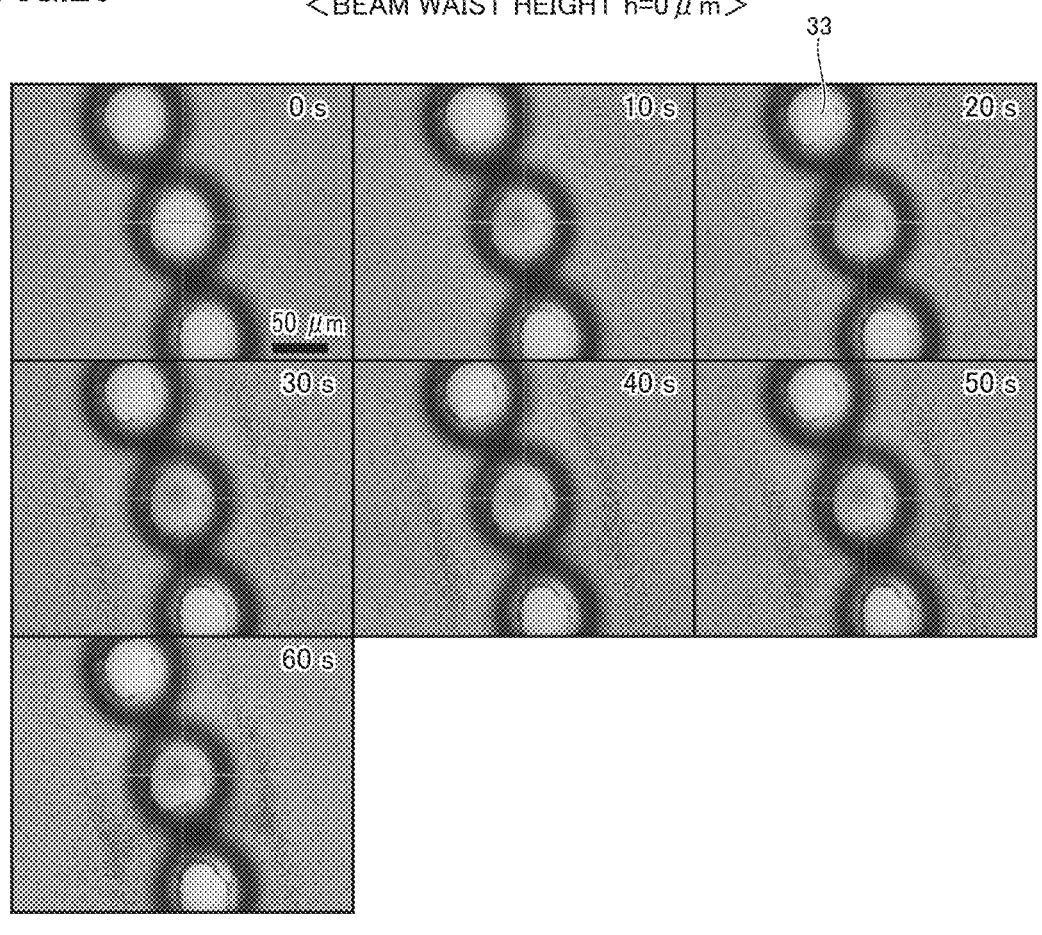
FIG. 20 shows sequential images illustrating the state where beads are collected in the case where a beam waist height h=0 μm.
Figure 21:
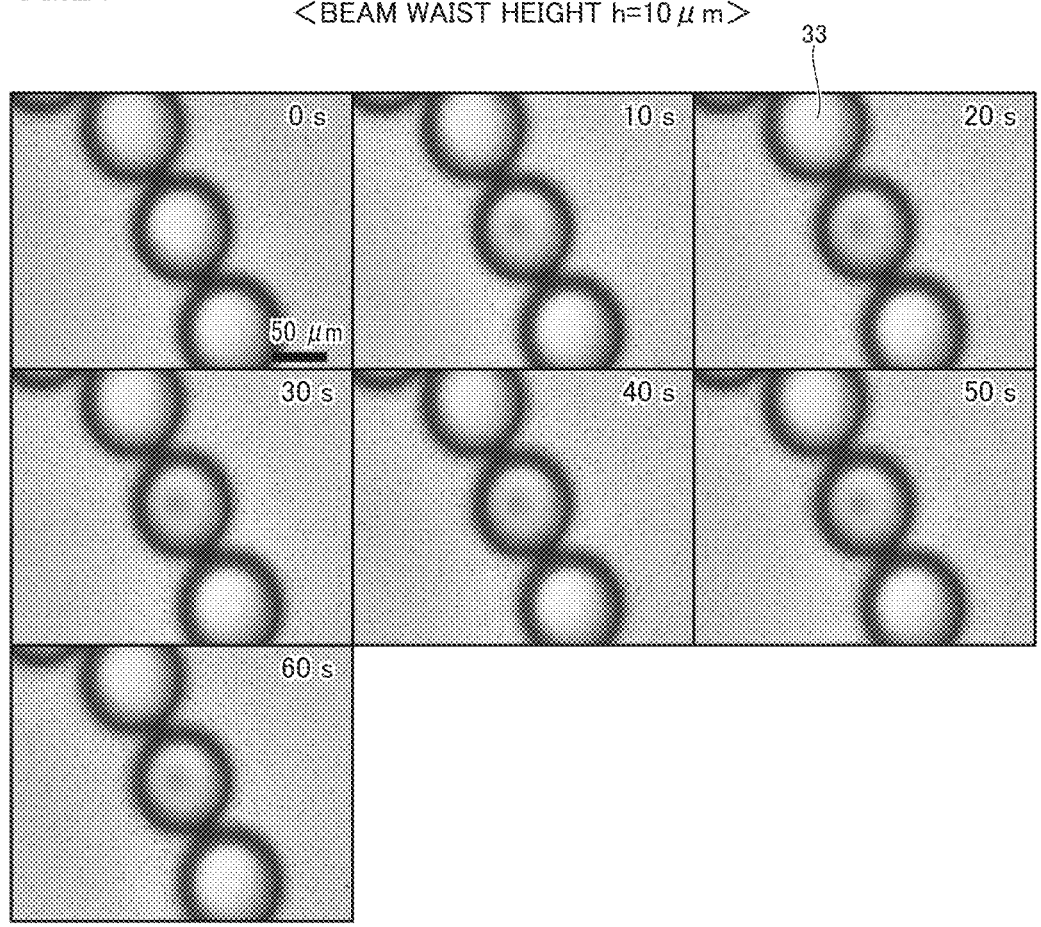
FIG. 21 shows sequential images illustrating the state where beads are collected in the case where beam waist height h=10 μm.

FIG. 20 shows sequential images illustrating the state where beads are collected in the case where beam waist height h=0 µm. FIG. 21 shows sequential images illustrating the state where beads are collected in the case where beam waist height h=10 µm. The center in each figure (the point of intersection between a vertical line and a horizontal line) corresponds to the position of the laser spot. Each of the numerical values in the figure shows the time period having elapsed since the start of light irradiation.

Referring to FIG. 20, in the case where beam waist height h=0 µm, it was confirmed that the beads were collected around spacer 33 at a high density in several tens of seconds after the start of light irradiation. It turns out that the beads are less likely to be collected in the range of a certain distance from spacer 33 (in the range of several tens of µm in the example shown in FIG. 20). This will be explained as below.

When a resin (polystyrene or the like) or silica is used as a material of spacer 33, an electric double layer is formed around spacer 33 since each spacer 33 is negatively charged. In addition, the beads are also negatively charged (more specifically, when the beads are made of polystyrene, a zeta potential is about −30 mV). Thus, electrical repelling force (repulsive force) acts between the beads and spacer 33. In the case where beam waist height h=0 µm, the thermal convection is relatively gentle. Accordingly, the electrical repelling force acting on the beads is higher in the vicinity of spacer 33 than the external force by the thermal convection. As a result, it is considered that the beads are collected at a certain distance from spacer 33.

Referring to FIG. 21, in the case where beam waist height h=10 µm, the thermal convection is stronger than that in the case where beam waist height h=0 µm. Thus, it was confirmed that the rate of collecting beads from the start of light irradiation was relatively high. It also turns out that the beads can be collected to the close vicinity of spacer 33.

<Collection of Bacteria and Determination as to Whether Bacteria are Alive or Dead>

The following is an explanation about an example of the result of collecting bacteria B and the result of determining whether bacteria are alive or dead. In the second embodiment, *Escherichia coli* and *Staphylococcus aureus* were used as bacteria B. *Escherichia coli* is *Bacillus* and has a long-axis with a length of several µm. In contrast, *Staphylococcus aureus* is coccus and has a diameter of about 1 µm. However, when *Escherichia coli* and *Staphylococcus aureus* are not distinguished from each other, they are simply described as bacteria B.

In the following, height h of the beam waist of laser beam L1 was set at 0 µm while the laser output having passed through objective lens 7 and substrate 31 was set at 1.0 W. Furthermore, the irradiation time period of laser beam L1 was set at one minute. Each transmission image was obtained at the time when one minute has elapsed since the start of light irradiation. Furthermore, a fluorescence observation image was obtained immediately after the end of light irradiation.

Figure 22:
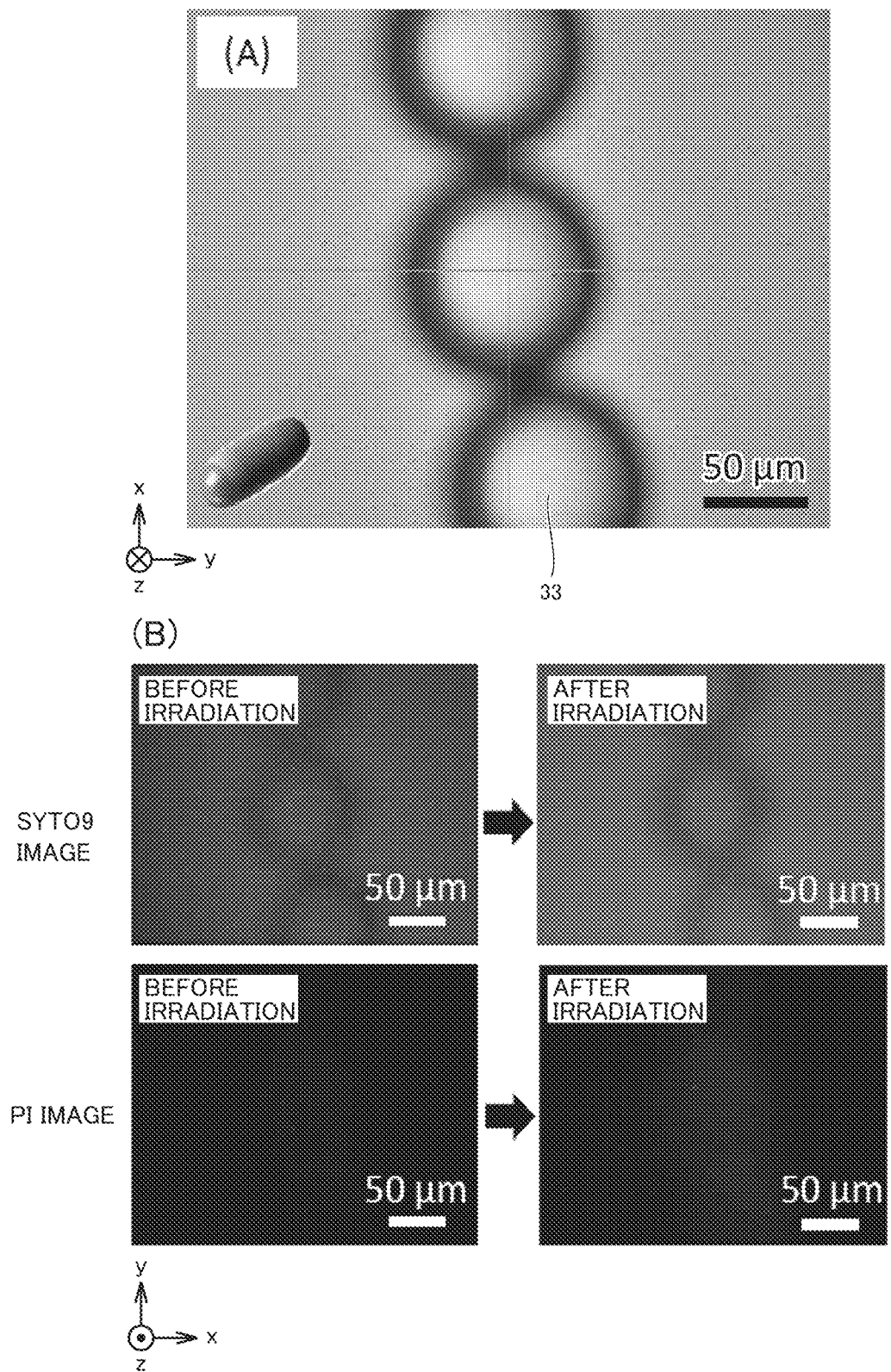
FIG. 22 is a diagram showing a result of collecting *Escherichia coli* in the second embodiment.
Figure 23:
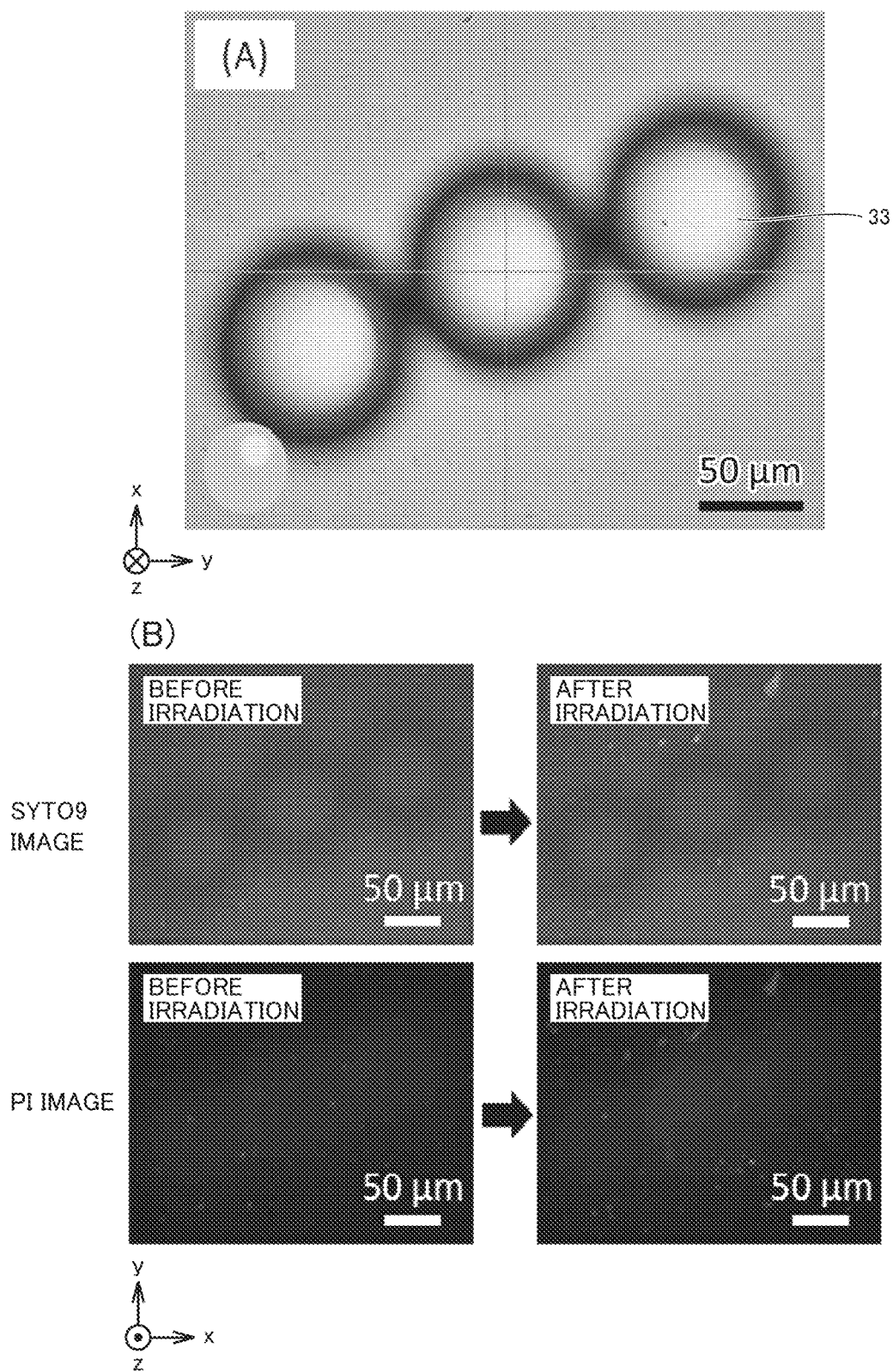
FIG. 23 is a diagram showing a result of collecting *Staphylococcus aureus* in the second embodiment.

FIG. 22 is a diagram showing a result of collecting *Escherichia coli* in the second embodiment. FIG. 23 is a diagram showing a result of collecting *Staphylococcus aureus* in the second embodiment. FIGS. 22(A) and 23(A) show transmission images. FIGS. 22(B) and 23(B) show fluorescence observation images (SYTO9 images are shown in the upper stage and PI images are shown in the lower stage).

The transmission images in FIGS. 22(A) and 23(A) show that bacteria B can be collected by light irradiation irrespective of the shapes of bacteria B. Furthermore, the PI images in FIGS. 22(B) and 23(B) show that dead bacteria hardly occur in collected bacteria B, so that bacteria B can be collected alive at a high ratio.

As described above, according to the second embodiment, spacer 33 that is lower in thermal conductivity than thin film 32 and that prevents heat conduction from thin film 32 is provided on substrate 31, so that the heat generated by the photothermal effect of thin film 32 is less likely to be conducted to the collecting region of bacteria B. Thereby, an excessive rise in temperature in the collecting region of bacteria B can be prevented, so that damage to bacteria B by heat can be suppressed. As a result, a high survival ratio (the ratio of the number of living bacteria to the number of all of the collected bacteria) can be implemented.

<Influence of Surfactant>

With regard to the collecting mechanism (see FIGS. 5 and 6) for microscopic objects such as bacteria B or beads, a thermal convection and a Marangoni convection at the gas-liquid interface have been described as an effect contributing to collection of microscopic objects, and also, it has been described that the thermal convection is accelerated by evaporation of the dispersion medium from the gas-liquid interface. In the collecting process using such an effect, depending on the collecting conditions (for example, the laser output from laser beam source 5 or the thickness of thin film 52), an excessively intense thermal convection may occur, so that microscopic objects may not be collected appropriately in the vicinity of spacer 33 (or microbubble MB). In that case, a surfactant can be introduced into dispersion liquid D. The second embodiment will be described also with regard to the effect of the surfactant achieved when the surfactant is introduced into dispersion liquid D.

Also in the second embodiment and in the second modification (described later) of the second embodiment, Tween20 (registered trademark) was used as a surfactant. As a concentration of the surfactant, there is a concentration suitable for collecting microscopic objects (beads produced by Micromod in the following example) in stagnation region SR. As a result of the evaluation test conduced in advance, the concentration (volume percent concentration) of the surfactant was set at $10^{-1}$ (vol %). Furthermore, assuming that objective lens 7 of 40-times magnification was used, the laser output having passed through objective lens 7 was set at 0.05 W.

FIG. 24 is a diagram for illustrating an influence of the surfactant in the second embodiment. FIG. 24(A) shows the state in the vicinity of spacer 33 at the time when no surfactant was introduced. FIG. 24(B) shows the state in the vicinity of spacer 23 at the time when a surfactant was introduced. Each of the numerical values in the figure shows the time period having elapsed since the start of light irradiation.

When no surfactant was introduced, an intense thermal convection was observed. Thus, the beads were not collected in the vicinity of spacer 33 (see FIG. 24(A)). In contrast, when a surfactant was introduced, it was observed that the thermal convection became gentle and the beads were collected in the vicinity of a spacer 33 (see FIG. 24(B)). This is considered as resulting from the following reason. Specifically, the surfactant adsorbs to the gas-liquid interface between dispersion liquid D and the gas therearound to thereby form a monomolecular film, so that the dispersion medium is less likely to evaporate, thereby suppressing acceleration of the thermal convection. In this way, not only the effect of accelerating the thermal convection but also the effect of suppressing acceleration of the thermal convection contributes to collection of the beads. Thus, achieving the effect of suppressing acceleration of the thermal convection may also be included in highly efficient collection of microscopic objects dispersed in a liquid, in terms of adjusting the flow rate in dispersion liquid D to the optimum rate for collection.

Figure 25:
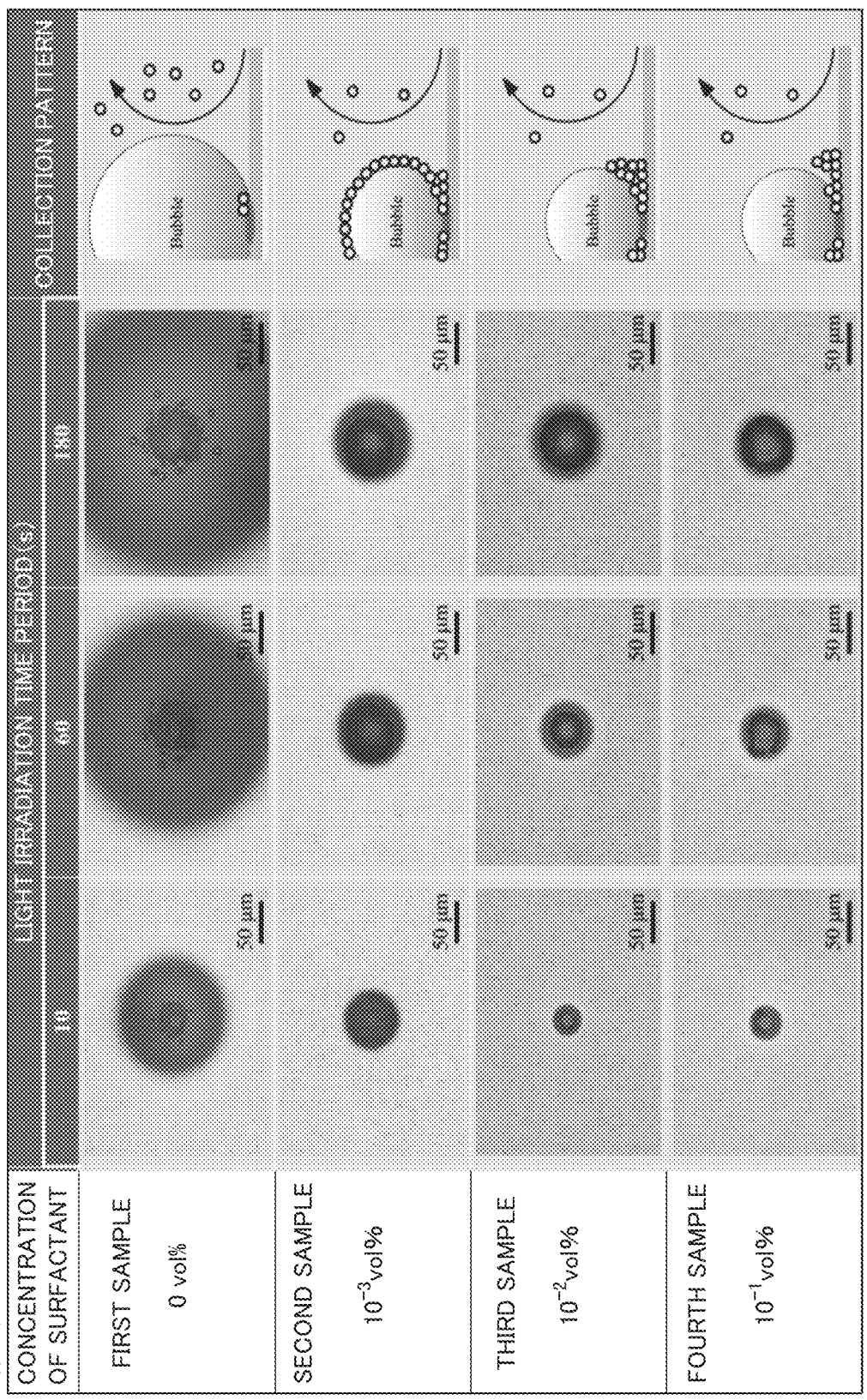
FIG. 25 is a diagram for illustrating an influence of the concentration of the surfactant.

FIG. 25 is a diagram for illustrating an influence of the concentration of the surfactant. In the example shown in FIG. 25, four types of dispersion liquids D (the first sample to the fourth sample) containing surfactants having different concentrations were prepared. The first sample does not contain a surfactant. The concentrations of the surfactants contained in the second sample, the third sample and the fourth sample were $1.0 \times 10^{-3}$, $1.0 \times 10^{-2}$, and $1.0 \times 10^{-1}$ (vol %), respectively.

The critical micelle concentration of Tween20 is $6.7 \times 10^{-3}$ (vol %). Thus, the concentration of the surfactant contained in the each of the third sample and the fourth sample is equal to or greater than the critical micelle concentration while the concentration of the surfactant contained in the second sample is less than the critical micelle concentration. The diameter of the laser spot was set at 2.5 μm while the laser output having passed through objective lens 7 was set at 0.1 W.

It turns out that, in accordance with the mechanism having been described in FIG. 15, the number of collected beads is increased more in the second sample to the fourth sample than in the first sample. From a viewpoint of increasing the number of beads to be collected, it is desirable that the concentration of the surfactant is equal to or greater than the critical micelle concentration particularly as in the third sample or the fourth sample. However, as in the second sample, the concentration of the surfactant may be less than the critical micelle concentration (a fraction of the critical micelle concentration in this example) as long as it is not so significantly lower than the critical micelle concentration (for example, as long as it is smaller by about single digit or double digits in order). On the contrary, it is not preferable that the concentration of the surfactant is excessively higher than the critical micelle concentration (for example, higher by triple digits in order). In other words, it is preferable that the concentration of the surfactant is approximately the same as the critical micelle concentration. This can be rephrased by stating that it is preferable that the concentration of the surfactant is within a prescribed range including the critical micelle concentration (for example, within the experimentally settable range that is equal to or greater than the concentration lower by double digits in order than the critical micelle concentration, and that is equal to or less than the concentration higher by double digits in order than the critical micelle concentration). In addition, FIG. 25 shows that microbubble MB is smaller in size as the concentration of the surfactant becomes higher.

Figure 26:
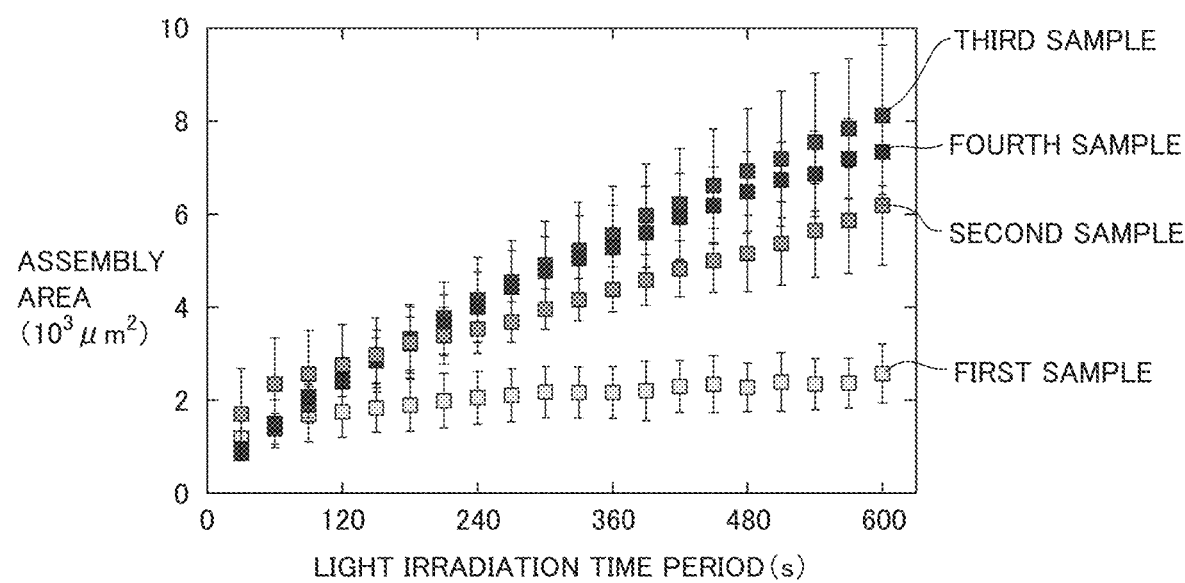
FIG. 26 is a diagram for illustrating an influence exerted by the concentration of the surfactant upon the assembly area of beads.

FIG. 26 is a diagram for illustrating an influence exerted by the concentration of the surfactant upon assembly area A of beads. In FIG. 26, the horizontal axis shows the light irradiation time period while the vertical axis shows assembly area A of beads.

FIG. 26 shows that assembly area A of beads is larger in the case where the concentration of the surfactant is equal to or greater than the critical micelle concentration (the third sample and the fourth sample) than in the case where the concentration of the surfactant is less than the critical micelle concentration (the first sample and the second sample). Particularly, assembly area A of beads is maximized in the third sample that is closest in concentration of the surfactant to the critical micelle concentration.

<Influence of Concentration of Beads>

Figure 27:
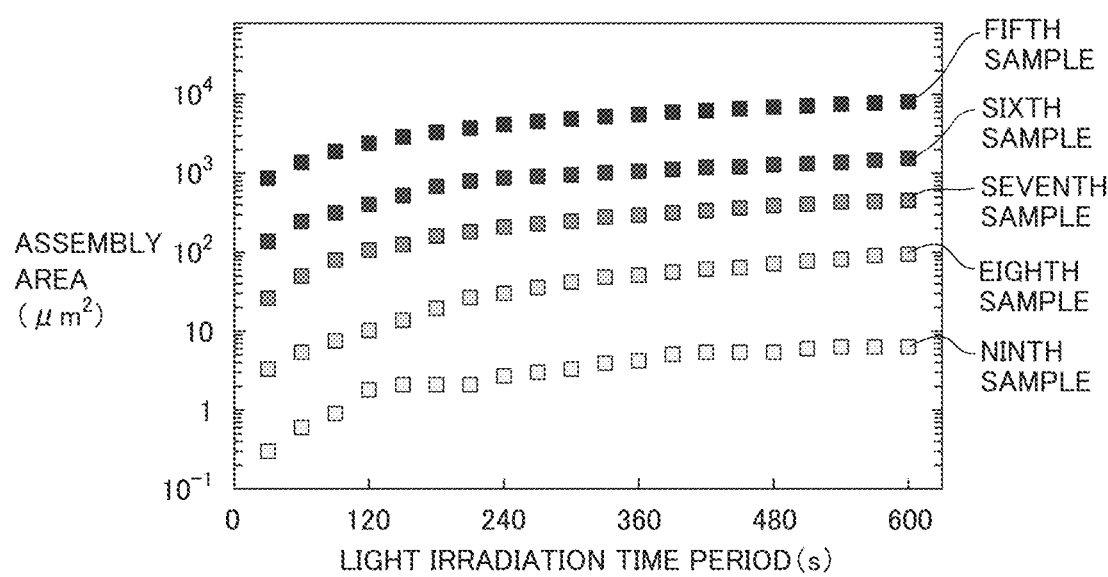
FIG. 27 is a diagram for illustrating an influence exerted by the concentration of beads upon collection of beads.
Figure 28:
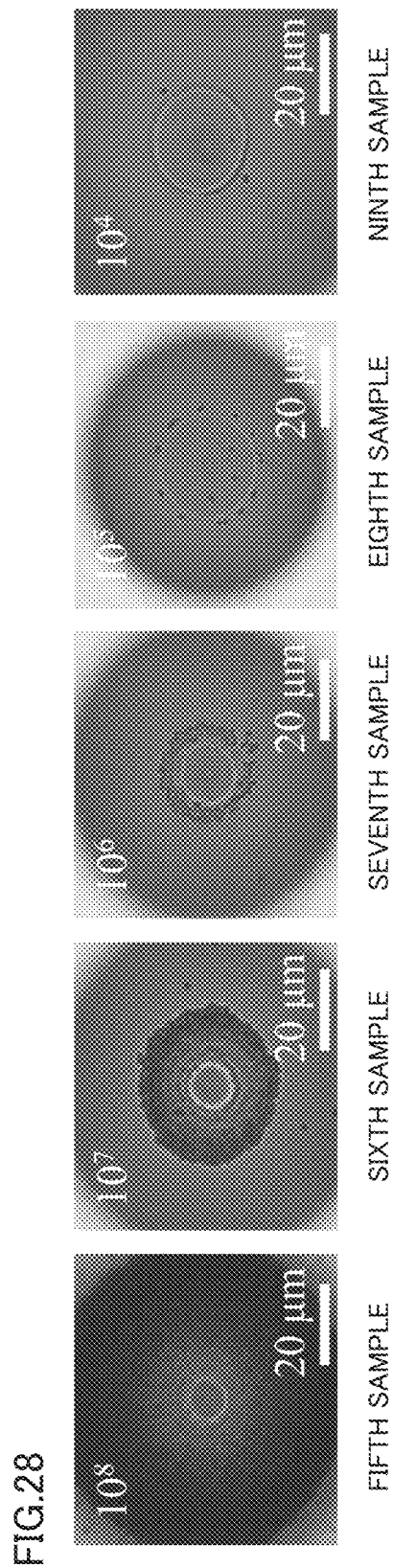
FIG. 28 shows images illustrating an example of a result of collecting beads after a lapse of 300 seconds since the start of light irradiation.

FIG. 27 is a diagram for illustrating an influence exerted by the concentration of beads upon collection of beads. In FIG. 27, the horizontal axis shows the light irradiation time period while the vertical axis shows assembly area A of beads on the logarithmic scale. FIG. 28 show images illustrating an example of a result of collecting beads after a lapse of 300 seconds since the start of light irradiation.

In this example, five types of dispersion liquids D having different concentrations of beads (the fifth sample to the ninth sample) were prepared. The concentrations of the beads contained in the fifth sample, the sixth sample, the seventh sample, the eighth sample, and the ninth sample were $4.55\times10^8$, $4.55\times10^{-7}$, $4.55\times10^6$, $4.55\times10^5$, $4.55\times10^4$ (particles/mL), respectively, in descending order. The same concentration of surfactant of $1.0\times10^{-2}$ (vol %) was used among the fifth sample to the ninth sample. As shown in FIG. 27, assembly area A is larger as the concentration of beads is higher. This is remarkably shown in a comparison image in FIG. 28.

Figure 29:
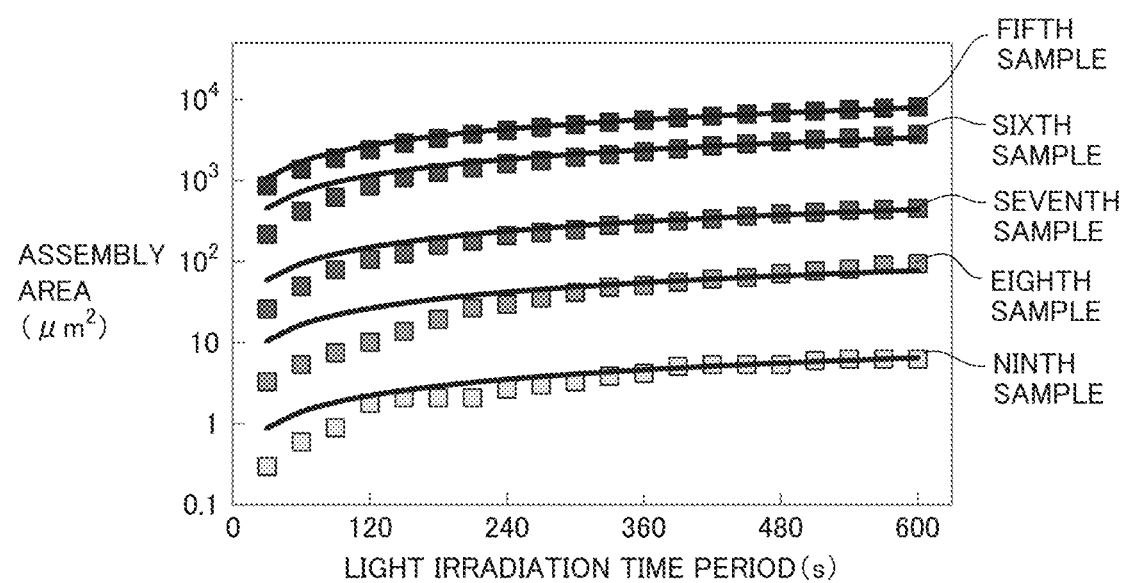
FIG. 29 is a diagram obtained by applying fitting (curvilinear regression) by the equation (1) to the diagram shown in FIG. 27.

FIG. 29 is a diagram obtained by applying fitting (curvilinear regression) by the equation (1) to the diagram shown in FIG. 27. In FIG. 29, each curved line obtained by regression analysis is indicated by a thick line.

Figure 30:
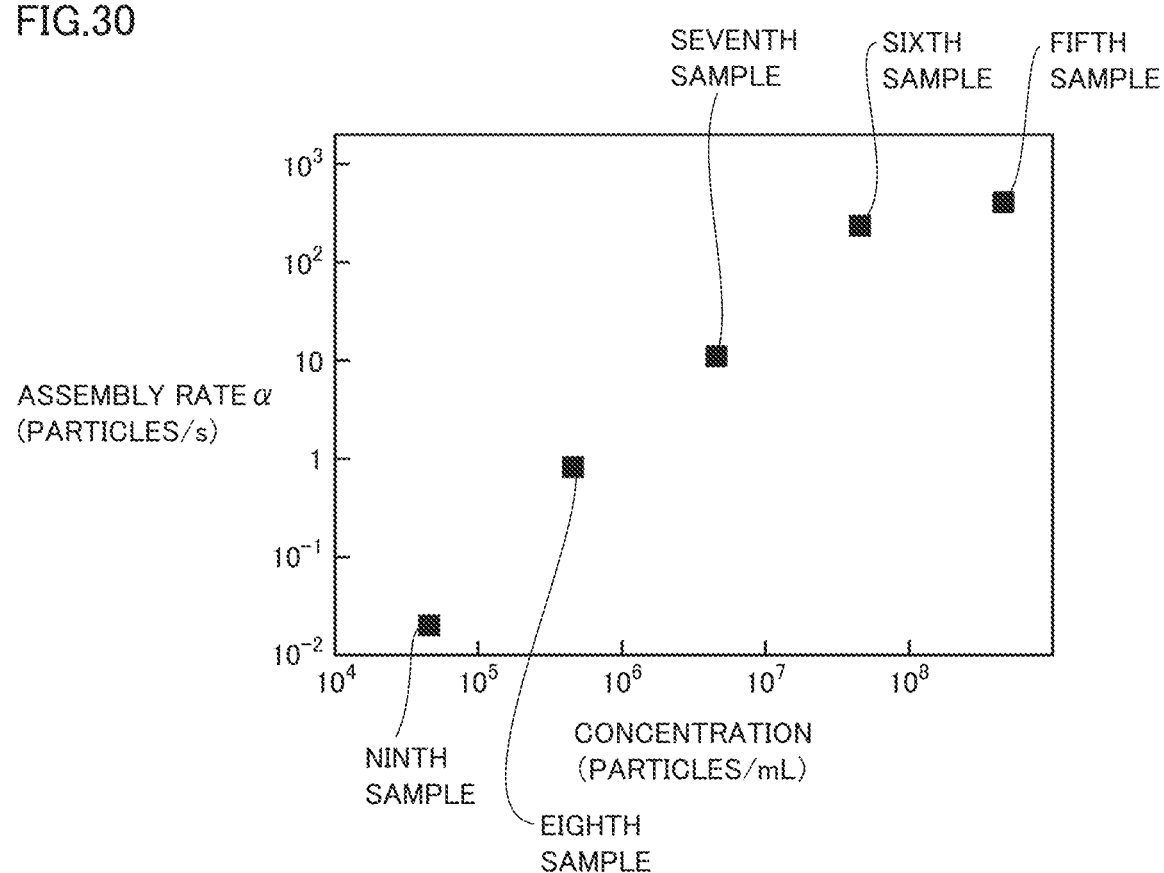
FIG. 30 is a diagram showing the relation between the concentration of beads and an assembly rate.

FIG. 30 is a diagram showing the relation between the concentration of beads and an assembly rate α. In FIG. 30, the horizontal axis shows the concentration of beads while the vertical axis shows assembly rate α. As shown in FIG. 30, it was confirmed that the correlation existed, showing that assembly rate α was higher as the concentration of beads was higher.

First Modification of Second Embodiment

The second embodiment has been described with regard to the configuration in which spacer 33 is provided in dispersion liquid D formed in a semielliptical sphere shape as a result of being dropped on substrate 31 (see FIG. 17), as in the comparative example. However, as having been described in the first embodiment, the spacer may be provided inside the dispersion liquid in the state where a concave meniscus is formed at the inner side surface of the container.

Figure 31:
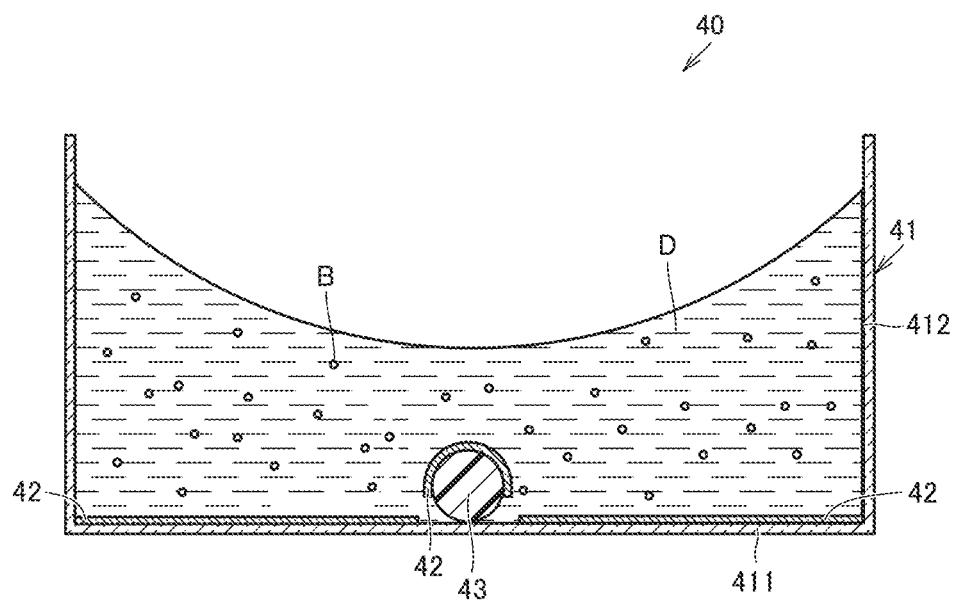
FIG. 31 is a diagram schematically showing the configuration of a collecting kit in the first modification of the second embodiment.

FIG. 31 is a diagram schematically showing the configuration of a collecting kit 40 in the first modification of the second embodiment. Referring to FIG. 31, collecting kit 40 includes a container 41, a thin film 42, and a spacer 43. Container 41 has a bottom surface 411 and an inner side surface 412. Bottom surface 411 and inner side surface 412 of container 41 are the same as bottom surface 111 and inner side surface 112, respectively, of container 11 (see FIG. 3) in the first embodiment. Furthermore, thin film 42 and spacer 43 are the same as thin film 32 and spacer 33 (see FIG. 17), respectively, in the second embodiment. Thus, the detailed explanation of the configuration of collecting kit 40 will not be repeated.

Second Modification of Second Embodiment

As a method of fixing the spacer onto the substrate, an explanation has been given with regard to the method of dropping a dispersion liquid having spacers dispersed therein onto a substrate and drying the substrate to thereby evaporate the dispersion medium. This method is simply carried out, but the spacer is relatively weakly fixed, so that the spacer may be peeled off from the substrate by a convection. Thus, a method of more firmly fixing a spacer is employed in the second modification of the second embodiment.

Figure 32:
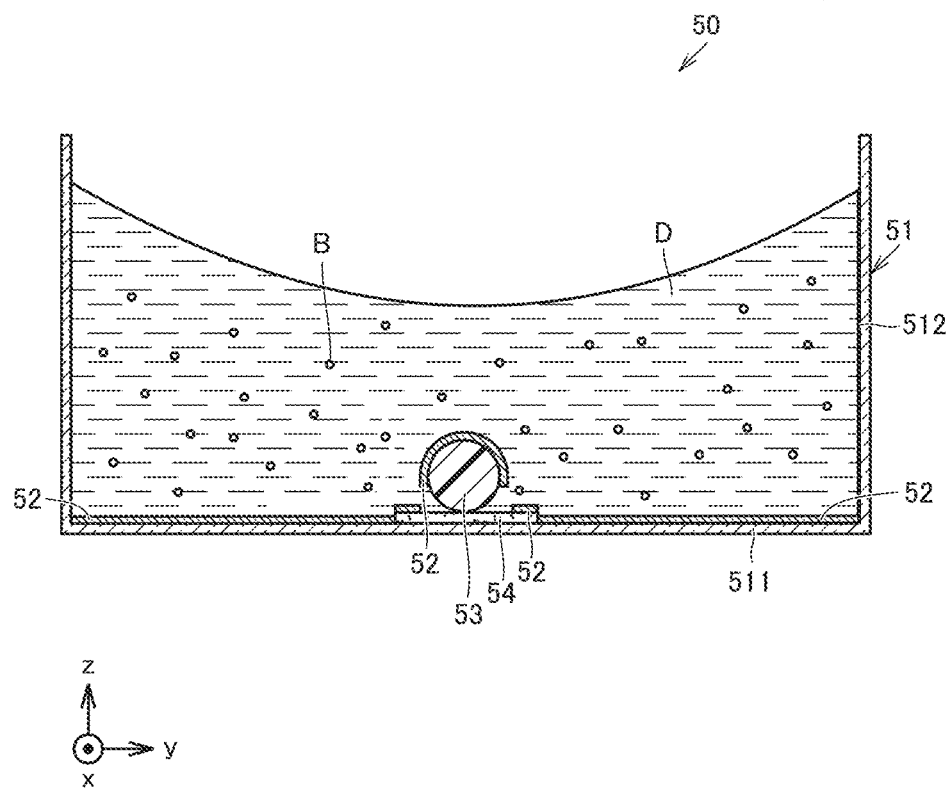
FIG. 32 is a diagram schematically showing the configuration of a collecting kit in the second modification of the second embodiment.

FIG. 32 is a diagram schematically showing the configuration of a collecting kit 50 in the second modification of the second embodiment. Referring to FIG. 32, collecting kit 50 includes a container 51, a thin film 52, a spacer 53, and an adhesion member 54. Container 51 has a bottom surface 511 and an inner side surface 512. Bottom surface 511 and inner side surface 512 of container 51 are the same as bottom surface 411 and inner side surface 412, respectively, of container 41 (see FIG. 31) in the first modification of the second embodiment.

Adhesion member 54 is provided between bottom surface 511 of container 51 and spacer 53 to allow adhesion between bottom surface 511 and spacer 53. Adhesion member 54 is made using a material that does not absorb laser beam L1 from laser beam source 5. Examples of such a material may be a transparent double-faced tape at least in the wavelength range (near-infrared range) of laser beam L1. The thickness of the double-faced tape is about 100 μm, for example. By using adhesion member 54 in this way, spacer 53 can be firmly fixed onto bottom surface 511. After spacer 53 is fixed onto bottom surface 511 with adhesion member 54 interposed therebetween, thin film 52 is formed by sputtering, for example. Thin film 52 is the same as thin film 42 in the second embodiment.

As described above, according to the second modification of the second embodiment, spacer 53 can be firmly fixed onto bottom surface 511 by using adhesion member 54. Thereby, spacer 53 can be prevented from being peeled off by a thermal convection.

Also in the second modification of the second embodiment, a surfactant may be introduced into dispersion liquid D as in the second embodiment. Thereby, the strength of the thermal convection can be adjusted (the thermal convection can be rendered gentle) such that the beads are readily collected in the vicinity of spacer 53. In the case where a meniscus is formed to be concave with respect to the gas-liquid interface, the distance between the laser spot and the gas-liquid interface located thereabove is more likely to be smaller than that in the case where a meniscus is not formed to be concave with respect to the gas-liquid interface (see FIG. 17). Accordingly, the temperature of the gas-liquid interface above the laser spot is more likely to rise. As a result, the influence of evaporation of the dispersion medium from the gas-liquid interface, that is, the effect of accelerating the thermal convection by evaporation of the dispersion medium, is more likely to be increased. Thus, when a meniscus is formed to be concave with respect to the gas-liquid interface, it is particularly important to utilize the effect of suppressing evaporation of the dispersion medium by adsorption of the surfactant onto the gas-liquid interface.

Third Modification of Second Embodiment

FIG. 33 is a diagram schematically showing the configuration of a collecting kit 60 in the third modification of the second embodiment. FIG. 33(A) schematically shows a cross-section of collecting kit 60. FIG. 33(B) shows a photograph taken from above collecting kit 60. The configuration of collecting kit 60 is basically the same as the configuration of collecting kit 50 (see FIG. 32) in the second modification of the second embodiment. It is to be noted that collecting kit 60 is different from collecting kit 50 in that dispersion liquid D is held in a container 61 such that the gas-liquid interface is located higher than the upper end of an inner side surface 612.

In this way, even in the case of using inner side surface 612 at which immersion wetting occurs due to dispersion liquid D, the gas-liquid interface is located higher than the upper end of inner side surface 612 depending on the amount of dropped (the amount of held) dispersion liquid D. The state where immersion wetting occurs at inner side surface 612 due to dispersion liquid D in this way is not limited to the state where a meniscus is formed to be concave with respect to the gas-liquid interface but may also include the state where a meniscus is formed to be convex with respect to the gas-liquid interface. However, according to the third modification of the second embodiment, container 61 having inner side surface 612 is used to thereby allow adjustment of the height of the gas-liquid interface and the shape of the gas-liquid interface (the shape of meniscus), in contrast to the configuration using substrate 91 as in the comparative example.

Figure 34:
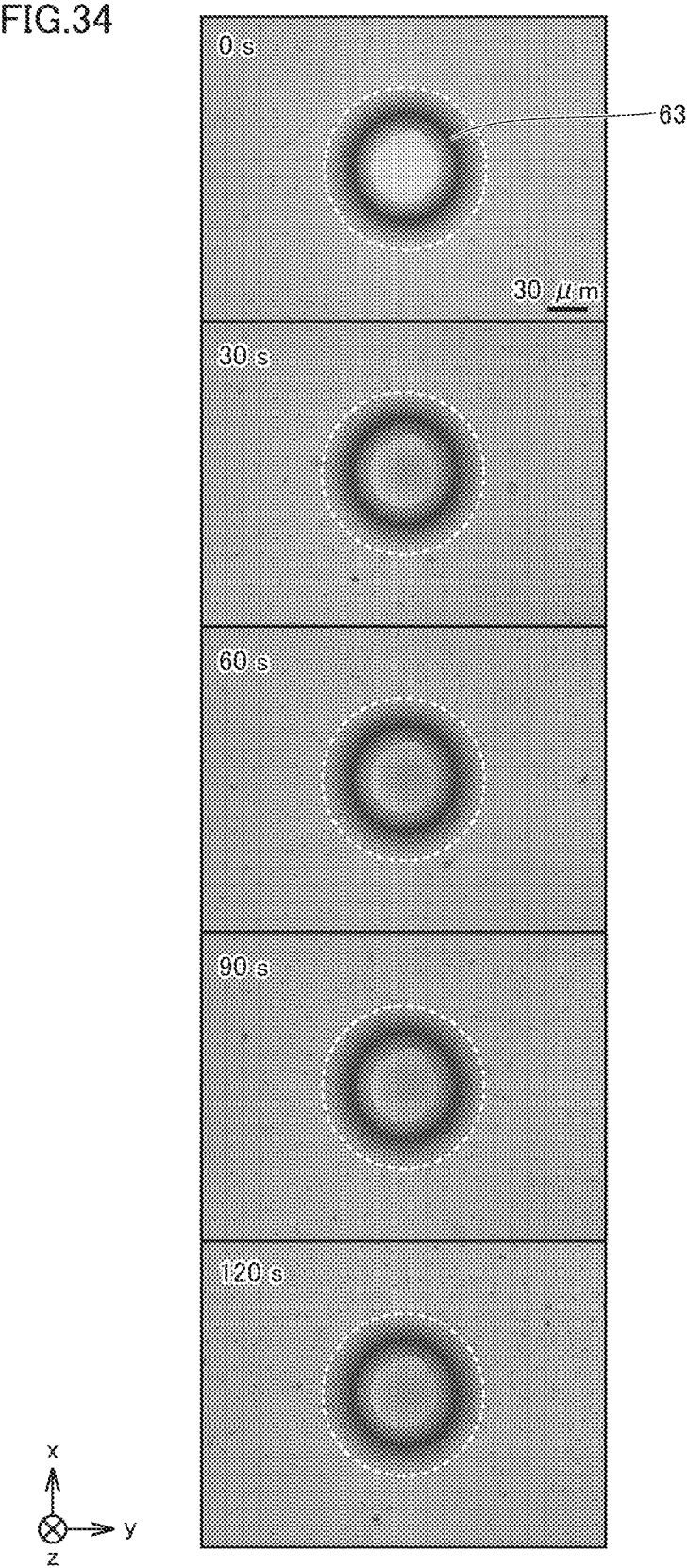
FIG. 34 shows sequential images illustrating an example of a result of collecting beads in the case where a surfactant is introduced in the third modification of the second embodiment.

FIG. 34 shows sequential images illustrating an example of a result of collecting beads in the case where a surfactant is introduced in the third modification of the second embodiment. Each of the numerical values in the figure shows the time period having elapsed since the start of light irradiation. Height H of the gas-liquid interface in the center of container 61 (above the laser spot) was 2540 µm (at a scale of 1910 on the above-mentioned scale) as a result of correction in consideration of the refractive index of water as a dispersion medium. The height of the gas-liquid interface at inner side surface 612 was within the range of 1500 µm to 1720 µm, which was approximately equal to the height of inner side surface 612 (at a scale of 1724 on the above-mentioned scale), without requiring correction in consideration of the refractive index of water.

As in the second embodiment (see FIG. 24), a surfactant is introduced, so that a thermal convection becomes gentle. Thus, beads are more likely to be collected in the vicinity of spacer 53.

As described above, according to the third modification of the second embodiment, dispersion liquid D is held in container 61 such that the gas-liquid interface is located higher than the upper end of inner side surface 612. Also in this state, a surfactant of proper concentration is introduced into dispersion liquid D to thereby reduce the amount of evaporation of the dispersion medium, so that an excessively intense thermal convection can be suppressed. As a result, a thermal convection with appropriate strength can be produced, so that microscopic objects such as beads can be collected in the vicinity of spacer 53.

Third Embodiment

The third embodiment will be hereinafter described with regard to another configuration of the collecting kit that can suppress damage to bacteria B by heat. The entire configuration of the collecting apparatus according to the third embodiment is the same as the configuration of collecting apparatus 1 (see FIG. 1) in the first embodiment.

Figure 35:
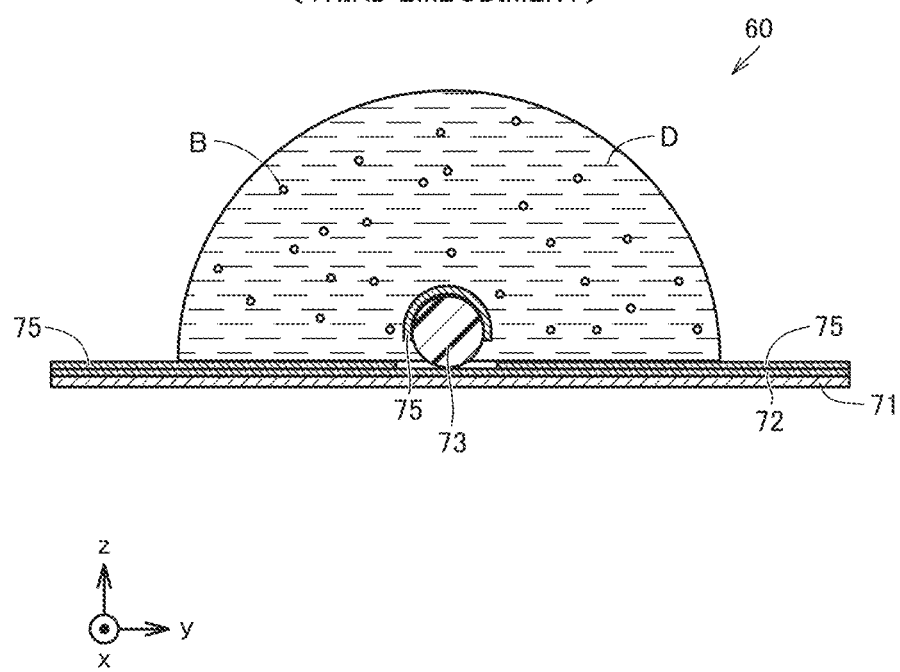
FIG. 35 is a diagram schematically showing the configuration of a collecting kit in the third embodiment.

FIG. 35 is a diagram schematically showing the configuration of a collecting kit 70 in the third embodiment. Referring to FIG. 35, collecting kit 70 is different from collecting kit 30 (see FIG. 17) in the second embodiment in that it includes two thin films 72 and 75. A substrate 71 and a spacer 73 of collecting kit 70 are the same as substrate 31 and spacer 33, respectively, of collecting kit 30.

FIG. 36 is a diagram for more specifically illustrating the configuration around spacer 73 shown in FIG. 35. The configuration shown in FIG. 36(A) can be prepared as follows, for example. Specifically, thin film 72 is first formed on substrate 71, for example, by sputtering. Then, spacer 73 is fixed (formed) onto thin film 72. The method of fixing spacer 73 is the same as the above-mentioned method of fixing spacer 33. Then, thin film 75 is formed, for example, by sputtering, further on substrate 71 to which spacer 73 is fixed.

Each of thin films 72 and 75 is a metal thin film having a thickness in the nanometer order, for example. In the third embodiment, each of thin films 72 and 75 was a gold thin film and formed to have a thickness of 10 nm. However, the material of thin film 72 may be different from the material of thin film 75, and the thickness of thin film 72 may be different from the thickness of thin film 75.

Referring to FIG. 36(B), upon light irradiation, a part of laser beam L1 is converted into heat by thin film 72 (lower region LR) while another part of laser beam L1 is converted into heat by thin film 75 (upper region UR). The proportion of the amount of heat generated by thin film 72 and the amount of heat generated by thin film 75 is set mainly depending on the thickness of each of thin films 72 and 75. When the same thickness is employed as described above, the amount of heat generated by thin film 72 is greater than the amount of heat generated by thin film 75. It is to be noted that thin film 72 and thin film 75 correspond to the "first photothermal conversion layer" and the "second photothermal conversion layer", respectively, according to the present disclosure.

In the third embodiment, spacer 73 is provided. Spacer 73 is significantly lower in thermal conductivity than thin films 72 and 75. Thus, the heat generated in each of thin films 72 and 75 is less likely to be conducted to the inside of spacer 73. Accordingly, the temperature of spacer 73 is less likely to rise. Furthermore, the heat generated in upper region UR of thin film 75 is conducted and spread through the surface (thin film 65 on the surface) of spacer 73. The heat capacity of thin film 75 is relatively small, and the contact area between thin film 75 and dispersion liquid D therearound is relatively large. Therefore, thin film 75 is effectively cooled by heat exchange between thin film 75 and dispersion liquid D.

In this way, also in the third embodiment, an excessive rise in temperature in the collecting region of bacteria B can be prevented by providing spacer 73 as in the second embodiment. Thus, damage to collected bacteria B by heat can be suppressed. Furthermore, according to the third embodiment, the amount of generated heat is increased as the amount of formed thin film is increased, as compared with the second embodiment. Thus, bacteria B can be collected by a lower laser output.

<Result of Collecting Beads>

Figure 37:
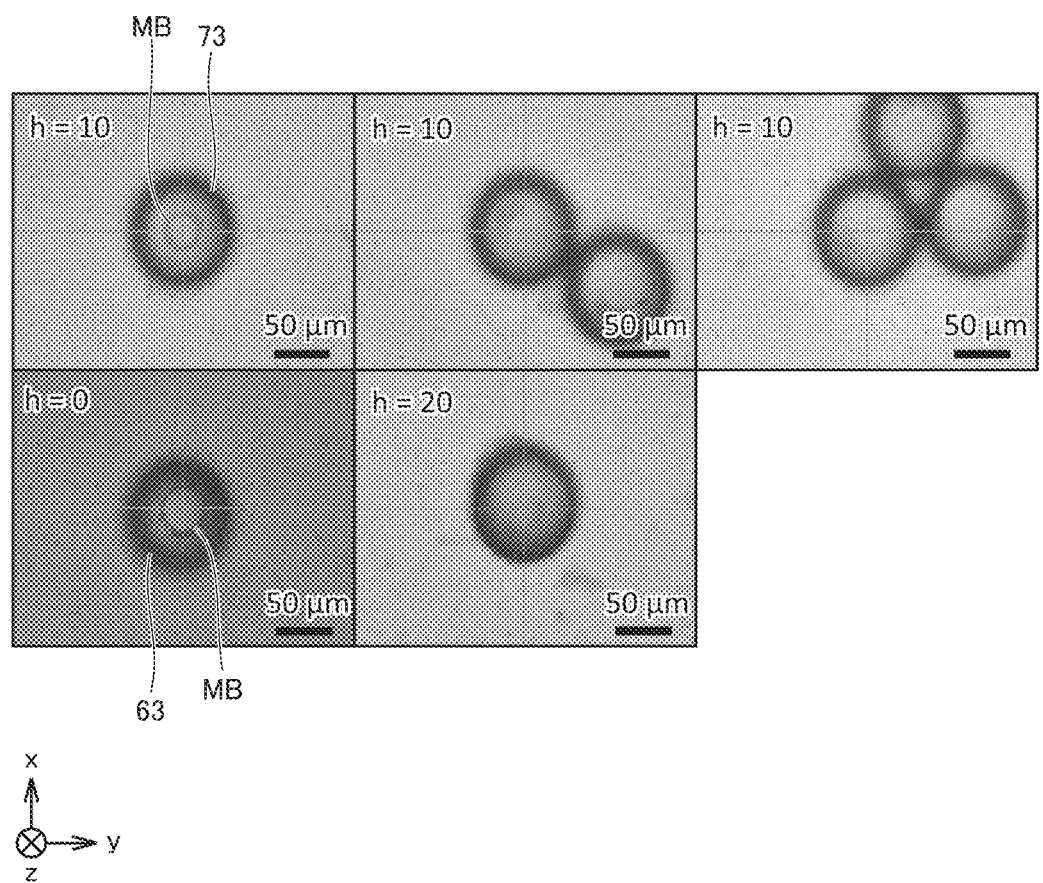
FIG. 37 shows images illustrating the state where beads are collected in the third embodiment.

FIG. 37 show images illustrating the state where beads are collected in the third embodiment. In the example shown in FIG. 37, height h of the beam waist was set at 0 µm, 10 µm, or 20 µm. In the third embodiment, it was confirmed that the beads were collected at each height h.

<Determination as to Whether Bacteria are Alive or Dead>

In the third embodiment, height h of the beam waist of laser beam L1 was set at 0 µm. In the comparative example, the laser output was set at 1.0 W while the laser output during collection of *Escherichia coli* was set at 0.1 W or 0.2 W. The irradiation time period of laser beam L1 was set at one minute.

Figure 38:
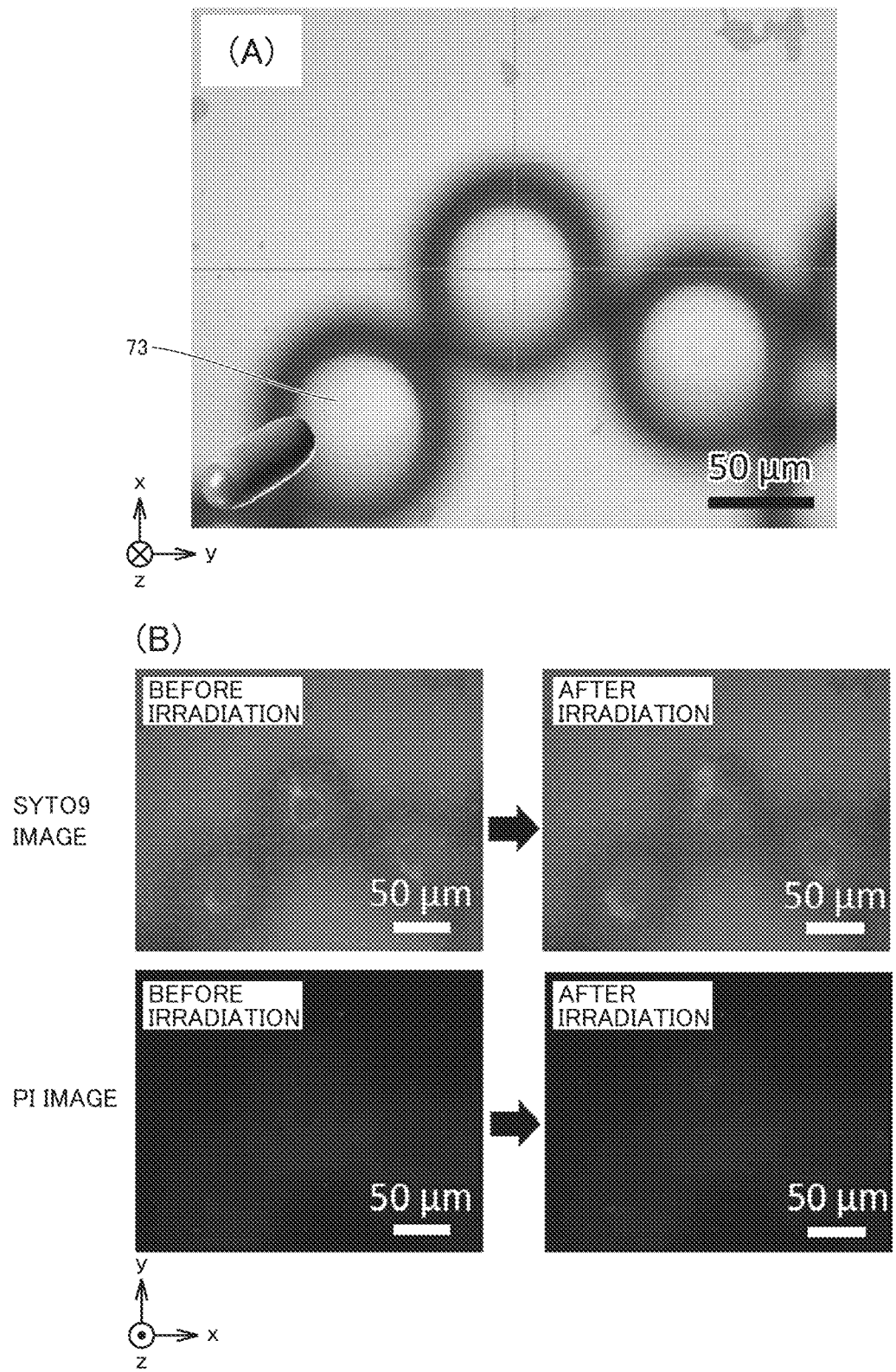
FIG. 38 is a diagram showing a result of collecting *Escherichia coli* in the case where a laser output is 0.1 W in the third embodiment.
Figure 39:
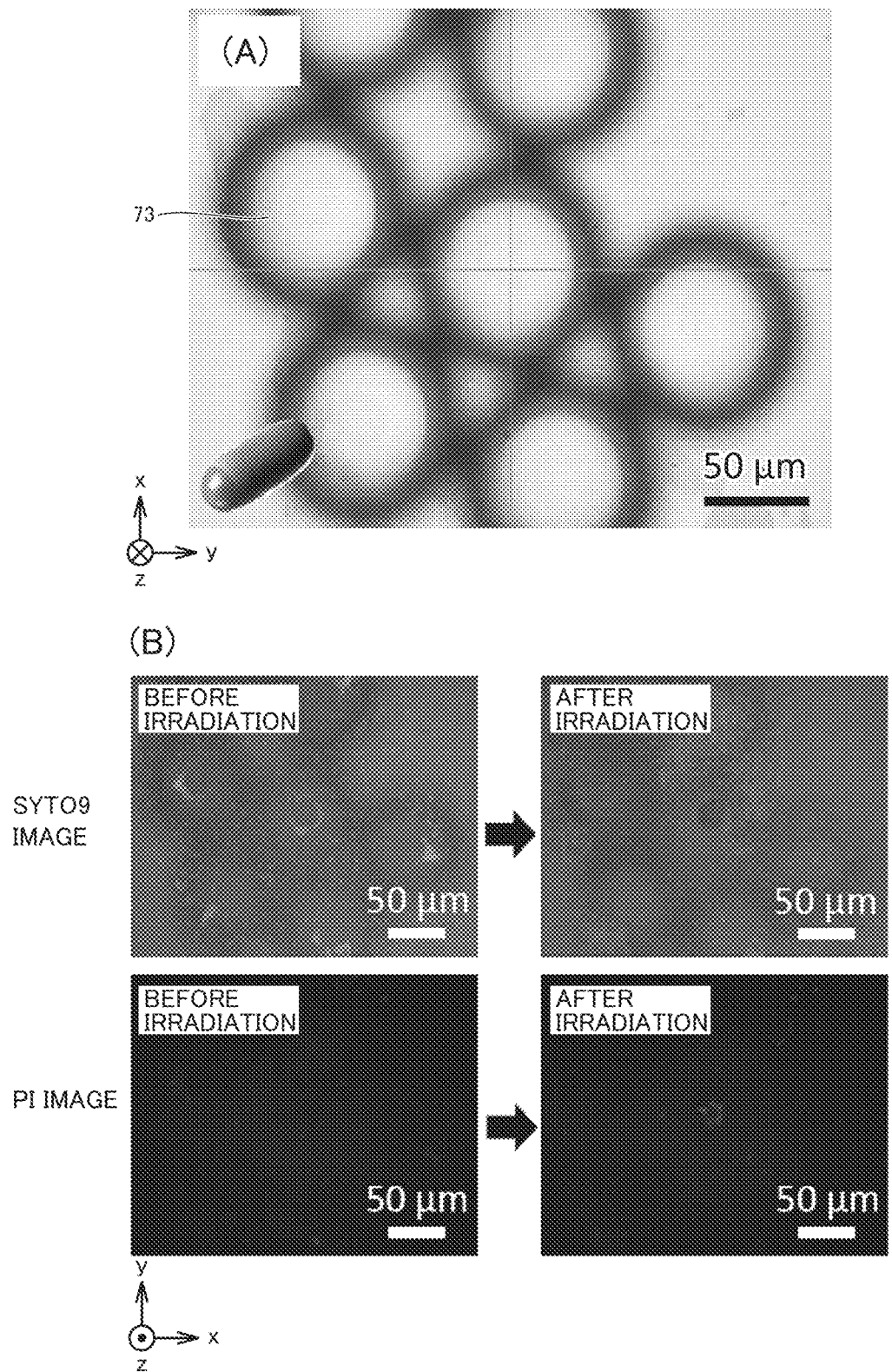
FIG. 39 is a diagram showing a result of collecting *Escherichia coli* in the case where a laser output is 0.2 W in the third embodiment.

FIG. 38 is a diagram showing a result of collecting *Escherichia coli* in the case where a laser output is 0.1 W in the third embodiment. FIG. 39 is a diagram showing a result of collecting *Escherichia coli* in the case where a laser output is 0.2 W in the third embodiment. The images are arranged in the same manner as the images in FIG. 22 or FIG. 23.

The transmission images in FIGS. 38(A) and 39(A) show that bacteria B can be collected even when the laser output is as low as approximately 0.1 W. Furthermore, the PI images in FIGS. 38(B) and 39(B) show that dead bacteria hardly exist in collected bacteria B.

As described above, according to the third embodiment, spacer 73 having low thermal conductivity is provided as in the second embodiment, so that the heat generated by the photothermal effect of thin films 72 and 75 is less likely to be conducted to the collecting region of bacteria B. Accordingly, an excessive rise in temperature in the collecting region of bacteria B can be prevented, so that damage to bacteria B by heat can be suppressed. Furthermore, by using two thin films 72 and 75, the amount of generated heat is increased as compared with the configuration in the second embodiment. Thus, bacteria B can be collected by a lower laser output.

Modification of Third Embodiment

As in the comparative example of the second embodiment, the configuration around spacer 73 in the third embodiment may be applied to the inside of the dispersion liquid in which a concave meniscus is formed at the inner side surface of the container.

Figure 40:
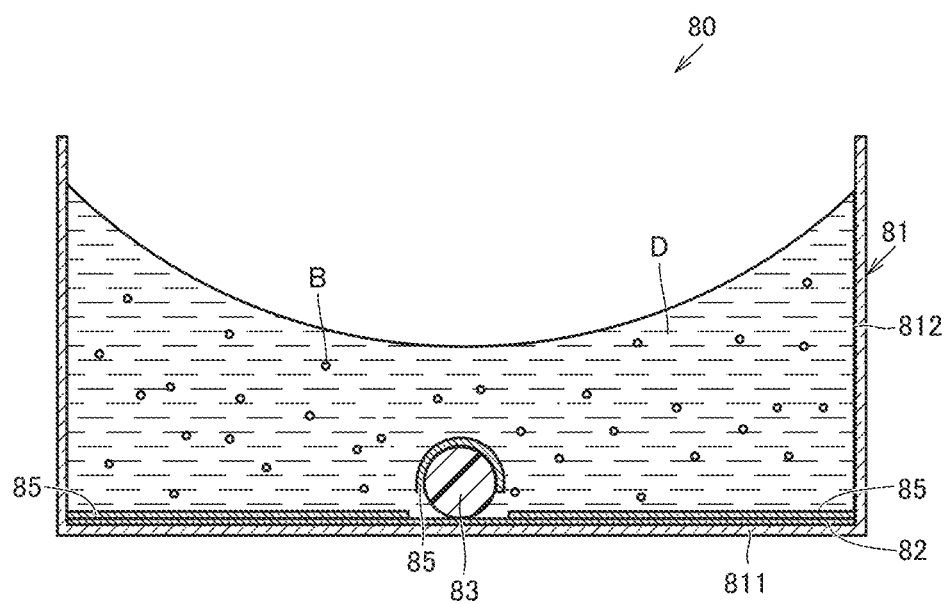
FIG. 40 is a diagram schematically showing the configuration of a collecting kit in a modification of the third embodiment.

FIG. 40 is a diagram schematically showing the configuration of a collecting kit 80 in a modification of the third embodiment. Collecting kit 80 includes a container 81, a thin film 82, a spacer 83, and a thin film 85. Container 81 has a bottom surface 811 and an inner side surface 812. Bottom surface 811 and inner side surface 812 of container 81 are the same as bottom surface 111 and inner side surface 112, respectively, of container 11 (see FIG. 3) in the first embodiment. Furthermore, thin films 82 and 85 and spacer 83 are the same as thin films 72 and 75 and spacer 73, respectively, (see FIG. 35) in the third embodiment. Thus, the detailed explanation about the configuration of collecting kit 80 will not be repeated.

The configuration of the second embodiment (and the first to third modifications thereof) as described above and the configuration of the third embodiment (and a modification thereof) can be selected as appropriate to be used depending on the amount or the heat resistance of the microscopic objects to be collected. For example, for the purpose of collecting a small amount of bacteria and the like that are relatively less resistant to heat, the configuration of the second embodiment (or the first to third modifications thereof) can be employed. On the other hand, when it is required to collect a large amount of bacteria and the like that are resistant to a high temperature to some extent, the configuration of the third embodiment (or the modification thereof) can be employed.

Furthermore, the configurations of microwell array 20A and microlens array 7A having been described in the modification of the first embodiment (see FIG. 16) may be combined with the configurations of the second embodiment (and the first to third modifications thereof) and the third embodiment (and the modification thereof). Furthermore, adhesion member 54 (see FIG. 32) and a surfactant (see FIG. 34) can also be combined as appropriate with other embodiments and modifications.

The first embodiment to the third embodiment and the modifications thereof have been described with regard to an example in which dispersion liquid D is an aqueous liquid and inner side surface 112 of container 11 exhibits hydrophilicity. This allows container 11 to hold dispersion liquid D such that a meniscus is formed to be concave with respect to the gas-liquid interface. However, dispersion liquid D may be an organic solvent. In this case, container 11 having inner side surface 112 exhibiting solvophilicity (for example, lipophilicity or hydrophobicity) is used. In this way, container 11 is allowed to hold dispersion liquid D such that a meniscus is formed to be concave with respect to the gas-liquid interface, as in the case where dispersion liquid D is an aqueous liquid.

Other Examples

A nanodiamond is a nano-substance on which attention has been focused in recent years, and is expected to be applied to biological fields (medical fields and the like) since it exhibits biocompatibility. By way of example, a nanodiamond having a crystal structure containing a compound defect (NV) constituted of a nitrogen atom (N) and hole center (V) emits fluorescence, and therefore, such a nanodiamond has been considered to be utilized as a fluorescent-labeling agent for observing the dynamics (movement and structural change) of biological molecules. In this example, the result of collecting nanodiamonds will be described. Since the entire configuration of the collecting apparatus is the same as the configuration of collecting apparatus 1 in the first embodiment (see FIG. 1), the detailed explanation thereof will not be repeated. In each of images shown in the FIGS. 41 to 45 described below, the center of each image corresponds to the light irradiation position (a laser spot).

<Result of Collecting Nanodiamonds>

Figure 43:
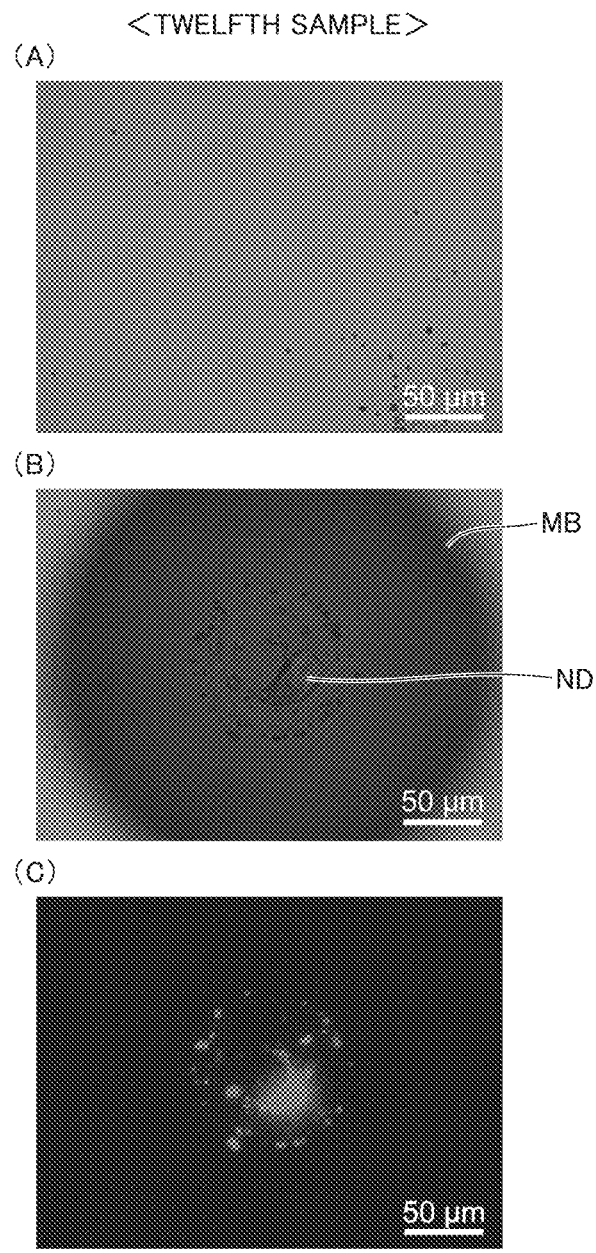
FIG. 43 is a diagram for illustrating a result of collecting nanodiamonds in the twelfth sample.

In the example, the result of collecting nanodiamonds by light irradiation will be described. FIGS. 41, 42 and 43 described below show the results of collecting nanodiamonds ND in the tenth sample, the eleventh sample and the twelfth sample, respectively. The particle size of nanodiamond ND was 10 nm, 40 nm, and 100 nm in the tenth sample, the eleventh sample and the twelfth sample, respectively. In addition, the light emission wavelength of nanodiamond ND having a particle size of 10 nm is about 640 nm. The light emission wavelength of nanodiamond ND having a particle size of 40 nm is about 660 nm to 680 nm. The light emission wavelength of nanodiamond ND having a particle size of 100 nm is about 680 nm to 700 nm.

FIG. 41 is a diagram for illustrating a result of collecting nanodiamonds ND in the tenth sample. FIG. 42 is a diagram for illustrating a result of collecting nanodiamonds ND in the eleventh sample. FIG. 43 is a diagram for illustrating a result of collecting nanodiamonds ND in the twelfth sample. Each of FIGS. 41 to FIG. 43 shows, beginning at the top, an transmission image obtained at the start of light irradiation, a transmission image obtained after the end of light irradiation (after 60 seconds since the start of light irradiation), and a fluorescence observation image obtained after the end of light irradiation.

The transmission images shown in FIGS. 41(B), 42(B) and 43(B) show that nanodiamonds ND are collected between substrate 31 and microbubble MB produced around the laser spot (the center in each figure). Furthermore, by the fluorescence observation images shown in FIGS. 41(C), 42(C) and 43(C), luminescence originated from nanodiamond ND was confirmed.

<Result of Collecting Nanodiamonds in Cell>

The following is an explanation about the collection result obtained by applying light to the thirteenth sample prepared so as to contain both a nanodiamond and a biological sample. The thirteenth sample contains nanodiamond ND having a particle size of 10 nm and a human acute lymphoblastic leukemia cell line (CCRF-CEM). In the following, CCRF-CEM will be referred to as a "cell" for simplicity.

FIG. 44 is a diagram for illustrating a result of collecting nanodiamonds ND in the case of light irradiation at one position in the thirteenth sample. FIG. 45 is a diagram for illustrating a result of collecting nanodiamonds ND in the case of light irradiation at another position in the thirteenth sample. FIG. 44 shows a transmission image obtained at the start of light irradiation, a transmission image obtained after the end of light irradiation (after 60 seconds since the start of laser irradiation), and fluorescence observation images obtained after the end of light irradiation (FIGS. 44(C) and 44(D)). The exposure time period is different between FIGS. 44(C) and 44(D) while the analog gain is also different between FIGS. 44(C) and 44(D) (the exposure time period is 30 seconds and the analog gain is 22.5 in FIG. 44(C) while the exposure time period is 100 seconds and the analog gain is 13.6 in FIG. 44(D)). The conditions for taking images in FIG. 45 are the same as those in FIG. 44 except that the laser irradiation time period is 120 seconds.

FIGS. 44 and 45 show that nanodiamonds ND can be collected on the cell surface. In particular, a larger number of cells shine not only between microbubble MB and substrate 31 but also in the vicinity of microbubble MB more brightly in the case of the collection result in FIG. 45 including a longer irradiation time period than in the case of the collection result in FIG. 44. Thus, it turns out that a large number of nanodiamonds ND were collected. This shows that a longer laser irradiation time period allows more nanodiamonds ND to be collected in a cell.

It should be understood that the embodiments disclosed herein are illustrative and non-restrictive in every respect. The scope of the present invention is defined by the terms of the claims, rather than the description of the embodiments provided above, and is intended to include any modifications within the meaning and scope equivalent to the terms of the claims.

INDUSTRIAL APPLICABILITY

The present disclosure can be utilized as a collecting apparatus for collecting microscopic objects such as biological substances useful for human beings. For example, a nanodiamond and a fluorochrome as a biomarker can be collected in a cell and can be utilized for achieving highly efficient bioimaging. Also, the present disclosure can be utilized in the medical field for new drug development, for example, for collecting a small amount of medical substances at the light irradiation position to be set at a high concentration, and for evaluating the influence upon cells or living tissues around the light irradiation position.

The invention claimed is:

1. A collecting apparatus for microscopic objects the collecting apparatus being configured to collect microscopic objects having sizes ranging from a nanometer order to a micrometer order, the collecting apparatus comprising:
   a light source configured to emit light;
   a container configured to hold a dispersion liquid in which the microscopic objects are dispersed; wherein:
   the container has:
      a bottom surface on which a photothermal conversion member for converting the light from the light source into heat is formed, and
      an inner surface at which immersion wetting occurs by the dispersion liquid when the inner side surface comes into contact with the dispersion liquid, and
   the photothermal conversion member includes a first photothermal conversion layer and a second photothermal conversion layer,
   the first photothermal conversion layer is formed on the bottom surface,
   the container further includes a heat insulating spacer fixed onto the first photothermal conversion layer,
   the second photothermal conversion layer is formed on the heat insulating spacer,
   the heat insulating spacer is lower in thermal conductivity than the first photothermal conversion layer and the second photothermal conversion layer, and
   the light source is configured to irradiate the first photothermal conversion layer and the second photothermal conversion layer with the light that is within an absorption wavelength range of each of the first photothermal conversion layer and the second photothermal conversion layer and that is out of an absorption wavelength range of the heat insulating spacer.

* * * * *